United States Patent
Lancaster et al.

(10) Patent No.: US 12,240,881 B2
(45) Date of Patent: *Mar. 4, 2025

(54) ULTRA-LONG ACTING INSULIN-FC FUSION PROTEIN AND METHODS OF USE

(71) Applicant: DECHRA LIMITED, Skipton (GB)

(72) Inventors: Thomas M. Lancaster, Wenham, MA (US); Todd C. Zion, Marblehead, MA (US)

(73) Assignee: Dechra Limited, Skipton (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/486,310

(22) Filed: Oct. 13, 2023

(65) Prior Publication Data

US 2024/0101636 A1    Mar. 28, 2024

Related U.S. Application Data

(63) Continuation of application No. 17/527,486, filed on Nov. 16, 2021, now Pat. No. 11,814,418, which is a continuation of application No. 17/226,847, filed on Apr. 9, 2021, now Pat. No. 11,192,930.

(60) Provisional application No. 63/008,520, filed on Apr. 10, 2020.

(51) Int. Cl.
  *C07K 14/62* (2006.01)
  *A61K 38/00* (2006.01)

(52) U.S. Cl.
  CPC .............. *C07K 14/62* (2013.01); *A61K 38/00* (2013.01); *C07K 2319/30* (2013.01)

(58) Field of Classification Search
  None
  See application file for complete search history.

(56) References Cited

U.S. PATENT DOCUMENTS

| | | | |
|---|---|---|---|
| 8,188,231 B2 | 5/2012 | Lazar et al. | |
| 8,933,207 B2 | 1/2015 | Chen et al. | |
| 9,074,015 B2 | 7/2015 | Lancaster et al. | |
| 9,855,318 B2 | 1/2018 | Baldwin et al. | |
| 10,597,435 B2 | 3/2020 | Lancaster et al. | |
| 10,709,766 B2 | 7/2020 | Baldwin et al. | |
| 10,822,386 B2 | 11/2020 | Weiss | |
| 10,851,147 B2 | 12/2020 | Lancaster et al. | |
| 10,870,686 B2 | 12/2020 | Lancaster et al. | |
| 10,894,089 B2 | 1/2021 | Heo et al. | |
| 10,947,292 B2 | 3/2021 | Lancaster et al. | |
| 10,961,294 B2 | 3/2021 | Lancaster et al. | |
| 11,186,623 B2 | 11/2021 | Lancaster et al. | |
| 11,192,930 B2 * | 12/2021 | Lancaster | C07K 14/62 |
| 11,814,418 B2 * | 11/2023 | Lancaster | C07K 14/62 |
| 2003/0040601 A1 | 2/2003 | Diers et al. | |
| 2012/0093814 A1 | 4/2012 | Canada et al. | |
| 2013/0142795 A1 | 6/2013 | Bai et al. | |
| 2013/0190475 A1 | 7/2013 | Chen et al. | |
| 2013/0190476 A1 | 7/2013 | Lancaster et al. | |
| 2014/0037699 A1 | 2/2014 | Zion et al. | |
| 2014/0302028 A1 | 10/2014 | Zha | |
| 2014/0357843 A1 | 12/2014 | Oh et al. | |
| 2016/0289290 A1 | 10/2016 | Meehl et al. | |
| 2016/0324932 A1 | 11/2016 | Baldwin et al. | |
| 2018/0009869 A1 | 1/2018 | Lu et al. | |
| 2018/0161448 A1 | 6/2018 | Heo et al. | |
| 2018/0177851 A1 | 6/2018 | Baldwin et al. | |
| 2018/0291076 A1 | 10/2018 | Kjeldsen et al. | |
| 2019/0315828 A1 | 10/2019 | Lancaster et al. | |
| 2019/0382439 A1 | 12/2019 | Kim et al. | |
| 2020/0131243 A1 | 4/2020 | Lancaster et al. | |
| 2020/0140516 A1 | 5/2020 | Weiss | |
| 2020/0140517 A1 | 5/2020 | Weiss | |
| 2020/0157169 A1 | 5/2020 | Lancaster et al. | |
| 2020/0157170 A1 | 5/2020 | Lancaster et al. | |
| 2020/0157171 A1 | 5/2020 | Lancaster et al. | |
| 2020/0231646 A1 | 7/2020 | Lancaster et al. | |
| 2020/0299343 A1 | 9/2020 | Doerner et al. | |
| 2020/0407413 A1 | 12/2020 | Lancaster et al. | |
| 2020/0407414 A1 | 12/2020 | Lancater et al. | |
| 2021/0300983 A1 | 9/2021 | Lancaster et al. | |
| 2021/0309709 A1 | 10/2021 | Lancaster et al. | |
| 2021/0324033 A1 | 10/2021 | Lancaster et al. | |
| 2021/0340212 A1 | 11/2021 | Zion et al. | |

FOREIGN PATENT DOCUMENTS

| | | |
|---|---|---|
| CN | 101891823 A | 11/2010 |
| CN | 103509118 A | 1/2014 |
| EP | 0303380 A2 | 2/1989 |
| EP | 2963056 A1 | 1/2016 |
| EP | 3303380 A1 | 4/2018 |
| EP | 3517544 A1 | 7/2019 |
| EP | 3656792 A1 | 5/2020 |

(Continued)

OTHER PUBLICATIONS

Alleva D. G, et al., "Immunological Characterization and Therapeutic Activity of an Altered-peptide Ligand, NBI-6024, Based on the Immunodominant Type 1 Diabetes Autoantigen Insulin B-chain (9-23) Peptide," Diabetes, Jul. 2002, vol. 51, No. 7, pp. 2126-2134.

Baeshen N. A, et al., "Cell Factories for Insulin Production," Microbial Cell Factories, 2014, vol. 13, No. 141, pp. 1-9.

Bruggemann M, et al., "The Immunogenicity of Chimeric Antibodies," Journal of Experimental Medicine, 1989, vol. 170, pp. 2153-2157.

Dumont J, et al., "Human Cell Lines for Biopharmaceutical Manufacturing: History, Status, and Future Perspectives," Critical Reviews in Biotechnology, 2016, vol. 36, No. 6, pp. 1110-1122.

Fan L, et al., "Improving the Efficiency of Cho Cell Line Generation Using Glutamine Synthetase Gene Knockout Cells," Biotechnology and Bioengineering, Apr. 2012, vol. 109, No. 4, pp. 1007-1015.

Horvath S. J, et al., "An Automated DNA Synthesizer Employing Deoxynucleoside 3'-phosphoramidites," Methods in Enzymology, 1987, vol. 154, pp. 314-326.

Hua Q. X, et al., "Design of an Active Ultrastable Single-chain Insulin Analog," Journal of Biological Chemistry, May 23, 2008, vol. 283 No. 21, pp. 14703-14716.

(Continued)

*Primary Examiner* — Sudhakar Katakam
*Assistant Examiner* — Zachary J Miknis
(74) *Attorney, Agent, or Firm* — DLA Piper LLP (US)

(57) ABSTRACT

The present disclosure relates to compositions of insulin-Fc fusion proteins and their use to treat feline diabetes.

10 Claims, 11 Drawing Sheets

Specification includes a Sequence Listing.

(56) References Cited

FOREIGN PATENT DOCUMENTS

| | | |
|---|---|---|
| WO | WO-2010117760 A2 | 10/2010 |
| WO | WO-2016044676 A2 | 3/2016 |
| WO | WO-2016119023 A1 | 8/2016 |
| WO | WO-2016177771 A1 | 11/2016 |
| WO | WO-2016178905 A1 | 11/2016 |
| WO | WO-2018009921 A1 | 1/2018 |
| WO | WO-2018073185 A1 | 4/2018 |
| WO | WO-2018107117 A1 | 6/2018 |
| WO | WO-2019035010 A1 | 2/2019 |
| WO | WO-2019204206 A1 | 10/2019 |
| WO | WO-2020006529 A1 | 1/2020 |
| WO | WO-2020070276 A1 | 4/2020 |
| WO | WO-2020106748 A1 | 5/2020 |
| WO | WO-2020236762 A2 | 11/2020 |
| WO | WO-2021011827 A1 | 1/2021 |
| WO | WO-2021022149 A1 | 2/2021 |
| WO | WO-2021126584 A1 | 6/2021 |

OTHER PUBLICATIONS

Huang T. J, et al., " Production of Recombinant Murine-human Chimeric IgM and IgG Anti-Jsb for Use in the Clinical Laboratory, " Transfusion, Jun. 2003, vol. 43, pp. 758-764.

International Search Report and Written Opinion in corresponding PCT/US2019/040010, dated Nov. 12, 2019, 12 Pages.

Kim T. K, et al., "Mammalian Cell Transfection: the Present and the Future, " Analytical and Bioanalytical Chemistry, 2010, vol. 397, pp. 3173-3178.

Lodish, et al., Molecular Cell Biology, Molecular Cell Biology, 4th edition, 2000, www.ncbi.nlm.gov/ books/NBK21654 (abstract attached).

Office Action from co-pending U.S. Appl. No. 17/244,097, dated Jul. 1, 2021.

Office Action in corresponding U.S. Appl. No. 17/135,333, dated Apr. 16, 2021.

Office Action in corresponding U.S. Appl. No. 17/135,333, dated Jul. 12, 2021.

Office Action in corresponding U.S. Appl. No. 17/226,847, dated Jul. 12, 2021.

Singh R., et al., "Combined Blockade of HER2 And VEGF exerts greater Growth Inhibition of HER2-Overexpressing Gastric Cancer Xenografts Than Individual Blockade, "Experimental and Molecular Medicine, 2013, vol. 45, 11 pages.

Strietzel C.J., et al., "In Vitro Functional Characterization of Feline IgGs, "Veterinary Immunology and Immunopathology, 2014, vol. 158, pp. 214-223.

Tang L, et al., "Cloning and Characterization of cDNAs Encoding Four Different Canine Immunoglobulin Gamma Chains, "Veterinary Immunology and Immunopathology, 2001, vol. 80, pp. 259-270.

Terada T, et al., "A Chimeric Human-cat Fcgamma-fel D1 Fusion Protein Inhibits Systemic, Pulmonary, and Cutaneous Allergic Reactivity to Intratracheal Challenge in Mice Sensitized to Fel D1, the Major Cat Allergen, "Clinical Immunology, 2006, vol. 120, No. 1, pp. 45-56.

Walter M, et al., "No Effect of the Altered Peptide Ligand NBI-6024 on Beta-cell Residual Function and Insulin Needs in New-onset Type 1 Diabetes," Diabetes Care, 2009, vol. 32, No. 11, pp. 2036-2040.

Wang X., et al., "IgG Fc Engineering to Modulate Antibody Effector Functions," Protein Cell, 2018, vol. 9, No. 1, pp. 63-73.

Wang Y., et al., "Proinsulin-Transferrin Fusion Protein as a Novel Long-Acting Insulin Analog for the Inhibition of Hepatic Glucose," Diabetes, 2014, vol. 63, No. 5, pp. 1779-1788.

Yourgenome.org, "What does DNA do?," https://www.yourgenome.org/facts/what-does-dna-do. 2016, 3 page.

\* cited by examiner

```
SEQ ID NO: 22    FVNQHLCGSDLVEALALVCGERGFFYTDPTGG-GPRRGIVEQCCHSICSLYQLENYCNGG     59
SEQ ID NO: 23    FVNQHLCGSDLVEALYLVCGERGFFYTDPTGG-GPRRGIVEQCCHSICSLYQLENYCNGG     59
SEQ ID NO: 24    FVNQHLCGSHLVEALYLVCGERGFFYTPKAGG-GPRRGIVEQCCTSICSLYQLENYCNGG     59
SEQ ID NO: 25    FVNQHLCGSHLVEALYLVCGERGFFYTPKAAAAAAAKGIVEQCCTSICSLYQLENYCNGG     60
                 *********.***** ***********    :..  .:******* **************

SEQ ID NO: 22    GGAGGGGRCTDTPPCPVPEPLGGPSVLIFPPKPKDILRITRTPEVTCVVLDLGREDPEVQ    119
SEQ ID NO: 23    GGSGGGGRCTDTPPCPVPEPLGGPSVLIFPPKPKDILRITRTPEVTCVVLDLGREDPEVQ    119
SEQ ID NO: 24    GGSGGGGRCTDTPPCPVPEPLGGPSVLIFPPKPKDILRITRTPEVTCVVLDLGREDPEVQ    119
SEQ ID NO: 25    GGSGGGGRCTDTPPCPVPEPLGGPSVLIFPPKPKDILRITRTPEVTCVVLDLGREDPEVQ    120
                 **:*********************************************************

SEQ ID NO: 22    ISWFVDGKEVHTAKTQSREQQFNGTYRVVSVLPIEHQDWLTGKEFKCRVNHIDLPSPIER    179
SEQ ID NO: 23    ISWFVDGKEVHTAKTQSREQQFNGTYRVVSVLPIEHQDWLTGKEFKCRVNHIDLPSPIER    179
SEQ ID NO: 24    ISWFVDGKEVHTAKTQSREQQFNGTYRVVSVLPIEHQDWLTGKEFKCRVNHIDLPSPIER    179
SEQ ID NO: 25    ISWFVDGKEVHTAKTQSREQQFNGTYRVVSVLPIEHQDWLTGKEFKCRVNHIDLPSPIER    180
                 ************************************************************

SEQ ID NO: 22    TISKARGRAHKPSVYVLPPSPKELSSSDTVSITCLIKDFYPPDIDVEWQSNGQQEPERKH    239
SEQ ID NO: 23    TISKARGRAHKPSVYVLPPSPKELSSSDTVSITCLIKDFYPPDIDVEWQSNGQQEPERKH    239
SEQ ID NO: 24    TISKARGRAHKPSVYVLPPSPKELSSSDTVSITCLIKDFYPPDIDVEWQSNGQQEPERKH    239
SEQ ID NO: 25    TISKARGRAHKPSVYVLPPSPKELSSSDTVSITCLIKDFYPPDIDVEWQSNGQQEPERKH    240
                 ************************************************************

SEQ ID NO: 22    RMTPPQLDEDGSYFLYSKLSVDKSRWQQGDPFTCAVMHETLQNHYTDLSLSHSPG    294
SEQ ID NO: 23    RMTPPQLDEDGSYFLYSKLSVDKSRWQQGDPFTCAVMHETLQNHYTDLSLSHSPG    294
SEQ ID NO: 24    RMTPPQLDEDGSYFLYSKLSVDKSRWQQGDPFTCAVMHETLQNHYTDLSLSHSPG    294
SEQ ID NO: 25    RMTPPQLDEDGSYFLYSKLSVDKSRWQQGDPFTCAVMHETLQNHYTDLSLSHSPG    295
```

FIG. 3

SEQ ID NO: 32    FVNQHLCGSDLVEALYLVCGERGFFYTDPTGGGPRRGIVEQCCHSICSLYQLENYCNGGG    60
SEQ ID NO: 34    FVNQHLCGSDLVEALYLVCGERGFFYTDPTGGGPRRGIVEQCCHSICSLYQLENYCNGGG    60
SEQ ID NO: 36    FVNQHLCGSDLVEALYLVCGERGFFYTDPTGGGPRRGIVEQCCHSICSLYQLENYCNGGG    60
                 ************************************************************

SEQ ID NO: 32    GSGGGGGEGPKCPVPEIPGAPSVFIFPPKPKDTLSISRTPEVTCLVVDLGPDDSNVQITW    120
SEQ ID NO: 34    GSGGGGGEGPKCPVPEIPGAPSVFIFPPKPKDTLSISRTPEVTCLVVDLGPDDSNVQITW    120
SEQ ID NO: 36    GSGGGGGEGPKCPVPEIPGAPSVFIFPPKPKDTLSISRTPEVTCLVVDLGPDDSNVQITW    120
                 ************************************************************

SEQ ID NO: 32    FVDNTEMHTAKTRPREEQFNSTYRVVSVLPILHQDWLKGKEFKCKVNSKSLPSAMERTIS    180
SEQ ID NO: 34    FVDNTEMHTAKTRPREEQFSSTYRVVSVLPILHQDWLKGKEFKCKVNSKSLPSAMERTIS    180
SEQ ID NO: 36    FVDNTEMHTAKTRPREEQFKSTYRVVSVLPILHQDWLKGKEFKCKVNSKSLPSAMERTIS    180
                 *****************.**************************************

SEQ ID NO: 32    KAKGQPHEPQVYVLPPTQEELSENKVSVTCLIKGFHPPDIAVEWEITGQPEPENNYQTTP    240
SEQ ID NO: 34    KAKGQPHEPQVYVLPPTQEELSENKVSVTCLIKGFHPPDIAVEWEITGQPEPENNYQTTP    240
SEQ ID NO: 36    KAKGQPHEPQVYVLPPTQEELSENKVSVTCLIKGFHPPDIAVEWEITGQPEPENNYQTTP    240
                 ************************************************************

SEQ ID NO: 32    PQLDSDGTYFLYSRLSVDRSHWQRGNTYTCSVSHEALHSHHTQKSLTQSPG          291
SEQ ID NO: 34    PQLDSDGTYFLYSRLSVDRSHWQRGNTYTCSVSHEALHSHHTQKSLTQSPG          291
SEQ ID NO: 36    PQLDSDGTYFLYSRLSVDRSHWQRGNTYTCSVSHEALHSHHTQKSLTQSPG          291
                 ***************************************************

FIG. 4

```
                        SEQUENCE LISTING

Sequence total quantity: 39
SEQ ID NO: 1            moltype = AA  length = 30
FEATURE                 Location/Qualifiers
REGION                  1..30
                        note = B-chain
source                  1..30
                        mol_type = protein
                        organism = Homo sapiens
SEQUENCE: 1
FVNQHLCGSH LVEALYLVCG ERGFFYTPKT                                   30

SEQ ID NO: 2            moltype = AA  length = 21
FEATURE                 Location/Qualifiers
REGION                  1..21
                        note = A-chain
source                  1..21
                        mol_type = protein
                        organism = Homo sapiens
SEQUENCE: 2
GIVEQCCTSI CSLYQLENYC N                                            21

SEQ ID NO: 3            moltype = AA  length = 86
FEATURE                 Location/Qualifiers
REGION                  1..86
                        note = ProInsulin
source                  1..86
                        mol_type = protein
                        organism = Homo sapiens
SEQUENCE: 3
FVNQHLCGSH LVEALYLVCG ERGFFYTPKT RREAEDLQVG QVELGGGPGA GSLQPLALEG   60
SLQKRGIVEQ CCTSICSLYQ LENYCN                                       86

SEQ ID NO: 4            moltype = AA  length = 57
FEATURE                 Location/Qualifiers
REGION                  1..57
                        note = Synthetic Insulin Polypeptide
source                  1..57
                        mol_type = protein
                        organism = synthetic construct
SEQUENCE: 4
FVNQHLCGSD LVEALYLVCG ERGFFYTDPT GGGPRRGIVE QCCHSICSLY QLENYCN      57

SEQ ID NO: 5            moltype = AA  length = 57
FEATURE                 Location/Qualifiers
REGION                  1..57
                        note = Synthetic Insulin Polypeptide
source                  1..57
                        mol_type = protein
                        organism = synthetic construct
SEQUENCE: 5
FVNQHLCGSD LVEALALVCG ERGFFYTDPT GGGPRRGIVE QCCHSICSLY QLENYCN      57

SEQ ID NO: 6            moltype = AA  length = 58
FEATURE                 Location/Qualifiers
REGION                  1..58
                        note = Synthetic Insulin Polypeptide
source                  1..58
                        mol_type = protein
                        organism = synthetic construct
SEQUENCE: 6
FVNQHLCGSH LVEALYLVCG ERGFFYTPKA AAAAAAKGIV EQCCTSICSL YQLENYCN     58

SEQ ID NO: 7            moltype = AA  length = 57
```

```
FEATURE                     Location/Qualifiers
REGION                      1..57
                            note = Synthetic Insulin Polypeptide
source                      1..57
                            mol_type = protein
                            organism = synthetic construct
SEQUENCE: 7
FVNQHLCGSH LVEALYLVCG ERGFFYTPKA GGGPRRGIVE QCCTSICSLY QLENYCN      57

SEQ ID NO: 8                moltype = AA  length = 6
FEATURE                     Location/Qualifiers
REGION                      1..6
                            note = Synthetic C-chain
source                      1..6
                            mol_type = protein
                            organism = synthetic construct
SEQUENCE: 8
GGGPRR                                                              6

SEQ ID NO: 9                moltype = AA  length = 9
FEATURE                     Location/Qualifiers
REGION                      1..9
                            note = Synthetic Linker
source                      1..9
                            mol_type = protein
                            organism = synthetic construct
SEQUENCE: 9
GGGGAGGGG                                                           9

SEQ ID NO: 10               moltype = AA  length = 9
FEATURE                     Location/Qualifiers
REGION                      1..9
                            note = Synthetic Linker
source                      1..9
                            mol_type = protein
                            organism = synthetic construct
SEQUENCE: 10
GGGGSGGGG                                                           9

SEQ ID NO: 11               moltype = AA  length = 228
FEATURE                     Location/Qualifiers
source                      1..228
                            mol_type = protein
                            organism = Canis sp.
SEQUENCE: 11
RCTDTPPCPV PEPLGGPSVL IFPPKPKDIL RITRTPEVTC VVLDLGREDP EVQISWFVDG   60
KEVHTAKTQS REQQFNGTYR VVSVLPIEHQ DWLTGKEFKC RVNHIDLPSP IERTISKARG   120
RAHKPSVYVL PPSPKELSSS DTVSITCLIK DFYPPDIDVE WQSNGQQEPE RKHRMTPPQL   180
DEDGSYFLYS KLSVDKSRWQ QGDPFTCAVM HETLQNHYTD LSLSHSPG               228

SEQ ID NO: 12               moltype = AA  length = 224
FEATURE                     Location/Qualifiers
source                      1..224
                            mol_type = protein
                            organism = Canis sp.
SEQUENCE: 12
DCPKCPAPEM LGGPSVFIFP PKPKDTLLIA RTPEVTCVVV DLDPEDPEVQ ISWFVDGKQM   60
QTAKTQPREE QFNGTYRVVS VLPIGHQDWL KGKQFTCKVN NKALPSPIER TISKARGQAH   120
QPSVYVLPPS REELSKNTVS LTCLIKDFPP PDIDVEWQSN GQQEPESKYR TTPPQLDEDG   180
SYFLYSKLSV DKSRWQRGDT FICAVMHEAL HNHYTQESLS HSPG                   224

SEQ ID NO: 13               moltype = AA  length = 225
FEATURE                     Location/Qualifiers
source                      1..225
                            mol_type = protein
                            organism = Canis sp.
SEQUENCE: 13
CNNCPCPGCG LLGGPSVFIF PPKPKDILVT ARTPTVTCVV VDLDPENPEV QISWFVDSKQ   60
VQTANTQPRE EQSNGTYRVV SVLPIGHQDW LSGKQFKCKV NNKALPSPIE EIISKTPGQA   120
HQPNVYVLPP SRDEMSKNTV TLTCLVKDFF PPEIDVEWQS NGQQEPESKY RMTPPQLDED   180
GSYFLYSKLS VDKSRWQRGD TFICAVMHEA LHNHYTQISL SHSPG                  225

SEQ ID NO: 14               moltype = AA  length = 225
FEATURE                     Location/Qualifiers
source                      1..225
                            mol_type = protein
                            organism = Canis sp.
SEQUENCE: 14
CISPCPVPES LGGPSVFIFP PKPKDILRIT RTPEITCVVL DLGREDPEVQ ISWFVDGKEV   60
```

```
HTAKTQPREQ QFNSTYRVVS VLPIEHQDWL TGKEFKCRVN HIGLPSPIER TISKARGQAH   120
QPSVYVLPPS PKELSSSDTV TLTCLIKDFF PPEIDVEWQS NGQPEPESKY HTTAPQLDED   180
GSYFLYSKLS VDKSRWQQGD TFTCAVMHEA LQNHYTDLSL SHSPG                   225

SEQ ID NO: 15           moltype = AA  length = 224
FEATURE                 Location/Qualifiers
REGION                  1..224
                        note = Synthetic Fc Fragment
source                  1..224
                        mol_type = protein
                        organism = synthetic construct
SEQUENCE: 15
DCPKCPAPEM LGGPSVFIFP PKPKDTLLIA RTPEVTCVVV DLDPEDPEVQ ISWFVDGKQM   60
QTAKTQPREE QFSGTYRVVS VLPIGHQDWL KGKQFTCKVN NKALPSPIER TISKARGQAH   120
QPSVYVLPPS REELSKNTVS LTCLIKDFFP PDIDVEWQSN GQQEPESKYR TTPPQLDEDG   180
SYFLYSKLSV DKSRWQRGDT FICAVMHEAL HNHYTQESLS HSPG                    224

SEQ ID NO: 16           moltype = AA  length = 223
FEATURE                 Location/Qualifiers
REGION                  1..223
                        note = Synthetic Fc Fragment
source                  1..223
                        mol_type = protein
                        organism = synthetic construct
SEQUENCE: 16
CPKCPAPEML GGPSVFIFPP KPKDTLLIAR TPEVTCVVVD LDPEDPEVQI SWFVDGKQMQ   60
TAKTQPREEQ FKGTYRVVSV LPIGHQDWLK GKQFTCKVNN KALPSPIERT ISKARGQAHQ   120
PSVYVLPPSR EELSKNTVSL TCLIKDFFPP DIDVEWQSNG QQEPESKYRT TPPQLDEDGS   180
YFLYSKLSVD KSRWQRGDTF ICAVMHEALH NHYTQESLSH SPG                     223

SEQ ID NO: 17           moltype = AA  length = 224
FEATURE                 Location/Qualifiers
source                  1..224
                        mol_type = protein
                        organism = Felis catus
SEQUENCE: 17
DCPKCPPPEM LGGPSIFIFP PKPKDTLSIS RTPEVTCLVV DLGPDDSDVQ ITWFVDNTQV   60
YTAKTSPREE QFNSTYRVVS VLPILHQDWL KGKEFKCKVN SKSLPSPIER TISKAKGQPH   120
EPQVYVLPPA QEELSRNKVS VTCLIKSFHP PDIAVEWEIT GQPEPENNYR TTPPQLDSDG   180
TYFVYSKLSV DRSHWQRGNT YTCSVSHEAL HSHHTQKSLT QSPG                    224

SEQ ID NO: 18           moltype = AA  length = 224
FEATURE                 Location/Qualifiers
source                  1..224
                        mol_type = protein
                        organism = Felis catus
SEQUENCE: 18
DCPKCPPPEM LGGPSIFIFP PKPKDTLSIS RTPEVTCLVV DLGPDDSDVQ ITWFVDNTQV   60
YTAKTSPREE QFNSTYRVVS VLPILHQDWL KGKEFKCKVN SKSLPSPIER TISKDKGQPH   120
EPQVYVLPPA QEELSRNKVS VTCLIEGFYP SDIAVEWEIT GQPEPENNYR TTPPQLDSDG   180
TYFLYSRLSV DRSRWQRGNT YTCSVSHEAL HSHHTQKSLT QSPG                    224

SEQ ID NO: 19           moltype = AA  length = 225
FEATURE                 Location/Qualifiers
source                  1..225
                        mol_type = protein
                        organism = Felis catus
SEQUENCE: 19
GEGPKCPVPE IPGAPSVFIF PPKPKDTLSI SRTPEVTCLV VDLGPDDSNV QITWFVDNTE   60
MHTAKTRPRE EQFNSTYRVV SVLPILHQDW LKGKEFKCKV NSKSLPSAME RTISKAKGQP   120
HEPQVYVLPP TQEELSENKV SVTCLIKGPH PPDIAVEWEI TGQPEPENNY QTTPPQLDSD   180
GTYFLYSRLS VDRSHWQRGN TYTCSVSHEA LHSHHTQKSL TQSPG                   225

SEQ ID NO: 20           moltype = AA  length = 225
FEATURE                 Location/Qualifiers
REGION                  1..225
                        note = Synthetic Fc Fragment
source                  1..225
                        mol_type = protein
                        organism = synthetic construct
SEQUENCE: 20
GEGPKCPVPE IPGAPSVFIF PPKPKDTLSI SRTPEVTCLV VDLGPDDSNV QITWFVDNTE   60
MHTAKTRPRE EQFSSTYRVV SVLPILHQDW LKGKEFKCKV NSKSLPSAME RTISKAKGQP   120
HEPQVYVLPP TQEELSENKV SVTCLIKGFH PPDIAVEWEI TGQPEPENNY QTTPPQLDSD   180
GTYFLYSRLS VDRSHWQRGN TYTCSVSHEA LHSHHTQKSL TQSPG                   225

SEQ ID NO: 21           moltype = AA  length = 225
FEATURE                 Location/Qualifiers
REGION                  1..225
```

```
                        note = Synthetic Fc Fragment
source                  1..225
                        mol_type = protein
                        organism = synthetic construct
SEQUENCE: 21
GEGPKCPVPE IPGAPSVFIF PPKPKDTLSI SRTPEVTCLV VDLGPDDSNV QITWFVDNTE    60
MHTAKTRPRE EQFKSTYRVV SVLPILHQDW LKGKEFKCKV NSKSLPSAME RTISKAKGQP   120
HEPQVYVLPP TQEELSENKV SVTCLIKGFH PPDIAVEWEI TGQPEPENNY QTTPPQLDSD   180
GTYFLYSRLS VDRSHWQRGN TYTCSVSHEA LHSHHTQKSL TQSPG                   225

SEQ ID NO: 22           moltype = AA  length = 294
FEATURE                 Location/Qualifiers
REGION                  1..294
                        note = Synthetic Insulin-Fc Fusion Protein
source                  1..294
                        mol_type = protein
                        organism = synthetic construct
SEQUENCE: 22
FVNQHLCGSD LVEALALVCG ERGFFYTDPT GGGPRRGIVE QCCHSICSLY QLENYCNGGG    60
GAGGGGRCTD TPPCPVPEPL GGPSVLIFPP KPKDILRITR TPEVTCVVLD LGREDPEVQI   120
SWFVDGKEVH TAKTQSREQQ FNGTYRVVSV LPIEHQDWLT GKEFKCRVNH IDLPSPIERT   180
ISKARGRAHK PSVYVLPPSP KELSSSDTVS ITCLIKDFYP PDIDVEWQSN GQQEPERKHR   240
MTPPQLDEDG SYFLYSKLSV DKSRWQQGDP FTCAVMHETL QNHYTDLSLS HSPG         294

SEQ ID NO: 23           moltype = AA  length = 294
FEATURE                 Location/Qualifiers
REGION                  1..294
                        note = Synthetic Insulin-Fc Fusion Protein
source                  1..294
                        mol_type = protein
                        organism = synthetic construct
SEQUENCE: 23
FVNQHLCGSD LVEALYLVCG ERGFFYTDPT GGGPRRGIVE QCCHSICSLY QLENYCNGGG    60
GSGGGGRCTD TPPCPVPEPL GGPSVLIFPP KPKDILRITR TPEVTCVVLD LGREDPEVQI   120
SWFVDGKEVH TAKTQSREQQ FNGTYRVVSV LPIEHQDWLT GKEFKCRVNH IDLPSPIERT   180
ISKARGRAHK PSVYVLPPSP KELSSSDTVS ITCLIKDFYP PDIDVEWQSN GQQEPERKHR   240
MTPPQLDEDG SYFLYSKLSV DKSRWQQGDP FTCAVMHETL QNHYTDLSLS HSPG         294

SEQ ID NO: 24           moltype = AA  length = 294
FEATURE                 Location/Qualifiers
REGION                  1..294
                        note = Synthetic Insulin-Fc Fusion Protein
source                  1..294
                        mol_type = protein
                        organism = synthetic construct
SEQUENCE: 24
FVNQHLCGSH LVEALYLVCG ERGFFYTPKA GGGPRRGIVE QCCTSICSLY QLENYCNGGG    60
GSGGGGRCTD TPPCPVPEPL GGPSVLIFPP KPKDILRITR TPEVTCVVLD LGREDPEVQI   120
SWFVDGKEVH TAKTQSREQQ FNGTYRVVSV LPIEHQDWLT GKEFKCRVNH IDLPSPIERT   180
ISKARGRAHK PSVYVLPPSP KELSSSDTVS ITCLIKDFYP PDIDVEWQSN GQQEPERKHR   240
MTPPQLDEDG SYFLYSKLSV DKSRWQQGDP FTCAVMHETL QNHYTDLSLS HSPG         294

SEQ ID NO: 25           moltype = AA  length = 295
FEATURE                 Location/Qualifiers
REGION                  1..295
                        note = Synthetic Insulin-Fc Fusion Protein
source                  1..295
                        mol_type = protein
                        organism = synthetic construct
SEQUENCE: 25
FVNQHLCGSH LVEALYLVCG ERGFFYTPKA AAAAAKGIV EQCCTSICSL YQLENYCNGG     60
GGSGGGGRCT DTPPCPVPEP LGGPSVLIFP PKPKDILRIT RTPEVTCVVL DLGREDPEVQ   120
ISWFVDGKEV HTAKTQSREQ QFNGTYRVVS VLPIEHQDWL TGKEFKCRVN HIDLPSPIER   180
TISKARGRAH KPSVYVLPPS PKELSSSDTV SITCLIKDFY PPDIDVEWQS NGQQEPERKH   240
RMTPPQLDED GSYFLYSKLS VDKSRWQQGD PFTCAVMHET LQNHYTDLSL SHSPG        295

SEQ ID NO: 26           moltype = AA  length = 290
FEATURE                 Location/Qualifiers
REGION                  1..290
                        note = Synthetic Insulin-Fc Fusion Protein
source                  1..290
                        mol_type = protein
                        organism = synthetic construct
SEQUENCE: 26
FVNQHLCGSD LVEALALVCG ERGFFYTDPT GGGPRRGIVE QCCHSICSLY QLENYCNGGG    60
GAGGGGDCPK CPAPEMLGGP SVFIPPPKPK DTLLIARTPE VTCVVVDLDP EDPEVQISWF   120
VDGKQMQTAK TQPREEQFNG TYRVVSVLPI GHQDWLKGKQ FTCKVNNKAL PSPIERTISK   180
ARGQAHPSV YVLPPSREEL SKNTVSLTCL IKDFFPPDID VEWQSNGQQE PESKYRTTPP   240
QLDEDGSYFL YSKLSVDKSR WQRGDTFICA VMHEALHNHY TQESLSHSPG             290
```

```
SEQ ID NO: 27          moltype = AA  length = 291
FEATURE                Location/Qualifiers
REGION                 1..291
                       note = Synthetic Insulin-Fc Fusion Protein
source                 1..291
                       mol_type = protein
                       organism = synthetic construct
SEQUENCE: 27
FVNQHLCGSD LVEALALVCG ERGFFYTDPT GGGPRRGIVE QCCHSICSLY QLENYCNGGG    60
GAGGGGCNNC PCPGCGLLGG PSVFIFPPKP KDILVTARTP TVTCVVVDLD PENPEVQISW   120
FVDSKQVQTA NTQPREEQSN GTYRVVSVLP IGHQDWLSGK QFKCKVNNKA LPSPIEEIIS   180
KTPGQAHQPN VYVLPPSRDE MSKNTVTLTC LVKDFFPPEI DVEWQSNGQQ EPESKYRMTP   240
PQLDEDGSYF LYSKLSVDKS RWQRGDTFIC AVMHEALHNH YTQISLSHSP G            291

SEQ ID NO: 28          moltype = AA  length = 291
FEATURE                Location/Qualifiers
REGION                 1..291
                       note = Synthetic Insulin-Fc Fusion Protein
source                 1..291
                       mol_type = protein
                       organism = synthetic construct
SEQUENCE: 28
FVNQHLCGSD LVEALALVCG ERGFFYTDPT GGGPRRGIVE QCCHSICSLY QLENYCNGGG    60
GAGGGGCISP CPVPESLGGP SVFIFPPKPK DILRITRTPE ITCVVLDLGR EDPEVQISWF   120
VDGKEVHTAK TQPREQQFNS TYRVVSVLPI EHQDWLTGKE FKCRVNHIGL PSPIERTISK   180
ARGQAHQPSV YVLPPSPKEL SSSDTVTLTC LIKDFFPPEI DVEWQSNGQP EPESKYHTTA   240
PQLDEDGSYF LYSKLSVDKS RWQQGDTFTC AVMHEALQNH YTDLSLSHSP G            291

SEQ ID NO: 29          moltype = AA  length = 290
FEATURE                Location/Qualifiers
REGION                 1..290
                       note = Synthetic Insulin-Fc Fusion Protein
source                 1..290
                       mol_type = protein
                       organism = synthetic construct
SEQUENCE: 29
FVNQHLCGSD LVEALALVCG ERGFFYTDPT GGGPRRGIVE QCCHSICSLY QLENYCNGGG    60
GAGGGGDCPK CPAPEMLGGP SVFIFPPKPK DTLLIARTPE VTCVVVDLDP EDPEVQISWF   120
VDGKQMQTAK TQPREEQFSG TYRVVSVLPI GHQDWLKGKQ FTCKVNNKAL PSPIERTISK   180
ARGQAHQPSV YVLPPSREEL SKNTVSLTCL IKDFFPPDID VEWQSNGQQE PESKYRTTPP   240
QLDEDGSYFL YSKLSVDKSR WQRGDTFICA VMHEALHNHY TQESLSHSPG              290

SEQ ID NO: 30          moltype = AA  length = 290
FEATURE                Location/Qualifiers
REGION                 1..290
                       note = Synthetic Insulin-Fc Fusion Protein
source                 1..290
                       mol_type = protein
                       organism = synthetic construct
SEQUENCE: 30
FVNQHLCGSH LVEALALVCG ERGFFYTDPT GGGPRRGIVE QCCTSICSLY QLENYCNGGG    60
GAGGGGDCPK CPAPEMLGGP SVFIFPPKPK DTLLIARTPE VTCVVVDLDP EDPEVQISWF   120
VDGKQMQTAK TQPREEQFQG TYRVVSVLPI GHQDWLKGKQ FTCKVNNKAL PSPIERTISK   180
ARGQAHQPSV YVLPPSREEL SKNTVSLTCL IKDFFPPDID VEWQSNGQQE PESKYRTTPP   240
QLDEDGSYFL YSKLSVDKSR WQRGDTFICA VMHEALHNHY TQESLSHSPG              290

SEQ ID NO: 31          moltype = AA  length = 289
FEATURE                Location/Qualifiers
REGION                 1..289
                       note = Synthetic Insulin-Fc Fusion Protein
source                 1..289
                       mol_type = protein
                       organism = synthetic construct
SEQUENCE: 31
FVNQHLCGSD LVEALALVCG ERGFFYTDPT GGGPRRGIVE QCCHSICSLY QLENYCNGGG    60
GAGGGGCPKC PAPEMLGGPS VFIFPPKPKD TLLIARTPEV TCVVVDLPE DPEVQISWFV    120
DGKQMQTAKT QPREEQFKGT YRVVSVLPIG HQDWLKGKQF TCKVNNKALP SPIERTISKA   180
RGQAHQPSVY VLPPSREELS KNTVSLTCLI KDFFPPDIDV EWQSNGQQEP ESKYRTTPPQ   240
LDEDGSYFLY SKLSVDKSRW QRGDTFICAV MHEALHNHYT QESLSHSPG               289

SEQ ID NO: 32          moltype = AA  length = 291
FEATURE                Location/Qualifiers
REGION                 1..291
                       note = Synthetic Insulin-Fc Fusion Protein
source                 1..291
                       mol_type = protein
                       organism = synthetic construct
SEQUENCE: 32
```

```
FVNQHLCGSD LVEALYLVCG ERGFFYTDPT GGGPRRGIVE QCCHSICSLY QLENYCNGGG  60
GSGGGGGEGP KCPVPEIPGA PSVFIFPPKP KDTLSISRTP EVTCLVVDLG PDDSNVQITW 120
FVDNTEMHTA KTRPREEQFN STYRVVSVLP ILHQDWLKGK EFKCKVNSKS LPSAMERTIS 180
KAKGQPHEPQ VYVLPPTQEE LSENKVSVTC LIKGFHPPDI AVEWEITGQP EPENNYQTTP 240
PQLDSDGTYF LYSRLSVDRS HWQRGNTYTC SVSHEALHSH HTQKSLTQSP G         291

SEQ ID NO: 33              moltype = DNA   length = 933
FEATURE                    Location/Qualifiers
misc_feature               1..933
                           note = Synthetic cDNA for Insulin-Fc Fusion Protein
source                     1..933
                           mol_type = other DNA
                           organism = synthetic construct
SEQUENCE: 33
atggaatgga gctgggtctt tctcttcttc ctgtcagtaa cgactggtgt ccactccttc  60
gtgaaccagc acctgtgcgg ctccgacctg gtggaagctc tgtatctcgt gtgcggcgag 120
cggggcttct tctacaccga tcccactgga ggcggtccac gcagaggcat cgtgaacag 180
tgctgccact ccatctgctc cctgtaccag ctggaaaact actgcaatgg cggaggtggt 240
tcaggaggcg gtggaggtga gggccccaag tgccccgtgc cgagattcc cggtgccccc 300
agcgtgttca tctttccccc aaaacccaag gacaccctga gcatcagcag gaccccgag 360
gtgacctgcc tggtggtgga cctgggaccc gacgacagca acgtgcagat cacctggttc 420
gtggacaaca ccgagatgca caccgccaag accaggcctc gggaggagca gttcaacagc 480
acctacaggg tggtgagcgt gctgcccatc ctgcaccagg actggctgaa gggcaaggag 540
ttcaagtgca aggtgaacag caagagcctg cccagcgcca tggagaggac catcagcaag 600
gccaaggtgc agccccacga gccccaagtg tacgtgcttc cccgaccca ggaggagttg 660
agcgagaaca aagtgagcgt gacctgcctg atcaaggctc tccaccctcc cgacatcgcc 720
gtggagtggg agatcaccgg ccagcctgag ccggaaaata actaccagac caccctcca 780
cagctggaca gcgacggcac ctacttcctt tacagcaggc tgtctgtgga ccgaagccat 840
tggcaaaggg gcaacaccta cacctgcagc gtgagccacg aggctctgca cagccaccac 900
acccagaagt ctctgaccca gagccccgga tag                             933

SEQ ID NO: 34              moltype = AA   length = 291
FEATURE                    Location/Qualifiers
REGION                     1..291
                           note = Synthetic Insulin-Fc Fusion Protein
source                     1..291
                           mol_type = protein
                           organism = synthetic construct
SEQUENCE: 34
FVNQHLCGSD LVEALYLVCG ERGFFYTDPT GGGPRRGIVE QCCHSICSLY QLENYCNGGG  60
GSGGGGGEGP KCPVPEIPGA PSVFIFPPKP KDTLSISRTP EVTCLVVDLG PDDSNVQITW 120
FVDNTEMHTA KTRPREEQFS STYRVVSVLP ILHQDWLKGK EFKCKVNSKS LPSAMERTIS 180
KAKGQPHEPQ VYVLPPTQEE LSENKVSVTC LIKGFHPPDI AVEWEITGQP EPENNYQTTP 240
PQLDSDGTYF LYSRLSVDRS HWQRGNTYTC SVSHEALHSH HTQKSLTQSP G         291

SEQ ID NO: 35              moltype = DNA   length = 933
FEATURE                    Location/Qualifiers
misc_feature               1..933
                           note = Synthetic cDNA for Insulin-Fc Fusion Protein
source                     1..933
                           mol_type = other DNA
                           organism = synthetic construct
SEQUENCE: 35
atggaatgga gctgggtctt tctcttcttc ctgtcagtaa cgactggtgt ccactccttc  60
gtgaaccagc acctgtgcgg ctccgacctg gtggaagctc tgtatctcgt gtgcggcgag 120
cggggcttct tctacaccga tcccactgga ggcggtccac gcagaggcat cgtgaacag 180
tgctgccact ccatctgctc cctgtaccag ctggaaaact actgcaatgg cggaggtggt 240
tcaggaggcg gtggaggtga gggccccaag tgccccgtgc cgagattcc cggtgccccc 300
agcgtgttca tctttccccc aaaacccaag gacaccctga gcatcagcag gaccccgag 360
gtgacctgcc tggtggtgga cctgggaccc gacgacagca acgtgcagat cacctggttc 420
gtggacaaca ccgagatgca caccgccaag accaggcctc gggaggagca gttcagcagc 480
acctacaggg tggtgagcgt gctgcccatc ctgcaccagg actggctgaa gggcaaggag 540
ttcaagtgca aggtgaacag caagagcctg cccagcgcca tggagaggac catcagcaag 600
gccaaggtgc agccccacga gccccaagtg tacgtgcttc cccgaccca ggaggagttg 660
agcgagaaca aagtgagcgt gacctgcctg atcaagggct ccaccctcc cgacatcgcc 720
gtggagtggg agatcaccgg ccagcctgag ccggaaaata actaccagac caccctcca 780
cagctggaca gcgacggcac ctacttcctt tacagcaggc tgtctgtgga ccgaagccat 840
tggcaaaggg gcaacaccta cacctgcagc gtgagccacg aggctctgca cagccaccac 900
acccagaagt ctctgaccca gagccccgga tag                             933

SEQ ID NO: 36              moltype = AA   length = 291
FEATURE                    Location/Qualifiers
REGION                     1..291
                           note = Synthetic Insulin-Fc Fusion Protein
source                     1..291
                           mol_type = protein
                           organism = synthetic construct
SEQUENCE: 36
FVNQHLCGSD LVEALYLVCG ERGFFYTDPT GGGPRRGIVE QCCHSICSLY QLENYCNGGG  60
```

```
GSGGGGGEGP KCPVPEIPGA PSVFIFPPKP KDTLSISRTP EVTCLVVDLG PDDSNVQITW    120
FVDNTEMHTA KTRPREEQFK STYRVVSVLP ILHQDWLKGK EFKCKVNSKS LPSAMERTIS    180
KAKGQPHEPQ VYVLPPTQEE LSENKVSVTC LIKGFHPPDI AVEWEITGQP EPENNYQTTP    240
PQLDSDGTYF LYSRLSVDRS HWQRGNTYTC SVSHEALHSH HTQKSLTQSP G            291

SEQ ID NO: 37           moltype = DNA  length = 933
FEATURE                 Location/Qualifiers
misc_feature            1..933
                        note = Synthetic cDNA for Insulin-Fc Fusion Protein
source                  1..933
                        mol_type = other DNA
                        organism = synthetic construct
SEQUENCE: 37
atggaatgga gctgggtctt tctcttcttc ctgtcagtaa cgactggtgt ccactcctc     60
gtgaaccagc acctgtgcgg ctccgacctg gtggaagctc tgtatctcgt gtgcggcgag   120
cggggcttct tctacaccga tcccactgga ggcggtccac gcagaggcat cgtggaacag   180
tgctgccact ccatctgctc cctgtaccag ctggaaaact actgcaatgg cggaggtggt   240
tcaggaggcg gtggaggtga gggccccaag tgccccgtgc ccgagattcc cggtgcccc    300
agcgtgttca tctttccccc aaaacccaag gacaccctga gcatcagcag gaccccgag    360
gtgacctgcc tggtggtgga cctgggaccc gacgacagca acgtgcagat cacctggttc   420
gtggacaaca ccgagatgca caccgccaag accaggcctc gggaggagca gttcaagagc   480
acctacaggg tggtgagcgt gctgcccatc ctgcaccagg actggctgaa gggcaaggag   540
ttcaagtgca aggtgaacag caagagcctg cccagcgcca tggagaggac catcagcaag   600
gccaagggtc agccccacga gccccaagtg tacgtgcttc cccgacccag gaggagttg    660
agcgagaaca aagtgagcgt gacctgcctg atcaagggct ccaccctcc cgacatcgcc    720
gtggagtggg agatcaccgg ccagcctgag ccggaaaata actaccagac caccctcca    780
cagctggaca gcgacggcac ctacttcctt tacagcaggc tgtctgtgga ccgaagccat   840
tggcaaaggg gcaacaccta cacctgcagc gtgagccacg aggctctgca cagccaccac   900
acccagaagt ctctgaccca gagccccgga tag                                933

SEQ ID NO: 38           moltype = AA  length = 19
FEATURE                 Location/Qualifiers
REGION                  1..19
                        note = Synthetic Leader Sequence
source                  1..19
                        mol_type = protein
                        organism = synthetic construct
SEQUENCE: 38
MEWSWVFLFF LSVTTGVHS                                                 19

SEQ ID NO: 39           moltype = DNA  length = 57
FEATURE                 Location/Qualifiers
misc_feature            1..57
                        note = Synthetic Leader Sequence Nucleic Acid
source                  1..57
                        mol_type = other DNA
                        organism = synthetic construct
SEQUENCE: 39
atggaatgga gctgggtctt tctcttcttc ctgtcagtaa cgactggtgt ccactcc       57
```

ULTRA-LONG ACTING INSULIN-FC FUSION PROTEIN AND METHODS OF USE

CROSS-REFERENCE TO RELATED APPLICATIONS

The present application is a continuation of U.S. patent application Ser. No. 17/527,486, filed Nov. 16, 2021, now U.S. Pat. No. 11,814,418, issued Nov. 14, 2023, which is a continuation of U.S. patent application Ser. No. 17/226,847, filed Apr. 9, 2021, now U.S. Pat. No. 11,192,930, issued Dec. 7, 2021, which claims the priority benefit of U.S. Provisional Patent Application Ser. No. 63/008,520, filed Apr. 10, 2020. The contents of the aforementioned patent applications are hereby incorporated herein by reference in their entirety.

SEQUENCE LISTING

The following application contains a sequence listing submitted electronically as a Standard ST.26 compliant XML file entitled "SequenceListing031.xml," created on Dec. 15, 2023, as 56,423 bytes in size, the contents of which are incorporated herein.

TECHNICAL FIELD

The present technology relates to compositions of insulin-Fc fusion proteins and their use to treat diabetes in companion animals, e.g., cats.

BACKGROUND

The following description of the background of the present technology is provided simply as an aid in understanding the present technology and is not admitted to describe or constitute prior art to the present technology.

Diabetes is a chronic condition characterized by an insulin deficiency and/or ineffective use of insulin. Diabetics that have an absolute deficiency of insulin are categorized as having type 1 or insulin-dependent diabetes mellitus (IDDM). Type 1 diabetics are thought to have a genetic predisposition combined with immunologic destruction of the insulin-producing β-cells of the pancreas. In comparison, diabetics that have the capability to still produce some insulin but have a relative deficiency due to insulin resistance or other dysfunction, are classified as having type 2 or non-insulin-dependent diabetes mellitus (NIDDM). Type 2 increased insulin production or increased insulin resistance is linked to genetic predisposition, obesity, and certain medications.

When a cat does not produce insulin or cannot use it normally, the cat's blood sugar levels elevate, resulting in hyperglycemia. Diabetic cats can fall under the type 1 (IDDM) or type 2 (NIDDM) classification. Generally, cats initially develop type 2 diabetes mellitus (insulin resistance), but by the time the disease is usually diagnosed by a veterinarian, it has progressed to type 1 (inflammatory disease in pancreas with significant loss of beta cell mass), and the cat is dependent on exogenous insulin. Some diabetic cats can be managed with dietary changes and oral medication, but the majority of diabetic cats need to receive insulin to maintain adequate regulation. Left untreated, it can lead to weight loss, loss of appetite, vomiting, dehydration, problems with motor function, coma, and even death. Cats that fall under the type 1 classification need daily shots to replace the missing insulin, but cats falling under the type 2 classification also stand to benefit from improved glycemic control through administration of additional exogenous insulin to help overcome their resistance to insulin.

Approximately 0.5% of cats in the United States have diabetes. Current diabetes therapies for cats include the use of insulin, such as ProZinc® (Boehringer Ingelheim Vetmedica, Duluth, Georgia) which is administered once or twice daily. The burden of frequent injections on owners often results in a lack of treatment regimen compliance and under dosing, leading to poor long-term health outcomes. In fact, the significant costs of insulin therapy and the practicality of dosing their pets up to 14 times per week leads to a significant percentage of owners to select euthanasia for their pets as an alternative to intensive management of diabetes. Therefore, there is a need for cost effective and less burdensome treatment options for this disease.

SUMMARY OF THE PRESENT TECHNOLOGY

In an aspect, the present disclosure provides a fusion protein comprising an insulin polypeptide and an Fc fragment, wherein the insulin polypeptide and the Fc fragment are connected by a linker such as a peptide linker, wherein the Fc fragment comprises the sequence:

```
                                      (SEQ ID NO: 21)
GEGPKCPVPEIPGAPSVFIFPPKPKDTLSISRTPEVTCLVVDLGPDDSN

VQITWFVDNTEMHTAKTRPREEQFKSTYRVVSVLPILHQDWLKGKEFKC

KVNSKSLPSAMERTISKAKGQPHEPQVYVLPPTQEELSENKVSVTCLIK

GFHPPDIAVEWEITGQPEPENNYQTTPPQLDSDGTYFLYSRLSVDRSHW

QRGNTYTCSVSHEALHSHHTQKSLTQSPG.
```

In one embodiment, the present disclosure provides a fusion protein comprising an insulin polypeptide and an Fc fragment, wherein the insulin polypeptide and the Fc fragment are connected by a linker (e.g., peptide linker) comprising the sequence

```
              (SEQ ID NO: 10)
       GGGGSGGGG.
```

In an embodiment, the present disclosure provides for a fusion protein comprising an insulin polypeptide and an Fc fragment, wherein the insulin polypeptide and the Fc fragment are connected by a linker (e.g., peptide linker), and wherein the fusion protein comprises the sequence

```
                                      (SEQ ID NO: 36)
FVNQHLCGSDLVEALYLVCGERGFFYTDPTGGGPRRGIVEQCCHSICSL

YQLENYCNGGGGSGGGGGEGPKCPVPEIPGAPSVFIFPPKPKDTLSISR

TPEVTCLVVDLGPDDSNVQITWFVDNTEMHTAKTRPREEQFKSTYRVVS

VLPILHQDWLKGKEFKCKVNSKSLPSAMERTISKAKGQPHEPQVYVLPP

TQEELSENKVSVTCLIKGFHPPDIAVEWEITGQPEPENNYQTTPPQLDS

DGTYFLYSRLSVDRSHWQRGNTYTCSVSHEALHSHHTQKSLTQSPG.
```

In embodiments, a fusion protein of the present disclosure comprises a dimer, wherein the dimer comprises two identical monomers bound together via disulfide bonds e.g., the fusion protein is a homodimer. In embodiments, the percentage homodimer of insulin-Fc fusion protein is greater than or equal to 90%.

In embodiments, the fusion proteins described herein are made using HEK293 cells, and the resulting homodimer titer after purification using Protein A beads or a Protein A column is greater than 40 mg/L. In embodiments, the insulin receptor IC50 for the fusion proteins described herein is less than or equal to 5000 nM. In embodiments, the serum half-life of the fusion proteins described herein in the blood or serum of a target animal upon administration is longer than about 3 days. For the fusion proteins described herein, the time during which there is a statistically significant decrease in blood glucose level in a subject relative to a pre-dose level is longer than one of 2 hours, 6 hours, 9 hours, 12 hours, 18 hours, 1 day, 1.5 days, 2 days, 2.5 days, 3 days, 4 days, 5 days, 6 days, 7 days or longer.

In aspects, for the fusion proteins described herein, the NAOC after the first subcutaneous injection at a dose between 0.025 and 0.5 mg/kg/week in a target animal is greater than 150% FBGL days kg/mg. In embodiments, for the fusion proteins described herein, the ratio of the NAOC after the third weekly subcutaneous injection of the fusion proteins in the target animal to the NAOC after the first subcutaneous injection of the fusion protein in the target animal is greater than 0.50.

In aspects, fusion proteins as described herein are formulated as a pharmaceutical composition. In embodiments, in the pharmaceutical composition the fusion protein is present at a concentration of about 3 mg/mL or greater. In embodiments, the composition is suitable for subcutaneous administration.

In aspects, a method is described for lowering the blood glucose level of a cat, the method comprising administering a physiologically effective amount of a fusion protein as described herein or a pharmaceutical composition thereof to the cat. In embodiments, the cat is diagnosed with diabetes. In some embodiments, the fusion protein is administered subcutaneously. In some embodiments, the fusion protein is administered daily, twice weekly, or once weekly to the cat. In examples, the fusion protein is administered once weekly to the cat at a dose between 0.025 and 0.5 mg/kg/week. In aspects, a cell engineered to express a fusion protein as described herein. In examples, the cell is transfected with a nucleic acid encoding the fusion protein. In examples, the cell is a HEK293 cell or a CHO cell.

In an aspect, a cDNA encoding a fusion protein as described herein is described. In embodiments, the cDNA comprises the nucleic acid sequence encoding the insulin-Fc fusion protein of SEQ ID NO: 36 where the leader sequence is in bold:

```
                                             (SEQ ID NO: 37)
ATGGAATGGAGCTGGGTCTTTCTCTTCTTCCTGTCAGTAACGACTGGTGT

CCACTCCTTCGTGAACCAGCACCTGTGCGGCTCCGACCTGGTGGAAGCTC

TGTATCTCGTGTGCGGCGAGCGGGGCTTCTTCTACACCGATCCCACTGGA

GGCGGTCCACGCAGAGGCATCGTGGAACAGTGCTGCCACTCCATCTGCTC

CCTGTACCAGCTGGAAAACTACTGCAATGGCGGAGGTGGTTCAGGAGGCG

GTGGAGGTGAGGGCCCCAAGTGCCCCGTGCCCGAGATTCCCGGTGCCCCC

AGCGTGTTCATCTTTCCCCCAAAACCCAAGGACACCCTGAGCATCAGCAG

GACCCCCGAGGTGACCTGCCTGGTGGTGGACCTGGGACCCGACGACAGCA

ACGTGCAGATCACCTGGTTCGTGGACAACACCGAGATGCACACCGCCAAG

ACCAGGCCTCGGGAGGAGCAGTTCAAGAGCACCTACAGGGTGGTGAGCGT

GCTGCCCATCCTGCACCAGGACTGGCTGAAGGGCAAGGAGTTCAAGTGCA

AGGTGAACAGCAAGAGCCTGCCCAGCGCCATGGAGAGGACCATCAGCAAG

GCCAAGGGTCAGCCCCACGAGCCCCAAGTGTACGTGCTTCCCCCGACCCA

GGAGGAGTTGAGCGAGAACAAAGTGAGCGTGACCTGCCTGATCAAGGGCT

TCCACCCTCCCGACATCGCCGTGGAGTGGGAGATCACCGGCCAGCCTGAG

CCGGAAAATAACTACCAGACCACCCCTCCACAGCTGGACAGCGACGGCAC

CTACTTCCTTTACAGCAGGCTGTCTGTGGACCGAAGCCATTGGCAAAGGG

GCAACACCTACACCTGCAGCGTGAGCCACGAGGCTCTGCACAGCCACCAC

ACCCAGAAGTCTCTGACCCAGAGCCCCGGATAG.
```

BRIEF DESCRIPTION OF THE DRAWINGS

FIG. 3 illustrates a side-by-side sequence comparison of SEQ ID NO: 22, SEQ ID NO: 23, SEQ ID NO: 24 and SEQ ID NO: 25. "*" represents complete homology across all sequences at a given sequence position, while ":", "." or spaces refer to conservative, moderate, or very different amino acid mutations across the sequences at a given sequence position, respectively.

FIG. 4 illustrates a side-by-side sequence comparison of SEQ ID NO: 32, SEQ ID NO: 34, and SEQ ID NO: 36. "*" represents complete homology across all sequences at a given sequence position, while ":", "." or spaces refer to conservative, moderate, or very different amino acid mutations across the sequences at a given sequence position, respectively.

DETAILED DESCRIPTION

Figure 1:
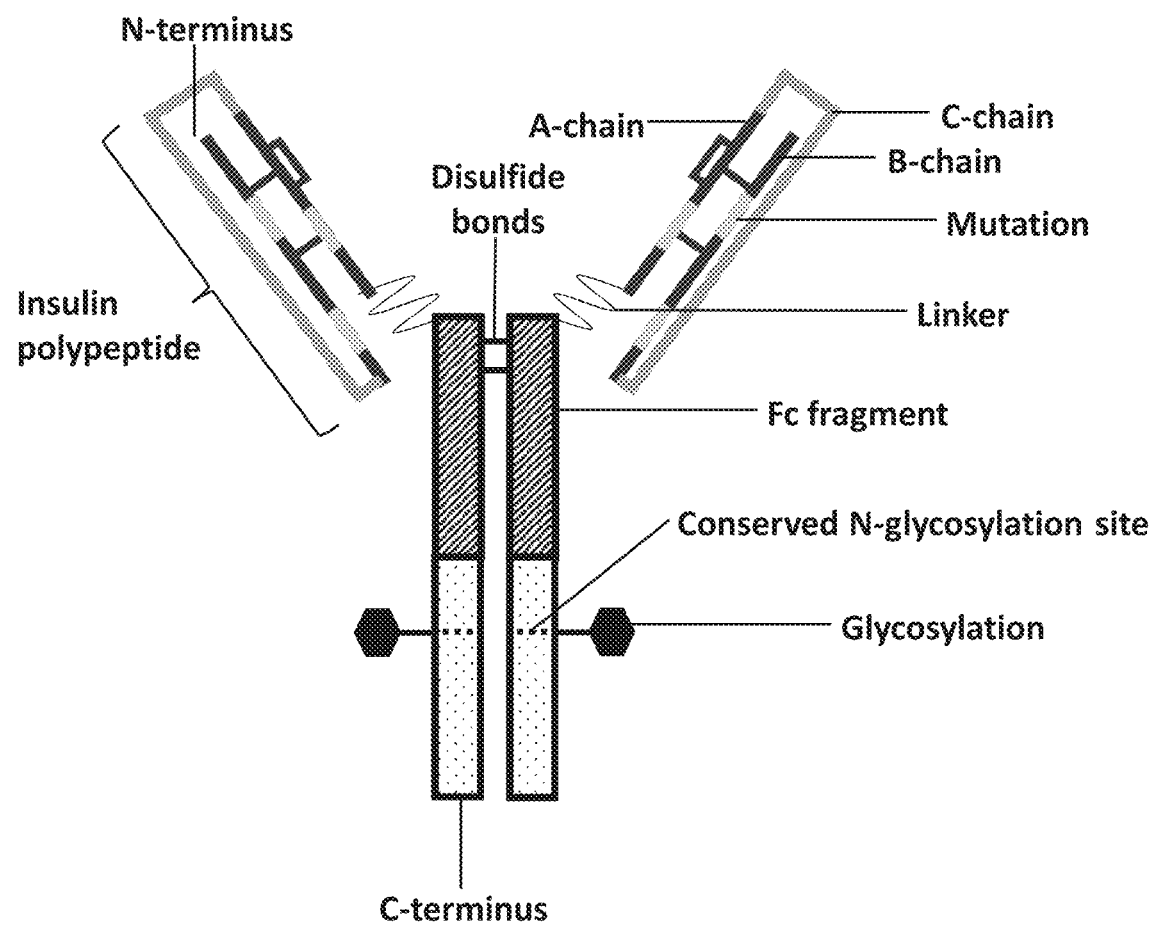
FIG. 1 shows a schematic representation of an exemplary insulin-Fc fusion protein homodimer.

An insulin treatment that requires less frequent dosing (e.g., once-weekly injections) would be less burdensome on the owners, leading to better compliance, fewer instances of euthanasia, and better outcomes for the pets. As disclosed herein, proposed ultra-long acting insulin treatments for veterinary clinical use comprise an insulin-Fc fusion protein making use of an Fc fragment to prolong their action in vivo. An insulin-Fc fusion protein suitable for an ultra-long acting treatment for diabetes should meet various design goals. An insulin-Fc fusion protein configuration suitable for an ultra-long acting treatment for diabetes in cats should be manufacturable in mammalian cells, for example human embryonic kidney (HEK, e.g., HEK293) cells, with an acceptable titer of the desired homodimer product (e.g., greater than 40 mg/L homodimer titer from transiently transfected HEK cells, greater than 75 mg/L from transiently transfected HEK cells, greater than 100 mg/L from transiently transfected HEK cells, etc.). Only candidates with a homodimer titer of greater than 40 mg/L from transiently transfected HEK cells are considered useful in the present invention, because experience has demonstrated that homodimer titers less than this level will not likely result in commercial production homodimer titers in Chinese hamster ovary (CHO) cells that meet the stringently low manufacturing cost requirements for veterinary products.

In addition, the molecule must bind the insulin receptor with an appreciable affinity (e.g., IC50 less than 5000 nM, IC50 less than 4000 nM, IC50 less than 3000 nM, IC50 less than 2500 nM, etc.) as measured in the 4° C. IM-9 insulin receptor binding assay. Based on experience, only molecules exhibiting insulin receptor activity IC50 values less than 5000 nM are deemed likely to exhibit the requisite bioactivity in the target species. The molecule must also demonstrate sustained bioactivity in vivo (e.g., demonstrate glucose lowering activity greater than about 2 hours, 6 hours, 9 hours, 12 hours, 18 hours, 1 day, 1.5 days, 2 days, 2.5 days, 3 days, 4 days, 5 days, 6 days, 7 days, or longer) to justify less frequent dosing. The molecule must also demonstrate prolonged system residence time in the target animal (e.g., the serum half-life must be greater than 3 days, or longer). The bioactive potency and duration of the bioactivity may be quantitatively represented by calculating the area over the percent fasting blood glucose (% FBGL) curve normalized to a given dose in mg/kg (NAOC) with units of % FBGL·days·kg/mg as described in Example 15. The NAOC increases with a greater drop in % FBGL, which is the case where the molecule demonstrates increased bioactivity, and when the % FBGL takes longer to return to 100%, which is the case where the insulin-Fc fusion protein demonstrates increased duration of action. To be useful as described herein, a molecule must demonstrate a sufficiently high NAOC value (e.g., preferably NAOC greater than 150% FBGL days kg/mg, more preferably NAOC greater than 200% FBGL·days·kg/mg, and even more preferably NAOC greater than 250% FBGL days kg/mg). Based on experience, at NAOC values greater than 150% FBGL·days·kg/mg, the dose requirements in the target species will be sufficiently low to reach an acceptable treatment cost.

There are insulin-Fc fusion proteins known that make use of a human Fc region to prolong their action in vivo. However, insulin-Fc fusion proteins with a human Fc, when used in cats, develop antibodies that neutralize their action. Replacing a human Fc with a feline IgG Fc isotype would help to prevent unwanted immunogenicity which could result in the creation of neutralizing anti-drug antibodies.

There are three feline Fc isotypes: IgG1a (SEQ ID NO: 17), IgG1b (SEQ ID NO: 18), and IgG2 (SEQ ID NO: 19) as shown below.

```
                                             (SEQ ID NO: 17)
DCPKCPPPEMLGGPSIFIFPPKPKDTLSISRTPEVTCLVVDLGPDDSDVQ

ITWFVDNTQVYTAKTSPREEQFNSTYRVVSVLPILHQDWLKGKEFKCKVN

SKSLPSPIERTISKAKGQPHEPQVYVLPPAQEELSRNKVSVTCLIKSFHP

PDIAVEWEITGQPEPENNYRTTPPQLDSDGTYFVYSKLSVDRSHWQRGNT

YTCSVSHEALHSHHTQKSLTQSPG (SEQ ID NO: 18)
DCPKCPPPEMLGGPSIFIFPPKPKDTLSISRTPEVTCLVVDLGPDDSDVQ

ITWFVDNTQVYTAKTSPREEQFNSTYRVVSVLPILHQDWLKGKEFKCKVN

SKSLPSPIERTISKDKGQPHEPQVYVLPPAQEELSRNKVSVTCLIEGFYP

SDIAVEWEITGQPEPENNYRTTPPQLDSDGTYFLYSRLSVDRSRWQRGNT

YTCSVSHEALHSHHTQKSLTQSPG (SEQ ID NO: 19)
GEGPKCPVPEIPGAPSVFIFPPKPKDTLSISRTPEVTCLVVDLGPDDSNV

QITWFVDNTEMHTAKTRPREEQFNSTYRVVSVLPILHQDWLKGKEFKCKV

NSKSLPSAMERTISKAKGQPHEPQVYVLPPTQEELSENKVSVTCLIKGFH

PPDIAVEWEITGQPEPENNYQTTPPQLDSDGTYFLYSRLSVDRSHWQRGN

TYTCSVSHEALHSHHTQKSLTQSPG
```

Replacing the human Fc fragment of an insulin-Fc fusion protein with a feline IgG2 isotype would be most preferable due to its lack of Fc(gamma) effector function in felines (much like the human IgG2 isotype).

A feline insulin-Fc fusion protein may comprise an insulin analog polypeptide as shown in SEQ ID NO: 4 with mutations on the B-chain and A-chain and comprising a C-chain of SEQ ID NO: 8.

```
                                             (SEQ ID NO: 8)
GGGPRR
                                             (SEQ ID NO: 4)
FVNQHLCGSDLVEALYLVCGERGFFYTDPTGGGPRRGIVEQCCHSICSLY

QLENYCN
```

The insulin analog polypeptide of SEQ ID NO: 4 is connected via a peptide linker of SEQ ID NO: 10 to a feline IgG2 Fc fragment of SEQ ID NO: 19.

```
                                             (SEQ ID NO: 10)
GGGGSGGGG
                                             (SEQ ID NO: 19)
GEGPKCPVPEIPGAPSVFIFPPKPKDTLSISRTPEVTCLVVDLGPDDSNV

QITWFVDNTEMHTAKTRPREEQFNSTYRVVSVLPILHQDWLKGKEFKCKV

NSKSLPSAMERTISKAKGQPHEPQVYVLPPTQEELSENKVSVTCLIKGFH

PPDIAVEWEITGQPEPENNYQTTPPQLDSDGTYFLYSRLSVDRSHWQRGN

TYTCSVSHEALHSHHTQKSLTQSPG
```

The resulting feline insulin-Fc fusion protein is shown below in SEQ ID NO: 32.

(SEQ ID NO: 32)
FVNQHLCGSDLVEALYLVCGERGFFYTDPTGGGPRRGIVEQCCHSICSLY

QLENYCNGGGGSGGGGGEGPKCPVPEIPGAPSVFIFPPKPKDTLSISRTP

EVTCLVVDLGPDDSNVQITWFVDNTEMHTAKTRPREEQFNSTYRVVSVLP

ILHQDWLKGKEFKCKVNSKSLPSAMERTISKAKGQPHEPQVYVLPPTQEE

LSENKVSVTCLIKGFHPPDIAVEWEITGQPEPENNYQTTPPQLDSDGTYF

LYSRLSVDRSHWQRGNTYTCSVSHEALHSHHTQKSLTQSPG

Figure 12:
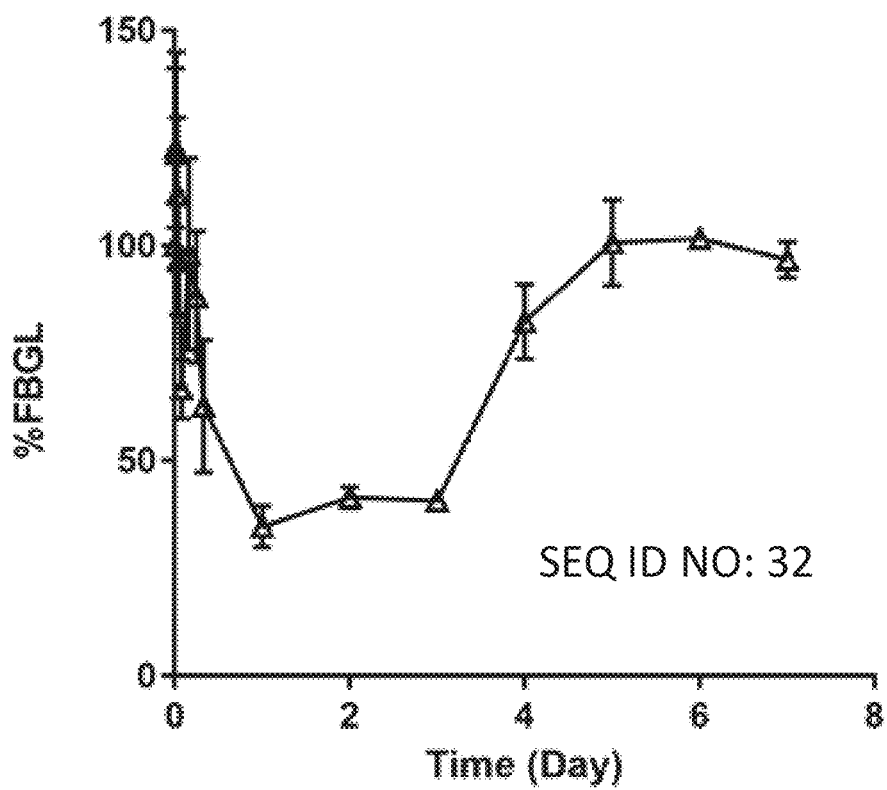
FIG. 12 shows average % fasting blood glucose levels from Day 0 to Day 7 for a cat dosed with the homodimer of SEQ ID NO: 32.

The feline insulin-Fc fusion protein of SEQ ID NO: 32 illustrates acceptable in vivo bioactivity in cats when administered subcutaneously, as is shown in FIG. 12. However, after several weekly treatments of SEQ ID NO: 32, the cats showed an immune response to the treatment. It was discovered that the cats had generated antibodies which were neutralizing to the action of the treatment in vivo. Further analysis revealed that these antibodies were targeting the insulin polypeptide at positions where amino acids had been mutated from natural insulin. More specifically, the amino acid at position 10 on the insulin B-chain had been mutated from His to Asp, and the amino acid at position 8 on the insulin A-chain had been mutated from Thr to His.

Without wishing to be bound by theory, it is believed that non-glycosylated insulin Fc-fusion proteins are less immunogenic than their counterpart insulin-Fc fusion proteins that are left in their natural glycosylated state. Although the antibodies generated in response to treatment with SEQ ID NO: 32 were targeted at the insulin polypeptide, producing a non-glycosylated insulin-Fc fusion protein was considered to have the potential to reduce the immunogenicity profile overall. It is known that mutating the Fc fragment at the natural glycosylation site found at position 140 from the N-terminus will prevent glycosylation of the molecule during expression from mammalian cells. It was therefore expected that a mutation from asparagine to serine at the natural glycan site found at position 140 from the N-terminus of the insulin Fc fusion protein of SEQ ID NO: 32 (resulting in SEQ ID NO: 34) while retaining the same insulin polypeptide and peptide linker, would result in an insulin-Fc fusion protein that retains acceptable in vivo bioactivity in cats when administered subcutaneously, but which has a significantly reduced immune response when repeatedly dosed.

The feline Fc fragment with the mutation from asparagine to serine at the natural glycan site is given in SEQ ID NO: 20.

(SEQ ID NO: 20)
GEGPKCPVPEIPGAPSVFIFPPKPKDTLSISRTPEVTCLVVDLGPDDSNV

QITWFVDNTEMHTAKTRPREEQFSSTYRVVSVLPILHQDWLKGKEFKCKV

NSKSLPSAMERTISKAKGQPHEPQVYVLPPTQEELSENKVSVTCLIKGFH

PPDIAVEWEITGQPEPENNYQTTPPQLDSDGTYFLYSRLSVDRSHWQRGN

TYTCSVSHEALHSHHTQKSLTQSPG (SEQ ID NO: 34)
FVNQHLCGSDLVEALYLVCGERGFFYTDPTGGGPRRGIVEQCCHSICSLY

QLENYCNGGGGSGGGGGEGPKCPVPEIPGAPSVFIFPPKPKDTLSISRTP

EVTCLVVDLGPDDSNVQITWFVDNTEMHTAKTRPREEQFSSTYRVVSVLP

ILHQDWLKGKEFKCKVNSKSLPSAMERTISKAKGQPHEPQVYVLPPTQEE

-continued

LSENKVSVTCLIKGFHPPDIAVEWEITGQPEPENNYQTTPPQLDSDGTYF

LYSRLSVDRSHWQRGNTYTCSVSHEALHSHHTQKSLTQSPG

An analogous compound for canines comprises the insulin polypeptide of SEQ ID NO: 5 and linker of SEQ ID NO: 9 with the native canine IgGB fragment of SEQ ID NO: 12.

(SEQ ID NO: 12)
DCPKCPAPEMLGGPSVFIFPPKPKDTLLIARTPEVTCVVVDLDPEDPEV

QISWFVDGKQMQTAKTQPREEQFNGTYRVVSVLPIGHQDWLKGKQFTCK

VNNKALPSPIERTISKARGQAHQPSVYVLPPSREELSKNTVSLTCLIKD

FFPPDIDVEWQSNGQQEPESKYRTTPPQLDEDGSYFLYSKLSVDKSRWQ

RGDTFICAVMHEALHNHYTQESLSHSPG

The resulting canine insulin-Fc fusion protein is given below in SEQ ID NO: 26.

(SEQ ID NO: 26)
FVNQHLCGSDLVEALALVCGERGFFYTDPTGGGPRRGIVEQCCHSICSLY

QLENYCNGGGGAGGGGDCPKCPAPEMLGGPSVFIFPPKPKDTLLIARTPE

VTCVVVDLDPEDPEVQISWFVDGKQMQTAKTQPREEQFNGTYRVVSVLPI

GHQDWLKGKQFTCKVNNKALPSPIERTISKARGQAHQPSVYVLPPSREEL

SKNTVSLTCLIKDFFPPDIDVEWQSNGQQEPESKYRTTPPQLDEDGSYFL

YSKLSVDKSRWQRGDTFICAVMHEALHNHYTQESLSHSPG

If the natural glycan site found at the cNg position of SEQ ID NO: 26 has the asparagine to serine mutation, the resulting canine insulin-Fc fusion protein is SEQ ID NO: 29. This compound for canines comprises the same insulin polypeptides of SEQ ID NO: 5 and linker of SEQ ID NO: 9 with the canine IgGB fragment of SEQ ID NO: 15 (which has an asparagine to serine mutation at the natural glycan site found at the cNg position).

(SEQ ID NO: 15)
DCPKCPAPEMLGGPSVFIFPPKPKDTLLIARTPEVTCVVVDLDPEDPEVQ

ISWFVDGKQMQTAKTQPREEQFSGTYRVVSVLPIGHQDWLKGKQFTCKVN

NKALPSPIERTISKARGQAHQPSVYVLPPSREELSKNTVSLTCLIKDFFP

PDIDVEWQSNGQQEPESKYRTTPPQLDEDGSYFLYSKLSVDKSRWQRGDT

FICAVMHEALHNHYTQESLSHSPG

The resulting canine insulin-Fc fusion protein is given below in SEQ ID NO: 29.

(SEQ ID NO: 29)
FVNQHLCGSDLVEALALVCGERGFFYTDPTGGGPRRGIVEQCCHSICSLY

QLENYCNGGGGAGGGGDCPKCPAPEMLGGPSVFIFPPKPKDTLLIARTPE

VTCVVVDLDPEDPEVQISWFVDGKQMQTAKTQPREEQFSGTYRVVSVLPI

GHQDWLKGKQFTCKVNNKALPSPIERTISKARGQAHQPSVYVLPPSREEL

SKNTVSLTCLIKDFFPPDIDVEWQSNGQQEPESKYRTTPPQLDEDGSYFL

YSKLSVDKSRWQRGDTFICAVMHEALHNHYTQESLSHSPG

The insulin-Fc fusion protein of SEQ ID NO: 29 shows acceptable in vivo bioactivity in dogs when administered subcutaneously but continues to generate antibodies targeting the insulin polypeptide after a few weekly treatments. This change from asparagine to serine at the N glycosylation site of the Fc fragment (cNg) to decrease its immunogenic potential did not eliminate the immune response that is targeted to the mutated portions of the insulin polypeptide.

Unexpectedly, it has been shown that a canine insulin-Fc fusion protein (SEQ ID NO: 31 below) with the same insulin polypeptide (SEQ ID NO: 5) and linker (SEQ ID NO: 9) and canine IgGB fragment but with a different mutation at the N glycosylation site of the Fc fragment (cNg) (e.g., asparagine to lysine) and the aspartic acid from the hinge region of the Fc fragment removed shows acceptable in vivo bioactivity in dogs when administered subcutaneously and does not generate antibodies even after several weekly treatments.

The canine IgGB fragment with an asparagine to lysine mutation at the N glycosylation site of the Fc fragment (cNg) and the aspartic acid from the hinge region of the Fc fragment removed is given in SEQ ID NO: 16.

```
                                              (SEQ ID NO: 16)
CPKCPAPEMLGGPSVFIFPPKPKDTLLIARTPEVTCVVVDLDPEDPEVQI

SWFVDGKQMQTAKTQPREEQFKGTYRVVSVLPIGHQDWLKGKQFTCKVNN

KALPSPIERTISKARGQAHQPSVYVLPPSREELSKNTVSLTCLIKDFFPP

DIDVEWQSNGQQEPESKYRTTPPQLDEDGSYFLYSKLSVDKSRWQRGDTF

ICAVMHEALHNHYTQESLSHSPG
```

The resulting canine insulin-Fc fusion protein is given in SEQ ID NO: 31.

```
                                              (SEQ ID NO: 31)
FVNQHLCGSDLVEALALVCGERGFFYTDPTGGGPRRGIVEQCCHSICSLY

QLENYCNGGGGAGGGGCPKCPAPEMLGGPSVFIFPPKPKDTLLIARTPEV

TCVVVDLDPEDPEVQISWFVDGKQMQTAKTQPREEQFKGTYRVVSVLPIG

HQDWLKGKQFTCKVNNKALPSPIERTISKARGQAHQPSVYVLPPSREELS

KNTVSLTCLIKDFFPPDIDVEWQSNGQQEPESKYRTTPPQLDEDGSYFLY

SKLSVDKSRWQRGDTFICAVMHEALHNHYTQESLSHSPG
```

It is therefore expected that a mutation from asparagine to lysine at the natural glycan site found at position 140 from the N-terminus in the analogous compound for cats (e.g., SEQ ID NO: 32 which is the compound with the same insulin polypeptide and feline IgG2 fragment which was shown to be immunogenic), i.e., mutating SEQ ID NO: 32 resulting in SEQ ID NO: 36, will similarly result in an insulin-Fc fusion protein with acceptable in vivo bioactivity in cats when administered subcutaneously, and which does not generate antibodies even after several weekly treatments.

```
                                              (SEQ ID NO: 36)
FVNQHLCGSDLVEALYLVCGERGFFYTDPTGGGPRRGIVEQCCHSICSLY

QLENYCNGGGGSGGGGEGPKCPVPEIPGAPSVFIFPPKPKDTLSISRTP

EVTCLVVDLGPDDSNVQITWFVDNTEMHTAKTRPREEQFKSTYRVVSVLP
```

```
-continued
ILHQDWLKGKEFKCKVNSKSLPSAMERTISKAKGQPHEPQVYVLPPTQEE

LSENKVSVTCLIKGFHPPDIAVEWEITGQPEPENNYQTTPPQLDSDGTYF

LYSRLSVDRSHWQRGNTYTCSVSHEALHSHHTQKSLTQSPG.
```

Definitions

As used herein, the articles "a" and "an" refer to one or more than one, e.g., to at least one of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

As used herein, an amount of a molecule, compound, conjugate, or substance effective to treat a disorder (e.g., a disorder described herein), "therapeutically effective amount," or "effective amount" refers to an amount of the molecule, compound, conjugate, or substance which is effective, upon single or multiple dose administration(s) to a subject, in treating a subject, or in curing, alleviating, relieving or improving a subject with a disorder (e.g., a disorder described herein) beyond that expected in the absence of such treatment.

As used herein, the term "analog" refers to a compound or conjugate (e.g., a compound or conjugate as described herein, e.g., insulin) having a chemical structure like that of another compound or conjugate but differing from it in at least one aspect.

As used herein, the term "antibody" or "antibody molecule" refers to an immunoglobulin molecule (Ig), immunologically active portions of an immunoglobulin (Ig) molecule, i.e., a molecule that contains an antigen binding site that specifically binds, e.g., immunoreacts with, an antigen. As used herein, the term "antibody domain" refers to a variable or constant region of an immunoglobulin. It is documented in the art that antibodies comprise several classes, for example IgA, IgM, or IgG in the case of mammals (e.g., felines). Classes of immunoglobulins can be further classified into different isotypes such as IgG1, IgG2, and IgG3, etc., or in other instances IgG1a, IgG1b, and IgG2. Those skilled in the art will recognize that immunoglobulin isotypes of a given immunoglobulin class will comprise different amino acid sequences, structures, and functional properties from one another (e.g., different binding affinities to Fc(gamma) receptors). "Specifically binds" or "immunoreacts with" means that the antibody reacts with one or more antigenic determinants of the desired antigen and has a lower affinity for other polypeptides, e.g., does not react with other polypeptides.

As used herein, the term "area-under-the-curve" or "AUC" refers to the integrated area under the % FBGL vs. time curve for a subject after a given dose of an insulin-Fc fusion protein configuration is administered. As used herein, the term "area-over-the curve" or "AOC" is used as a measure of the biological potency of an insulin-Fc fusion protein configuration such that the AOC equals the difference between the total possible area under the % FBGL vs. time curve and the AUC value. As used herein, the "normalized area-over-the curve," "normalized AOC," or "NAOC" is the AOC value divided by the actual dose of insulin-Fc fusion protein administered. As used herein, the term "normalized AOC ratio" or "NAOCR" is the ratio of the NAOC resulting from a particular administration of an insulin-Fc fusion protein to the NAOC resulting from the first administration of an insulin-Fc fusion protein in a series of administrations. The NAOCR thus provides a measure of the change in biological activity of an insulin-Fc fusion protein after repeated administrations.

As used herein, the term "bioactivity," "activity," "biological activity," "potency," "bioactive potency," or "biological potency" refers to the extent to which an insulin-Fc fusion protein activates the insulin receptor and/or exerts a reduction in blood glucose levels in a target subject. As used herein, "in vitro activity" or "insulin receptor activity" refers to the affinity with which an insulin-Fc fusion protein binds to the insulin receptor and is typically measured by the concentration at which an insulin-Fc fusion protein displaces half of an insulin reference standard from the insulin receptor in a competitive binding assay (i.e., IC50). As used herein, "in vivo activity" refers to the extent and duration of reduction in a target subject's fasting blood glucose level after administration of an insulin-Fc fusion protein.

As used herein, the term "biosynthesis," "recombinant synthesis," or "recombinantly made" refers to the process by which an insulin-Fc fusion protein is expressed within a host cell by transfecting the cell with a nucleic acid molecule (e.g., vector) encoding the insulin-Fc fusion protein (e.g., where the entire insulin-Fc fusion protein is encoded by a single nucleic acid molecule). Exemplary host cells include mammalian cells, e.g., HEK293 cells or CHO cells. The cells can be cultured using standard methods in the art and the expressed insulin-Fc fusion protein may be harvested and purified from the cell culture using standard methods in the art.

As used herein, the term "cell surface receptor" refers to a molecule such as a protein, generally found on the external surface of the membrane of a cell and which interacts with soluble molecules, e.g., molecules that circulate in the blood supply. In some embodiments, a cell surface receptor may include a hormone receptor (e.g., an insulin hormone receptor or insulin receptor (IR)) or an Fc receptor which binds to an Fc fragment or the Fc region of an antibody (e.g., an Fc(gamma) receptor, for example Fc(gamma) receptor I, or an Fc neonatal receptor, for example FcRn). As used herein, "in vitro activity" or "Fc(gamma) receptor activity" or "Fc(gamma) receptor binding" or "FcRn receptor activity" or "FcRn binding" refers to the affinity with which an insulin-Fc fusion protein binds to the Fc receptor (e.g. Fc(gamma) receptor or FcRn receptor) and is typically measured by the concentration of an insulin-Fc fusion protein that causes the insulin-Fc fusion protein to reach half of its maximum binding (i.e., EC50 value) as measured on an assay (e.g., an enzyme-linked immunosorbent assay (ELISA) assay) using OD 450 nm values as measured on a microplate reader. Alternatively, the affinity with which an insulin-Fc fusion protein binds to the Fc receptor (e.g., Fc(gamma) receptor or FcRn receptor) is measured by the OD 450 nm value obtained on a microplate reader in an enzyme-linked immunosorbent assay (ELISA) assay at a given concentration of the insulin-Fc fusion protein.

As used herein, the term "fasting blood glucose level" or "FBGL" refers to the average blood glucose level in a target subject at the end of a period during which no food is administered and just prior to the time at which an insulin-Fc fusion protein is administered. As used herein, the term "percent fasting blood glucose level," "% fasting blood glucose level," or "% FBGL" refers to the ratio of a given blood glucose level to the fasting blood glucose level multiplied by 100.

As used herein, the term "immunogenic" or "immunogenicity" refers to the capacity for a given molecule (e.g., an insulin-Fc fusion protein of the present invention) to provoke the immune system of a target subject.

As used herein, the term "insulin reference standard" is any one of: (i) a naturally occurring insulin from a mammal (e.g., a human or dog); (ii) an insulin polypeptide that does not comprise an Fc fragment; or (iii) a standard of care insulin (e.g., a commercially available insulin).

As used herein, the term "monomer" refers to a protein or a fusion protein comprising a single polypeptide. In some examples, the "monomer" is a protein or a fusion protein, e.g., a single polypeptide, comprising an insulin polypeptide and an Fc fragment polypeptide, wherein the insulin polypeptide and Fc fragment polypeptide are joined by a peptide linker to form the single polypeptide. In some examples, the monomer is encoded by a single nucleic acid molecule.

As used herein, "N-terminus" refers to the start of a protein or polypeptide that is initiated by an amino acid containing a free amine group that is the alpha-amino group of the amino acid (e.g., the free amino that is covalently linked to one carbon atom that is located adjacent to a second carbon atom, wherein the second carbon atom is part of the carbonyl group of the amino acid). As used herein, "C-terminus" refers to the end of a protein or polypeptide that is terminated by an amino acid containing a carboxylic acid group, wherein the carbon atom of the carboxylic acid group is located adjacent to the alpha-amino group of the amino acid.

As used herein, "pharmacodynamics" or "PD" generally refers to the biological effects of an insulin-Fc fusion protein in a subject. Specifically, herein the PD refers to the measure of the reduction in fasting blood glucose level over time in a subject after the administration of an insulin-Fc fusion protein.

As used herein, "pharmacokinetics" or "PK" generally refers to the characteristic interactions of an insulin-Fc fusion protein and the body of the subject in terms of its absorption, distribution, metabolism, and excretion. Specifically, herein the PK refers to the concentration of an insulin-Fc fusion protein in the blood or serum of a subject at a given time after the administration of the insulin-Fc fusion protein. As used herein, "half-life" refers to the time taken for the concentration of insulin-Fc fusion protein in the blood or serum of a subject to reach half of its original value as calculated from a first order exponential decay model for drug elimination. Insulin-Fc fusion proteins with greater "half-life" values demonstrate greater duration of action in the target subject.

The terms "sequence identity" "sequence homology" "homology" or "identical" in amino acid or nucleotide sequences as used herein describes that the same nucleotides or amino acid residues are found within the variant and reference sequences when a specified, contiguous segment of the nucleotide sequence or amino acid sequence of the variant is aligned and compared to the nucleotide sequence or amino acid sequence of the reference sequence. Methods for sequence alignment and for determining identity between sequences are known in the art, including the use of Clustal Omega, which organizes, aligns, and compares sequences for similarity, wherein the software highlights each sequence position and compares across all sequences at that position and assigns one of the following scores: an "*" (asterisk) for sequence positions which have a single, fully conserved residue, a ":" (colon) indicates conservation between groups of strongly similar properties with scoring greater than 0.5 in the Gonnet PAM 250 matrix, and a "." (period) indicates conservation between groups of weakly similar properties with scoring less than or equal to 0.5 in the Gonnet PAM 250 matrix, a "-" (dash) indicates a sequence gap, meaning that no local homology exists within a particular set of comparisons within a certain range of the sequences, and an empty space " " indicates little or no sequence homology for that particular position across the compared sequences. With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. In some embodiments, the contiguous segment used for comparison to the reference nucleotide sequence or reference amino acid sequence will comprise at least 6, 10, 15, or 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are known in the art.

In embodiments, the determination of percent identity or "homology" between two sequences is accomplished using a mathematical algorithm. For example, the percent identity of an amino acid sequence is determined using the Smith-Waterman homology search algorithm using an atone 6 gap search with a gap open penalty of 12 and a gap extension penalty of 2, BLOSUM matrix 62. In embodiments, the percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

As used herein, the term "homology" is used to compare two or more proteins by locating common structural characteristics and common spatial distribution of, for instance, beta strands, helices, and folds. Accordingly, homologous protein structures are defined by spatial analyses. Measuring structural homology involves computing the geometric-topological features of a space. One approach used to generate and analyze three-dimensional (3D) protein structures is homology modeling (also called comparative modeling or knowledge-based modeling) which works by finding similar sequences since 3D similarity reflects 2D similarity. Homologous structures do not imply sequence similarity as a necessary condition.

As used herein, the term "subject" or "target subject" or "patient" or "patient subject" are intended to include felines. Exemplary feline subjects include cats having a disease or a disorder, e.g., diabetes or another disease or disorder described herein, or normal subjects.

As used herein, the term "titer" or "yield" refers to the amount of a fusion protein product (e.g., an insulin-Fc fusion protein described herein) resulting from the biosynthesis (e.g., in a mammalian cell, e.g., in a HEK293 cell or CHO cell) per volume of the cell culture. The amount of product may be determined at any step of the production process (e.g., before or after purification), but the yield or titer is always stated per volume of the original cell culture. As used herein, the term "product yield" or "total protein yield" refers to the total amount of insulin-Fc fusion protein expressed by cells and purified via at least one affinity chromatography step (e.g., Protein A or Protein G) and includes monomers of insulin-Fc fusion protein, homodimers of insulin-Fc fusion protein, and higher-order molecular aggregates of homodimers of insulin-Fc fusion protein. As used herein, the term "percent homodimer" or "% homodimer" refers to the proportion of a fusion protein product (e.g., an insulin-Fc fusion protein described herein) that is the desired homodimer. As used herein, the term "homodimer titer" refers to the product of the % homodimer and the total protein yield after Protein A purification step reported per volume of the cell culture.

As used herein, the terms "treat" or "treating" a subject having a disease or a disorder refer to subjecting the subject to a regimen, for example the administration of a fusion protein, such as a fusion protein described herein, such that at least one symptom of the disease or disorder is cured, healed, alleviated, relieved, altered, remedied, ameliorated, or improved. Treating includes administering an amount effective to alleviate, relieve, alter, remedy, ameliorate, improve, or affect the disease or disorder, or the symptoms of the disease or disorder. The treatment may inhibit deterioration or worsening of a symptom of a disease or disorder.

Insulin-Fc Fusion Protein Components and Structure

The present disclosure relates to a composition of a fusion protein (i.e., an insulin-Fc fusion protein described herein comprises) comprising an insulin polypeptide linked via a peptide linker to a species-specific Fc fragment, and its use to treat diabetes in dogs. As used herein, the terms "fusion protein" and "insulin-Fc fusion protein" refer to a protein comprising more than one part, for example from different sources (different proteins, polypeptides, cells, etc.), that are covalently linked through peptide bonds. The insulin-Fc fusion proteins are covalently linked by (i) connecting the genes that encode for each part into a single nucleic acid molecule and (ii) expressing in a host cell (e.g., HEK or CHO) the protein for which the nucleic acid molecule encodes as follows: (N-terminus)-insulin polypeptide-linker-Fc fragment-(C-terminus). The fully recombinant synthesis approach is preferred over methods in which the insulin polypeptide and Fc fragments are synthesized separately and then chemically conjugated. The chemical conjugation step and subsequent purification process increase the manufacturing complexity, reduce product yield, and increase cost.

As used herein, the term "dimer" refers to a protein or a fusion protein comprising two polypeptides linked covalently. In embodiments, two identical polypeptides are linked covalently (e.g., via disulfide bonds) forming a "homodimer". FIG. 1 diagrammatically represents an insulin-Fc fusion protein homodimer. The insulin polypeptide comprises a B-chain, a C-chain and an A-chain, and each insulin polypeptide is joined via a peptide linker to an Fc fragment. Two identical insulin-Fc fusion protein monomers are joined together via disulfide bonds to form an insulin-Fc fusion protein homodimer. The total number of disulfide bonds may be greater or less than the number shown in FIG. 1. The Fc fragment comprises a conserver asparagine (N)-glycosylation site, at which glycols may bond during recombinant manufacturing of the insulin-Fc fusion protein in mammalian cells. In embodiments, the homodimer is encoded by a single nucleic acid molecule, wherein the homodimer is made recombinantly inside a cell by first forming insulin-Fc fusion protein monomers and by then assembling two identical insulin-Fc fusion protein monomers into the homodimer upon further processing inside the cell.

As used herein, the terms "multimer," "multimeric," or "multimeric state" refer to non-covalent, associated forms of Fc fusion protein dimers that may be in equilibrium with Fc fusion protein dimers or may act as permanently aggregated versions of Fc fusion protein dimers (e.g., dimers of Fc fusion protein homodimers, trimers of Fc fusion protein homodimers, tetramers of Fc fusion protein homodimers, or higher order aggregates containing five or more Fc fusion protein homodimers). It may be expected that multimeric forms of Fc fusion proteins may have different physical, stability, or pharmacologic activities from that of the, e.g., insulin-Fc fusion protein homodimers.

Insulin Polypeptide

An insulin polypeptide may be, for example, an insulin or insulin analog produced by β-cells in the islets of Langerhans within the pancreas. Insulin functions by regulating the absorption of glucose from the blood. Upon a stimulus, such as increased protein and glucose levels, insulin is released from β-cells and binds to the insulin receptor (IR), initiating a signal cascade that affects many aspects of mammalian (e.g., human, feline, etc.) metabolism. Disruption of this process is directly related to several diseases, notably diabetes, insulinoma, insulin resistance, metabolic syndromes, and polycystic ovary syndrome.

Insulin analogs of the present disclosure may be related to the structure of insulin yet contain one or more modifications. In some embodiments, the insulin analog comprises at least one amino acid substitution, deletion, addition, or chemical modification relative to insulin, which may impact a particular feature or characteristic of the insulin-Fc fusion protein (e.g., insulin-Fc fusion protein described herein) configuration. For example, the modifications or alterations described herein may impact the structure, stability, pH sensitivity, bioactivity, or binding affinity of the insulin-Fc fusion protein to a cell surface receptor (e.g., an insulin hormone receptor). In some embodiments, an amino acid substitution, addition, deletion, or a chemical modification relative to insulin may affect the activity of the insulin or insulin analog relative to a reference standard. In some embodiments, the position of the amino acid sequence is referenced to the N-terminus of the insulin polypeptide, with position 1 being the first amino acid of the B-chain of the insulin polypeptide. In embodiments, the insulin or insulin analog is a three-segment peptide comprising elements of a B-chain, a C-peptide, and an A-chain. In embodiments, the insulin or insulin analog comprises a wild-type insulin B, C, and/or A chain, e.g., from a cat. In other embodiments, an insulin-Fc fusion protein described herein comprises an insulin polypeptide comprising a mutant insulin B-chain, C-peptide, and/or A-chain configuration to a cell surface receptor (e.g., an insulin hormone receptor) relative to a reference standard.

The amino acid sequence of insulin is strongly conserved throughout evolution, particularly in vertebrates. For example, native canine and porcine insulins differ by only one amino acid from human insulin, native bovine insulin differs by only three amino acids from human insulin, and native feline insulin differs by just four amino acids from human insulin. As used herein, the terms "B-chain or B-chain analog", "C-peptide" or "C-chain", and "A-chain or A-chain analog" refer to the peptide segments of an insulin polypeptide as illustrated in FIG. 1. Native insulin is a 51 amino acid hormone containing two peptide chains (i.e., a B-chain and an A-chain) connected via disulfide bonds (e.g., disulfide bonds formed by one or more B-chain cysteine side chain thiols and one or more A-chain cysteine side chain thiols). The A-chain of native insulin is 21 amino acids in length and the B-chain of native insulin is 30 amino acids in length. In the native form of insulin, the A-chain contains one intrachain disulfide bond formed by two A-chain cysteine side chain thiols. For reference purposes, the sequences for the human insulin B-chain of SEQ ID NO: 1 and the human insulin A-chain of SEQ ID NO: 2 are shown below:

(SEQ ID NO: 1)
FVNQHLCGSHLVEALYLVCGERGFFYTPKT (SEQ ID NO: 2)
GIVEQCCTSICSLYQLENYCN.

As used herein, the term "insulin" or "insulin polypeptide" encompasses mature insulin, preproinsulin, proinsulin, and naturally occurring insulin, or analogs thereof. In embodiments, an insulin polypeptide can be a full-length insulin polypeptide or a fragment thereof. In embodiments, modifications to the sequence of the insulin or insulin analog (e.g., amino acid substitutions, deletions, or additions or chemical modifications) may be to the B-chain of insulin, the C-peptide of insulin, the A-chain of insulin, or any combination thereof. In embodiments, the C-chain peptide comprises an amino acid sequence located between the B-chain and the A-chain, and the C-peptide covalently connects the B-chain and A-chain via peptide bonds.

Insulin is normally constructed as a N-terminus-B-chain:C-chain:A-chain-C-terminus polypeptide, wherein the C-chain is cleaved to make it bioactive. For reference purposes, the sequence of the entire human insulin molecule including the C-chain (i.e., human proinsulin) is shown below with the C-chain in bold:

(SEQ ID NO: 3)
FVNQHLCGSHLVEALYLVCGERGFFYTPKTRREAEDLQVGQVELGGGPGA
GSLQPLALEGSLQKRGIVEQCCTSICSLYQLENYCN.

The transformation of the single-chain insulin polypeptide into a bioactive two-chain polypeptide is normally accomplished within the β-cells of the islets of Langerhans prior to glucose-stimulated insulin secretion by two endoproteases, Type I endoproteases, PC1 and PC3, that disrupt the C peptide-B chain connection and PC2, and a Type II endoprotease, that cleaves the C peptide-A chain bond at exactly the right sites. However, cell systems used for the biosynthesis of therapeutic molecules such as insulin (e.g., bacteria, yeast, and mammalian (e.g., HEK and CHO) cell systems) do not possess this pathway, and therefore the transformation must take place after expression and harvesting of the single chain polypeptide using chemical or enzymatic methods. All the known techniques for cleaving the C-chain after expression and harvesting rely on first modifying the C-chain such that it terminates in a lysine just before the N-terminus of the A-chain. Then, using an enzyme selected from the trypsin or Lys-C families, which clips peptide bonds specifically at the C-termini of lysine residues, the single chain-insulin polypeptide is cleaved at the C-terminal lysine of the C-chain and at the C-terminal lysine at the 29th position from the N-terminus of the B-chain. In some cases, the resulting bioactive two-chain insulin is used without reattaching the clipped amino acid at the 30th position from the N-terminus of the B-chain, and in some cases the clipped amino acid at the 30th position from the N-terminus of the B-chain is added back to the molecule using an additional enzymatic method. Such a process works well with insulin because it contains only one lysine in its entire two chain polypeptide form. However, this process cannot be used on the insulin-Fc fusion proteins contained herein, because all known Fc fragments contain multiple lysine residues. The enzymatic cleavage process would, therefore, digest the Fc fragment into non-functional parts, thereby eliminating the ability of the Fc fragment to prolong the action of the insulin polypeptide in vivo. Therefore, an insulin-Fc fusion protein of the present invention must comprise an insulin polypeptide that does not require C-chain cleavage and is therefore bioactive in its single chain form.

Several bioactive single chain insulin polypeptides have been described in the art. In all cases, the single chain insulin polypeptides contain C-chains of specific length and composition as well as A-chains and B-chains mutated at specific amino acid sites to achieve electrostatic balance, prevent aggregation, and enhance insulin receptor (IR) binding and/or downstream signaling to achieve bioactivity at levels comparable to that of the native two-chain insulin. Herein, the location of mutations on peptide segments are notated using the name of the segment (e.g., B-chain, C-chain, A-chain) and the number of the amino acid counting from the N-terminus of the segment. For example, the notation "B10" refers to the 10th amino acid from the N-terminus of the amino acid sequence of the B-chain. The notation "A8" refers to the 8th amino acid from the N-terminus of the A-chain. Furthermore, if an amino acid is mutated from its native form to a new amino acid at a particular location, the location is appended with the one letter amino acid code for the new amino acid. For example, B10D refers to an aspartic acid mutation at the 10th amino acid from the N-terminus of the amino acid sequence of the B-chain and A8H refers to a histidine mutation at the 8th amino acid from the N-terminus of the amino acid sequence of the A-chain.

The insulin polypeptide of an insulin-Fc fusion protein may comprise the amino acid sequence of SEQ ID NO: 5, SEQ ID NO: 6, or SEQ ID NO: 7.

(SEQ ID NO: 5)
FVNQHLCGSDLVEALALVCGERGFFYTDPTGGGPRRGIVEQCCHSICSLY

QLENYCN (SEQ ID NO: 6)
FVNQHLCGSHLVEALYLVCGERGFFYTPKAAAAAAAKGIVEQCCTSICSL

YQLENYCN (SEQ ID NO: 7)
FVNQHLCGSHLVEALYLVCGERGFFYTPKAGGGPRRGIVEQCCTSICSLY

QLENYCN

In embodiments, the insulin polypeptide of the insulin-Fc fusion protein comprises the amino acid sequence of SEQ ID NO: 4.

(SEQ ID NO: 4)
FVNQHLCGSDLVEALYLVCGERGFFYTDPTGGGPRRGIVEQCCHSICSLY

QLENYCN

In embodiments, modifications to the sequence of the insulin or insulin analog (e.g., amino acid substitutions, deletions, or additions or chemical modifications) may be added to either the B-chain of insulin, the C-peptide of insulin, the A-chain of insulin, or any combination thereof. In embodiments, the C-chain peptide comprises an amino acid sequence located between the B-chain and the A-chain, and the C-peptide covalently connects the B-chain and A-chain via peptide bonds.

In an embodiment, the insulin polypeptide comprises a C-peptide, e.g., a C-chain element which comprises the amino acid sequence (SEQ ID NO: 8)
GGGPRR.

Fc Fragment

In embodiments, a fusion protein described herein comprises an Fc fragment, e.g., connected to an insulin polypeptide described herein.

The term "Fc region," "Fc domain," "Fc polypeptide," or "Fc fragment" as used herein is used to define a C-terminal region of an immunoglobulin heavy chain. The Fc fragment, region, or domain may be a native sequence Fc region or a variant/mutant Fc region. Although the boundaries of the Fc region of an immunoglobulin heavy chain may vary, they generally comprise some or all the hinge region of the heavy chain, the CH2 region of the heavy chain, and the CH3 region of the heavy chain. The hinge region of a feline antibody comprises amino acid sequences that connect the CH1 domain of the heavy chain to the CH2 region of the heavy chain and contains one or more cysteines that form one or more interheavy chain disulfide bridges to form a homodimer of the Fc fusion protein from two identical but separate monomers of the Fc fusion protein. The hinge region may comprise all or part of a naturally occurring amino acid sequence or a non-naturally occurring amino acid sequence.

Each IgG fragment contains a conserved asparagine (N)-glycosylation site in the CH2 domain of each heavy chain of the Fc region. Herein, the notation used to refer to the conserved N-glycosylation site is "cNg". One way to remove the attached glycan from a synthesized insulin-Fc fusion protein is to mutate the cNg site to prevent the attachment of glycans altogether during production in the host cell. Herein, the notation used to describe a cNg mutation is cNg-(substituted amino acid). For example, if the asparagine at the cNg site is mutated to serine, this mutation is notated as "cNg-S".

The absolute position of the cNg site from the N-terminus of the B-chain of the insulin-Fc fusion protein varies depending on the length of the insulin polypeptide, the length of the linker, and any omitted amino acids in the Fc fragment prior to the cNg site. Herein, the notation used to refer to the absolute position of the cNg site in a given insulin-Fc fusion protein sequence (as measured counting from the N-terminus of the B-chain of the insulin-Fc fusion protein) is "NB(number)". For example, if the cNg site is found at the 138th amino acid position as counted from the N-terminus of the B-chain, the absolute position of this site is referred to as cNg-NB138. As a further example, if the cNg site is found at the 138th amino acid position as counted from the N-terminus of the B-chain, and the asparagine at this site is mutated to serine, this mutation is noted as "cNg-NB138-S".

An Fc receptor (FcR) refers to a receptor that binds to an Fc: fragment or the Fc region of an antibody. In embodiments, the FcR is a native sequence feline FcR. In embodiments, the FcR is one which binds an Fc fragment or the Fc region of an IgG antibody (a gamma receptor) and includes without limitation, receptors of the Fc(gamma) receptor I, Fc(gamma) receptor IIa, Fc(gamma) receptor IIb, and Fc(gamma) receptor III subclasses, including allelic variants and alternatively spliced forms of these receptors. "FcR" also includes the neonatal receptor, FcRn, which is responsible for the transfer of maternal IgGs to the fetus and is also responsible for the prolonged in vivo elimination half-lives of antibodies and Fc-fusion proteins in vivo. In embodiments, an Fc fragment described herein is capable of binding to mammalian Fc(gamma) or Fc(Rn) receptors, e.g., feline Fc(gamma) or feline Fc(Rn) receptor.

In embodiments, the Fc fragment comprises the Fc region (e.g., hinge region, CH2 domain, and CH3 domain) of a mammalian IgG, e.g., feline IgG2. In embodiments, the Fc fragment comprises the hinge region (or a fragment thereof) of a feline immunoglobulin (e.g., an IgG, e.g., IgG2). In embodiments, the Fc fragment comprises the Fc region (e.g., CH2 domain and CH3 domain) of feline IgG2.

Examples of canine Fc fragments are given in SEQ ID NO: 11 (canine IgGA), SEQ ID NO: 12 (canine IgGB), SEQ ID NO: 13 (canine IgGC), and SEQ ID NO: 14 (canine IgGD).

(SEQ ID NO: 11)
RCTDTPPCPVPEPLGGPSVLIFPPKPKDILRITRTPEVTCVVLDLGREDP

EVQISWFVDGKEVHTAKTQSREQQFNGTYRVVSVLPIEHQDWLTGKEFKC

RVNHIDLPSPIERTISKARGRAHKPSVYVLPPSPKELSSSDTVSITCLIK

DFYPPDIDVEWQSNGQQEPERKHRMTPPQLDEDGSYFLYSKLSVDKSRWQ

QGDPFTCAVMHETLQNHYTDLSLSHSPG (SEQ ID NO: 12)
DCPKCPAPEMLGGPSVFIFPPKPKDTLLIARTPEVTCVVVDLDPEDPEVQ

ISWFVDGKQMQTAKTQPREEQFNGTYRVVSVLPIGHQDWLKGKQFTCKVN

NKALPSPIERTISKARGQAHQPSVYVLPPSREELSKNTVSLTCLIKDFFP

PDIDVEWQSNGQQEPESKYRTTPPQLDEDGSYFLYSKLSVDKSRWQRGDT

FICAVMHEALHNHYTQESLSHSPG (SEQ ID NO: 13)
CNNCPCPGCGLLGGPSVFIFPPKPKDILVTARTPTVTCVVVDLDPENPEV

QISWFVDSKQVQTANTQPREEQSNGTYRVVSVLPIGHQDWLSGKQFKCKV

NNKALPSPIEEIISKTPGQAHQPNVYVLPPSRDEMSKNTVTLTCLVKDFF

PPEIDVEWQSNGQQEPESKYRMTPPQLDEDGSYFLYSKLSVDKSRWQRGD

TFICAVMHEALHNHYTQISLSHSPG (SEQ ID NO: 14)
CISPCPVPESLGGPSVFIFPPKPKDILRITRTPEITCVVLDLGREDPEVQ

ISWFVDGKEVHTAKTQPREQQFNSTYRVVSVLPIEHQDWLTGKEFKCRVN

HIGLPSPIERTISKARGQAHQPSVYVLPPSPKELSSSDTVTLTCLIKDFF

PPEIDVEWQSNGQPEPESKYHTTAPQLDEDGSYFLYSKLSVDKSRWQQGD

TFTCAVMHEALQNHYTDLSLSHSPG

In embodiments, the Fc fragment comprises a wild-type feline IgG2 with the following amino acid sequence:

(SEQ ID NO: 21)
GEGPKCPVPEIPGAPSVFIFPPKPKDTLSISRTPEVTCLVVDLGPDDSNV

QITWFVDNTEMHTAKTRPREEQFKSTYRVVSVLPILHQDWLKGKEFKCKV

NSKSLPSAMERTISKAKGQPHEPQVYVLPPTQEELSENKVSVTCLIKGFH

PPDIAVEWEITGQPEPENNYQTTPPQLDSDGTYFLYSRLSVDRSHWQRGN

TYTCSVSHEALHSHHTQKSLTQSPG.

Linker

In embodiments, a fusion protein described herein comprises a linker, e.g., between one or more domains of the polypeptide. For example, a fusion protein comprises a linker between the insulin polypeptide and the Fc fragment.

In embodiments, the linker is a peptide. In embodiments, the peptide linker comprises amino acids (e.g., natural, or unnatural amino acids). In embodiments, the peptide linker can be encoded by a nucleic acid molecule, (e.g., such that a single nucleic acid molecule can encode the various peptides within an insulin polypeptide as well as the peptide linker as well as the Fc fragment). The peptide linker may comprise the amino acid sequence of (SEQ ID NO: 9)
GGGGAGGGG.

In embodiments, the peptide linker comprises the amino acid sequence (SEQ ID NO: 10)
GGGGSGGGG.

Fusion Protein

Provided herein are fusion proteins, e.g., insulin-Fc fusion proteins. In embodiments, the fusion protein comprises an insulin polypeptide described herein, e.g., in the Insulin polypeptide section herein. In embodiments, the fusion protein comprises an Fc fragment, e.g., an Fc fragment described herein, e.g., in the Fc fragment section herein. In embodiments, the fusion protein comprises a linker between the insulin polypeptide described herein, e.g., in the Insulin polypeptide section herein and the Fc fragment, e.g., an Fc fragment described herein, e.g., in the Fc fragment section herein. Exemplary linkers (e.g., peptide linkers) are described in greater detail in the Linker section herein.

In embodiments, the insulin polypeptide comprises domains in the following orientation from N- to C-termini: (N-terminus)-B-chain-C-peptide-A-chain-(C-terminus). In embodiments, the insulin polypeptide is located on the N-terminal side of the Fc fragment. In embodiments, the fusion protein comprises domains in the following orientation from N- to C-termini: (N-terminus)-insulin polypeptide-linker-Fc fragment-(C-terminus) (e.g., (N-terminus)-B- chain-C-peptide-A-chain-linker-Fc fragment-(C-terminus)) as illustrated in FIG. 1. In embodiments, the fusion protein, also referred to as the insulin-Fc fusion protein, is comprised of two identical insulin-Fc fusion proteins covalently bound together via one or more disulfide bonds (shown as dotted lines in FIG. 1; total number of disulfide bonds in actuality may be greater or lower than the number shown in FIG. 1). Each insulin-Fc fusion protein comprises an insulin polypeptide molecule containing an insulin B-chain and an insulin A-chain that are connected between the B-chain-C-terminal region and the A-chain-NH2 terminal region with a C-chain (gray line in FIG. 1), and the A-chain-C-terminal region and Fc-chain amino terminus with a linker, where the insulin-Fc fusion protein sequence terminates in the Fc-CH3-C-terminal region. Note that the B-chain and A-chain are also linked together via two disulfide bonds (dotted lines in FIG. 1). The A-chain also has an intramolecular disulfide bond (not shown in FIG. 1).

The full-length sequences of the insulin-Fc fusion proteins of the present technology are provided below:

(SEQ ID NO: 32)
FVNQHLCGSDLVEALYLVCGERGFFYTDPTGGGPRRGIVEQCCHSICSLY

QLENYCNGGGGSGGGGGEGPKCPVPEIPGAPSVFIFPPKPKDTLSISRTP

EVTCLVVDLGPDDSNVQITWFVDNTEMHTAKTRPREEQFNSTYRVVSVLP

ILHQDWLKGKEFKCKVNSKSLPSAMERTISKAKGQPHEPQVYVLPPTQEE

LSENKVSVTCLIKGFHPPDIAVEWEITGQPEPENNYQTTPPQLDSDGTYF

LYSRLSVDRSHWQRGNTYTCSVSHEALHSHHTQKSLTQSPG (SEQ ID NO: 34)
FVNQHLCGSDLVEALYLVCGERGFFYTDPTGGGPRRGIVEQCCHSICSLY

QLENYCNGGGGSGGGGGEGPKCPVPEIPGAPSVFIFPPKPKDTLSISRTP

EVTCLVVDLGPDDSNVQITWFVDNTEMHTAKTRPREEQFSSTYRVVSVLP

ILHQDWLKGKEFKCKVNSKSLPSAMERTISKAKGQPHEPQVYVLPPTQEE

LSENKVSVTCLIKGFHPPDIAVEWEITGQPEPENNYQTTPPQLDSDGTYF

LYSRLSVDRSHWQRGNTYTCSVSHEALHSHHTQKSLTQSPG (SEQ ID NO: 36)
FVNQHLCGSDLVEALYLVCGERGFFYTDPTGGGPRRGIVEQCCHSICSLY

QLENYCNGGGGSGGGGGEGPKCPVPEIPGAPSVFIFPPKPKDTLSISRTP

EVTCLVVDLGPDDSNVQITWFVDNTEMHTAKTRPREEQFKSTYRVVSVLP

ILHQDWLKGKEFKCKVNSKSLPSAMERTISKAKGQPHEPQVYVLPPTQEE

LSENKVSVTCLIKGFHPPDIAVEWEITGQPEPENNYQTTPPQLDSDGTYF

LYSRLSVDRSHWQRGNTYTCSVSHEALHSHHTQKSLTQSPG

The "full aa sequences" of the fusion proteins of SEQ ID NO: 32, SEQ ID NO: 34 and SEQ ID NO: 36 may include a leader sequence. In embodiments, a fusion protein described herein does not include a leader sequence at the N-terminus. In other embodiments, a fusion protein described herein includes a leader sequence, e.g., at the N-terminus. An exemplary leader sequence includes the amino acid sequence MEWSWVFLFFLSVTTGVHS (SEQ ID NO: 38). In embodiments, a fusion protein described herein is encoded by a nucleic acid molecule comprising a leader sequence, e.g., for expression (e.g., recombinant expression) in cells (e.g., eukaryotic, e.g., mammalian cells). In embodiments, the leader sequence is part of the fusion protein inside a cell and then the leader sequence is cleaved off, e.g., within the cell or in the cell culture, during expression of the fusion protein into the cell culture media via a process (e.g., an enzymatic process).

An exemplary nucleic acid sequence encoding a leader sequence includes the nucleic acid sequence (SEQ ID NO: 39)
ATGGAATGGAGCTGGGTCTTTCTCTTCTTCCTGTCAGTAACGACTGGTGT

CCACTCC.

In other embodiments, a fusion protein described herein is encoded by a nucleic acid molecule not comprising a leader sequence.

An exemplary nucleic acid sequence encoding the insulin-Fc fusion protein of SEQ ID NO: 32 is given below:

(SEQ ID NO: 33)
ATGGAATGGAGCTGGGTCTTTCTCTTCTTCCTGTCAGTAACGACTGGTGT

CCACTCCTTCGTGAACCAGCACCTGTGCGGCTCCGACCTGGTGGAAGCTC

TGTATCTCGTGTGCGGCGAGCGGGGCTTCTTCTACACCGATCCCACTGGA

GGCGGTCCACGCAGAGGCATCGTGGAACAGTGCTGCCACTCCATCTGCTC

CCTGTACCAGCTGGAAAACTACTGCAATGGCGGAGGTGGTTCAGGAGGCG

GTGGAGGTGAGGGCCCCAAGTGCCCCGTGCCCGAGATTCCCGGTGCCCCC

AGCGTGTTCATCTTTCCCCCAAAACCCAAGGACACCCTGAGCATCAGCAG

GACCCCCGAGGTGACCTGCCTGGTGGTGGACCTGGGACCCGACGACAGCA

ACGTGCAGATCACCTGGTTCGTGGACAACACCGAGATGCACACCGCCAAG

ACCAGGCCTCGGGAGGAGCAGTTCAACAGCACCTACAGGGTGGTGAGCGT

GCTGCCCATCCTGCACCAGGACTGGCTGAAGGGCAAGGAGTTCAAGTGCA

AGGTGAACAGCAAGAGCCTGCCCAGCGCCATGGAGAGGACCATCAGCAAG

GCCAAGGGTCAGCCCCACGAGCCCCAAGTGTACGTGCTTCCCCCGACCCA

GGAGGAGTTGAGCGAGAACAAAGTGAGCGTGACCTGCCTGATCAAGGGCT

TCCACCCTCCCGACATCGCCGTGGAGTGGGAGATCACCGGCCAGCCTGAG

CCGGAAAATAACTACCAGACCACCCCTCCACAGCTGGACAGCGACGGCAC

CTACTTCCTTTACAGCAGGCTGTCTGTGGACCGAAGCCATTGGCAAAGGG

GCAACACCTACACCTGCAGCGTGAGCCACGAGGCTCTGCACAGCCACCAC

ACCCAGAAGTCTCTGACCCAGAGCCCCGGATAG

An exemplary nucleic acid sequence encoding insulin-Fc fusion protein of SEQ ID NO: 34 is given below:

(SEQ ID NO: 35)
ATGGAATGGAGCTGGGTCTTTCTCTTCTTCCTGTCAGTAACGACTGGTGT

CCACTCCTTCGTGAACCAGCACCTGTGCGGCTCCGACCTGGTGGAAGCTC

TGTATCTCGTGTGCGGCGAGCGGGGCTTCTTCTACACCGATCCCACTGGA

GGCGGTCCACGCAGAGGCATCGTGGAACAGTGCTGCCACTCCATCTGCTC

CCTGTACCAGCTGGAAAACTACTGCAATGGCGGAGGTGGTTCAGGAGGCG

GTGGAGGTGAGGGCCCCAAGTGCCCCGTGCCCGAGATTCCCGGTGCCCCC

AGCGTGTTCATCTTTCCCCCAAAACCCAAGGACACCCTGAGCATCAGCAG

GACCCCCGAGGTGACCTGCCTGGTGGTGGACCTGGGACCCGACGACAGCA

-continued

```
ACGTGCAGATCACCTGGTTCGTGGACAACACCGAGATGCACACCGCCAAG

ACCAGGCCTCGGGAGGAGCAGTTCAGCAGCACCTACAGGGTGGTGAGCGT

GCTGCCCATCCTGCACCAGGACTGGCTGAAGGGCAAGGAGTTCAAGTGCA

AGGTGAACAGCAAGAGCCTGCCCAGCGCCATGGAGAGGACCATCAGCAAG

GCCAAGGGTCAGCCCCACGAGCCCCAAGTGTACGTGCTTCCCCCGACCCA

GGAGGAGTTGAGCGAGAACAAAGTGAGCGTGACCTGCCTGATCAAGGGCT

TCCACCCTCCCGACATCGCCGTGGAGTGGGAGATCACCGGCCAGCCTGAG

CCGGAAAATAACTACCAGACCACCCCTCCACAGCTGGACAGCGACGGCAC

CTACTTCCTTTACAGCAGGCTGTCTGTGGACCGAAGCCATTGGCAAAGGG

GCAACACCTACACCTGCAGCGTGAGCCACGAGGCTCTGCACAGCCACCAC

ACCCAGAAGTCTCTGACCCAGAGCCCCGGATAG
```

An exemplary nucleic acid sequence encoding the insulin-Fc fusion protein of SEQ ID NO: 36 is given below:

```
                                                (SEQ ID NO: 37)
ATGGAATGGAGCTGGGTCTTTCTCTTCTTCCTGTCAGTAACGACTGGTGT

CCACTCCTTCGTGAACCAGCACCTGTGCGGCTCCGACCTGGTGGAAGCTC

TGTATCTCGTGTGCGGCGAGCGGGCTTCTTCTACACCGATCCCACTGGA

GGCGGTCCACGCAGAGGCATCGTGGAACAGTGCTGCCACTCCATCTGCTC

CCTGTACCAGCTGGAAAACTACTGCAATGGCGGAGGTGGTTCAGGAGGCG

GTGGAGGTGAGGGCCCCAAGTGCCCCGTGCCCGAGATTCCCGGTGCCCCC

AGCGTGTTCATCTTTCCCCCAAAACCCAAGGACACCCTGAGCATCAGCAG

GACCCCCGAGGTGACCTGCCTGGTGGTGGACCTGGGACCCGACGACAGCA

ACGTGCAGATCACCTGGTTCGTGGACAACACCGAGATGCACACCGCCAAG

ACCAGGCCTCGGGAGGAGCAGTTCAAGAGCACCTACAGGGTGGTGAGCGT

GCTGCCCATCCTGCACCAGGACTGGCTGAAGGGCAAGGAGTTCAAGTGCA

AGGTGAACAGCAAGAGCCTGCCCAGCGCCATGGAGAGGACCATCAGCAAG

GCCAAGGGTCAGCCCCACGAGCCCCAAGTGTACGTGCTTCCCCCGACCCA

GGAGGAGTTGAGCGAGAACAAAGTGAGCGTGACCTGCCTGATCAAGGGCT

TCCACCCTCCCGACATCGCCGTGGAGTGGGAGATCACCGGCCAGCCTGAG

CCGGAAAATAACTACCAGACCACCCCTCCACAGCTGGACAGCGACGGCAC

CTACTTCCTTTACAGCAGGCTGTCTGTGGACCGAAGCCATTGGCAAAGGG

GCAACACCTACACCTGCAGCGTGAGCCACGAGGCTCTGCACAGCCACCAC

ACCCAGAAGTCTCTGACCCAGAGCCCCGGATAG
```

In some embodiments, the fusion protein is in a preparation. In embodiments, the preparation has a percent dimer, e.g., homodimer, of the fusion protein that is greater than about 50%, e.g., greater than about 55%, about 60%, about 65%, about 70%, about 75%, about 80%, about 85%, about 90%, 95% or about 100%. In embodiments, the percent dimer, e.g., homodimer, of the fusion protein preparation is 91%, 92%, 93%, 94%, 95%, 96%, 97%, 98%, 99% or 100%. In embodiments, the percent homodimer is about 70% or higher (e.g., 80%, 85%, or 88% or more) and can be made 90% or higher (e.g., 95%, 97%, 98%, 99% or nearly 100%) using one or more processing steps (e.g., ion exchange chromatography, gel filtration, hydrophobic interaction chromatography, etc.). In some embodiments, the % dimer, e.g., homodimer, in the preparation is determined by size-exclusion chromatography which is an analytical separation method that can discriminate between dimers, e.g., homodimers, and higher-order non-covalent Fc fusion protein aggregates (e.g., multimers). In some embodiments, the % dimer is determined to be greater than 95%, e.g., as determined by size-exclusion chromatography. In some embodiments, the % dimer, e.g., homodimer, is determined to be greater than 99%, e.g., as determined by size-exclusion chromatography. In some embodiments, insulin-Fc fusion proteins with substantially greater homodimer content than other insulin-Fc fusion proteins demonstrate more bioactivity in a subject (e.g., a cat).

Fusion Protein Production

In embodiments, a fusion protein can be expressed by a vector as described in the Examples section.

Expression and Purification

In embodiments, a fusion protein can be expressed recombinantly, e.g., in a eukaryotic cell, e.g., mammalian cell or non-mammalian cell. Exemplary mammalian cells used for expression include HEK cells, e.g., HEK293 cells, or CHO cells. In embodiments, cells are transfected with a nucleic acid molecule, e.g., vector, encoding the fusion protein (e.g., where the entire fusion protein is encoded by a single nucleic acid molecule). In other embodiments, cells are transfected with more than one nucleic acid molecule, where each nucleic acid molecule encodes a different domain of the fusion protein. For example, one nucleic acid molecule can encode the insulin polypeptide, and a different nucleic acid molecule can encode the Fc fragment. Cells can be cultured using standard methods in the art.

In some embodiments, the fusion protein is purified or isolated from the cells (e.g., by lysis of the cells). In other embodiments, the fusion protein is secreted by the cells and, e.g., the fusion protein is purified or isolated from the cell culture media in which the cells were grown. Purification of the fusion protein can include using column chromatography, e.g., affinity chromatography, or using other separation methods that involve size, charge, and/or affinity for certain molecules. In embodiments, purification of the fusion protein involves selecting or enriching for proteins with an Fc fragment, e.g., by using Protein A beads or a Protein A column that cause proteins containing an Fc fragment to become bound with high affinity at neutral solution pH to the Protein A covalently conjugated to the Protein A beads. The bound Fc fusion protein may then be eluted from the Protein A beads by a change in a solution variable (e.g., a decrease in the solution pH). Other separation methods such as ion exchange chromatography and/or gel filtration chromatography can also be employed alternatively or in addition. In embodiments, purification of the fusion protein further comprises filtering or centrifuging the protein preparation. In embodiments, further purification of the fusion protein comprises diafiltration, ultrafiltration, and filtration through porous membranes of various sizes, as well as final formulation with excipients.

The purified fusion protein can be characterized, e.g., for purity, yield, structure, and/or activity, using a variety of methods, e.g., absorbance at 280 nm (e.g., to determine yield), size exclusion or capillary electrophoresis (e.g., to determine the molecular weight, percent aggregation, and/or purity), mass spectrometry (MS) and/or liquid chromatography (LC-MS) (e.g., to determine purity and/or glycosylation), and/or ELISA (e.g., to determine extent of binding, e.g., affinity, to an anti-insulin antibody). Exemplary methods of characterization are also described in the Examples section.

Functional Features of Fusion Proteins

Described herein are methods for treating diabetes (e.g., feline diabetes), the methods comprising the administration of a fusion protein (e.g., a fusion protein described herein) to a subject. In embodiments, a fusion protein described herein is capable of lowering glucose levels (e.g., blood glucose levels) after administration in a subject. In embodiments, the glucose lowering activity of the fusion protein is greater than that of an insulin reference standard. In some embodiments, the duration of activity of the fusion protein can be measured by a decrease, e.g., a statistically significant decrease, in blood glucose relative to a pre-dose glucose level. In embodiments, the fusion protein is long-acting (e.g., has a long half-life, e.g., in serum). In embodiments, the serum half-life of the fusion protein (e.g., in the blood of a subject upon administration) is longer than about 2 hours. In embodiments, the serum half-life of the fusion protein is 4 days, or longer. In embodiments, the serum half-life of the fusion protein is longer than that of an insulin reference standard or control formulation.

In embodiments, the duration of activity of the fusion protein (e.g., the time during which there is a statistically significant decrease in blood glucose level in a subject relative to a pre-dose level) is longer than about 2 hours. In embodiments, the duration of activity of the fusion protein (e.g., the time during which there is a statistically significant decrease in blood glucose level in a subject relative to a pre-dose level) is longer than about 6 hours, 9 hours, 12 hours, 18 hours, 1 day, 1.5 days, 2 days, 2.5 days, 3 days, 4 days, 5 days or longer. In embodiments, the duration of activity of the fusion protein (e.g., the time during which there is a statistically significant decrease in blood glucose level in a subject relative to a pre-dose level) is longer than that of an insulin reference standard or control formulation.

Methods of Treatment and Characteristics of Subject Selection

Described herein are methods for interacting with the insulin receptors to lower blood glucose in felines, wherein the method comprises administering to a subject a fusion protein, e.g., a fusion protein described herein. In some embodiments, the subject has been diagnosed with diabetes (e.g., feline diabetes).

In embodiments, a reference standard used in any method described herein comprises a reference treatment or reference therapy. In some embodiments, the reference comprises a standard of care agent for diabetes treatment (e.g., a standard of care agent for feline diabetes). In some embodiments, the reference standard is a commercially available insulin or insulin analog. In some embodiments, the reference standard comprises a long-lasting insulin, intermediate-lasting insulin, short-lasting insulin, rapid-acting insulin, short-acting, intermediate-acting, long-acting insulin. In some embodiments, the reference standard comprises Vetsulin®, Prozinc®, insulin NPH, insulin glargine (Lantus®), or recombinant human insulin.

In embodiments, a reference standard used in any method described herein includes an outcome, e.g., outcome described herein, of a diabetes therapy (e.g., a feline diabetes therapy).

In embodiments, a reference standard is a level of a marker (e.g., blood glucose or fructosamine) in the subject prior to initiation of a therapy, e.g., a fusion protein therapy described herein; where the subject has diabetes. In embodiments, the blood glucose level in a cat is greater than 200 mg/dL (e.g., greater than 250 mg/dL, 300 mg/dL, 350 mg/dL, 400 mg/dL or more) prior to initiation of therapy. In embodiments, the fructosamine level in a cat is greater than 250 micromol/L, 350 micromol/L (e.g., greater than 400 micromol/L, 450 micromol/L, 500 micromol/L, 550 micromol/L, 600 micromol/L, 650 micromol/L, 700 micromol/L, 750 micromol/L or more) prior to initiation of therapy. In embodiments, a reference standard is a measure of the presence of or the progression of or the severity of the disease. In embodiments, a reference standard is a measure of the presence of or the severity of the disease symptoms prior to initiation of a therapy, e.g., a fusion protein therapy described herein, e.g., where the subject has diabetes.

Pharmaceutical Compositions and Routes of Administration

Provided herein are pharmaceutical compositions containing a fusion protein described herein that can be used to lower blood glucose in cats. The amount and concentration of the fusion protein in the pharmaceutical compositions, as well as the quantity of the pharmaceutical composition administered to a subject, can be selected based on clinically relevant factors, such as medically relevant characteristics of the subject (e.g. age, weight, gender, other medical conditions, and the like), the solubility of compounds in the pharmaceutical compositions, the potency and activity of the compounds, and the manner of administration of the pharmaceutical compositions.

Formulations of the present disclosure include those suitable for parenteral administration. The phrases "parenteral administration" and "administered parenterally" as used herein means modes of administration other than enteral and topical administration, usually by intravenous or subcutaneous injection.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, using coating materials, such as lecithin, by the maintenance of the required particle size in the case of dispersions, and using surfactants, e.g., Tween- like surfactants. In some embodiments, the pharmaceutical composition (e.g., as described herein) comprises a Tween-like surfactant, e.g., Tween-20 or Tween-80. In some embodiments, the pharmaceutical composition (e.g., as described herein) comprises a Tween-like surfactant, Tween-like surfactant, e.g., poly sorbate-20, Tween-20, or Tween-80, at a concentration between about 0.001% and about 2%, or between about 0.005% and about 0.1%, or between about 0.01% and about 0.5%.

In some embodiments, the fusion protein is administered as a bolus, infusion, or an intravenous push. In some embodiments, the fusion protein is administered through syringe injection, pump, pen, needle, or indwelling catheter. Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Dosages

Actual dosage levels of the fusion protein can be varied to obtain an amount of the active ingredient that is effective to achieve the desired therapeutic response for a particular cat. The selected dosage level will depend upon a variety of factors including the activity of the particular fusion protein employed, or the ester, salt or amide thereof, the route of administration, the time of administration, the rate of excretion of the particular compound being employed, the duration of the treatment, other drugs, compounds and/or materials used in combination with the particular fusion protein employed, the age, sex, weight, condition, general health and prior medical history of the cat being treated, and like factors well known in the medical arts.

In general, a suitable dose of a fusion protein will be that amount of the fusion protein that is the lowest dose effective to produce a therapeutic effect. Such an effective dose will generally depend upon the factors described above. Generally, intravenous, and subcutaneous doses of the fusion protein for a cat will range from about 0.01 to about 10 nanomoles per kilogram of body weight per day, e.g., 0.01-10 nanomoles/kg/day, about 0.1-1 nanomoles/kg/day, about 1-10 nanomoles/kg/day, or about 0.1-10 nanomoles/kg/day. In some embodiments, the fusion protein is administered at a dose greater than or equal to 3 nmol/kg/day (e.g., greater than 4, 5, 6, 10, 20, 30, 40, 50, or 60 nmol/kg/day). In still other embodiments, the fusion protein is administered at a dose between 0.6-60 nanomoles per kilogram of body weight per week, or 0.6-6 nanomoles/kg/week.

The present disclosure contemplates formulation of the fusion protein in any of the aforementioned pharmaceutical compositions and preparations. Furthermore, the present disclosure contemplates administration via any of the foregoing routes of administration. One of skill in the art can select the appropriate formulation and route of administration based on the condition being treated and the overall health, age, and size of the patient being treated.

EXAMPLES

The present technology is further illustrated by the following Examples, which should not be construed as limiting in any way.

GENERAL METHODS, ASSAYS, AND MATERIALS

Example 1: Synthesis and Methods of Making an Insulin-Fc Fusion Protein in HEK293 Cells Insulin-Fc fusion proteins were synthesized as follows. A gene sequence of interest was constructed using proprietary software (LakePharma, Belmont, CA) and was cloned into a high expression mammalian vector. HEK293 cells were seeded in a shake flask 24 hours before transfection and were grown using serum-free chemically defined media. A DNA expression construct that encodes the insulin-Fc fusion protein of interest was transiently transfected into a suspension of HEK293 cells using the (LakePharma, Belmont, CA) standard operating procedure for transient transfection. After 20 hours, the cells were counted to determine the viability and viable cell count, and the titer was measured by FortéBio® Octet® (Pall FortéBio LLC, Fremont, CA). Additional readings were taken throughout the transient transfection production run. The culture was harvested on or after Day 5.

Example 2: Synthesis and Methods of Making an Insulin-Fc Fusion Protein in HEK293 Cells Insulin-Fc fusion proteins are synthesized as follows. A gene sequence of interest is constructed using proprietary software (LakePharma, Belmont, CA) and is cloned into a high expression mammalian vector. HEK293 cells are seeded in a shake flask 24 hours before transfection and are grown using serum-free chemically defined media. A DNA expression construct that encodes the insulin-Fc fusion protein of interest is transiently transfected into a suspension of HEK293 cells using the (LakePharma, Belmont, CA) standard operating procedure for transient transfection. After 20 hours, the cells are counted to determine the viability and viable cell count, and the titer is measured by FortéBio® Octet® (Pall FortéBio LLC, Fremont, CA). Additional readings are taken throughout the transient transfection production run. The culture is harvested on or after Day 5.

Example 3: Purification of an Insulin-Fc Fusion Protein

Purification of an insulin-Fc fusion protein was performed as follows. Conditioned media supernatants containing the secreted insulin-Fc fusion protein were harvested from the transiently or stably transfected HEK production runs and were clarified by centrifugation. The supernatant containing the desired insulin-Fc fusion protein was run over a Protein A or a Protein G column and eluted using a low pH gradient. Optionally, recovery of the insulin-Fc fusion proteins could be enhanced by reloading of the initial Protein A or Protein G column eluent again onto a second Protein A or Protein G column. Afterwards, the eluted fractions containing the desired protein were pooled and buffer exchanged into 200 mM HEPES, 100 mM NaCl, 50 mM NaOAc, pH 7.0 buffer. A final filtration step was performed using a 0.2 μm membrane filter. The final protein concentration was calculated from the solution optical density at 280 nm. Further optional purification by ion-exchange chromatography (e.g., using an anion exchange bead resin or a cation exchange bead resin), gel filtration chromatography, or other methods was performed, as necessary.

Example 4: Purification of an Insulin-Fc Fusion Protein

Purification of an insulin-Fc fusion protein is performed as follows. Conditioned media supernatants containing the secreted insulin-Fc fusion protein are harvested from the transiently or stably transfected HEK production runs and are clarified by centrifugation. The supernatant containing the desired insulin-Fc fusion protein is run over a Protein A or a Protein G column and eluted using a low pH gradient. Optionally, recovery of the insulin-Fc fusion proteins can be enhanced by reloading of the initial Protein A or Protein G column eluent again onto a second Protein A or Protein G column. Afterwards, the eluted fractions containing the desired protein are pooled and buffer exchanged into 200 mM HEPES, 100 mM NaCl, 50 mM NaOAc, pH 7.0 buffer. A final filtration step is performed using a 0.2 μm membrane filter. The final protein concentration is calculated from the solution optical density at 280 nm. Further optional purification by ion-exchange chromatography (e.g., using an anion exchange bead resin or a cation exchange bead resin), gel filtration chromatography, or other methods is performed, as necessary.

Example 5: Structure Confirmation by Non-Reducing and Reducing CE-SDS

Capillary electrophoresis sodium dodecyl sulfate (CE-SDS) analysis was performed in a LabChip® GXII (Perkin Elmer, Waltham, MA) on a solution of a purified insulin-Fc fusion protein dissolved in 200 mM HEPES, 100 mM NaCl, 50 mM NaOAc, pH 7.0 buffer, and the electropherogram was plotted. Under non-reducing conditions, the sample was run against known molecular weight (MW) protein standards, and the eluting peak represented the 'apparent' MW of the insulin-Fc fusion protein homodimer.

Under reducing conditions (e.g., using beta-mercaptoethanol to break disulfide bonds of the insulin-Fc fusion homodimer), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

Example 6: Structure Confirmation by Non-Reducing and Reducing CE-SDS

Capillary electrophoresis sodium dodecyl sulfate (CE-SDS) analysis is performed in a LabChip® GXII (Perkin Elmer, Waltham, MA) on a solution of a purified insulin-Fc fusion protein dissolved in 200 mM HEPES, 100 mM NaCl, 50 mM NaOAc, pH 7.0 buffer, and the electropherogram is plotted. Under non-reducing conditions, the sample is run against known molecular weight (MW) protein standards, and the eluting peak represents the 'apparent' MW of the insulin-Fc fusion protein homodimer.

Under reducing conditions (e.g., using beta-mercaptoethanol to break disulfide bonds of the insulin-Fc fusion homodimer), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

Example 7: Sequence Identification by LC-MS With Glycan Removal

To obtain an accurate estimate of the insulin-Fc mass via mass spectroscopy (MS), the sample was first treated to remove naturally occurring glycan that might interfere with the MS analysis. 100 μL of a 2.5 mg/mL insulin-Fc fusion protein dissolved in 200 mM HEPES, 100 mM NaCl, 50 mM NaOAc, pH 7.0 buffer solution was first buffer exchanged into 0.1 M Tris, pH 8.0 buffer containing 5 mM EDTA using a Zeba desalting column (Pierce, ThermoFisher Scientific, Waltham, MA). 1.67 μL of PNGase F enzyme (Prozyme N-glycanase) was added to this solution to remove N-linked glycan present in the fusion protein (e.g., glycan linked to the side chain of the asparagine located at the cNg-N site), and the mixture was incubated at 37° C. overnight in an incubator. The sample was then analyzed via LC-MS (NovaBioassays, Woburn, MA) resulting in a molecular mass of the molecule which corresponds to the desired homodimer without the glycan. This mass was then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for the enzymatic modification of the insulin-Fc fusion protein structure in the analytical sample.

Example 8: Sequence Identification by LC-MS with Glycan Removal

To obtain an accurate estimate of the insulin-Fc mass via mass spectroscopy (MS), the sample is first treated to remove naturally occurring glycan that might interfere with the MS analysis. 100 μL of a 2.5 mg/mL insulin-Fc fusion protein dissolved in 200 mM HEPES, 100 mM NaCl, 50 mM NaOAc, pH 7.0 buffer solution is first buffer exchanged into 0.1 M Tris, pH 8.0 buffer containing 5 mM EDTA using a Zeba desalting column (Pierce, ThermoFisher Scientific, Waltham, MA). 1.67 μL of PNGase F enzyme (Prozyme N-glycanase) is added to this solution to remove N-linked glycan present in the fusion protein (e.g., glycan linked to the side chain of the asparagine located at the cNg-N site), and the mixture is incubated at 37° C. overnight in an incubator. The sample is then analyzed via LC-MS (NovaBioassays, Woburn, MA) resulting in a molecular mass of the molecule which corresponds to the desired homodimer without the glycan. This mass is then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for the enzymatic modification of the insulin-Fc fusion protein structure in the analytical sample.

Example 9: % Homodimer by Size-Exclusion Chromatography

Size-exclusion chromatography (SEC-HPLC) of insulin-Fc fusion proteins was carried out using a Waters 2795HT HPLC (Waters Corporation, Milford, MA) connected to a 2998 Photodiode array at a wavelength of 280 nm. 100 μL or less of a sample containing an insulin-Fc fusion protein of interest was injected into a MAbPac SEC-1, 5 μm, 4×300 mm column (ThermoFisher Scientific, Waltham, MA) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g., multimers of insulin-Fc fusion protein homodimers) eluted at earlier retention times, and the non-aggregated homodimers eluted at later retention times. In separating the mixture of homodimers from aggregated multimeric homodimers via analytical SEC-HPLC, the purity of the insulin-Fc fusion protein solution in terms of the percentage of non-aggregated homodimer was ascertained.

Example 10: % Homodimer by Size-Exclusion Chromatography

Size-exclusion chromatography (SEC-HPLC) of insulin-Fc fusion proteins is carried out using a Waters 2795HT HPLC (Waters Corporation, Milford, MA) connected to a 2998 Photodiode array at a wavelength of 280 nm. 100 μL or less of a sample containing an insulin-Fc fusion protein of interest is injected into a MAbPac SEC-1, 5 μm, 4×300 mm column (ThermoFisher Scientific, Waltham, MA) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g., multimers of insulin-Fc fusion protein homodimers) elute at earlier retention times, and the non-aggregated homodimers elute at later retention times. In separating the mixture of homodimers from aggregated multimeric homodimers via analytical SEC-HPLC, the purity of the insulin-Fc fusion protein solution in terms of the percentage of non-aggregated homodimer is ascertained.

Example 11: In Vitro IM-9 Insulin Receptor Binding of an Exemplary Insulin-Fc Fusion Protein at 4° C.

Human IM-9 cells (ATTC #CCL-159) that express human insulin receptor were cultured and maintained in complete RPMI 5% FBS medium at 70-80% confluency. Cultures of IM-9 cells were centrifuged at 250×g (~1000 rpm) for 10 min to pellet the cells. Cells were washed once with HBSS or PBS buffer, resuspended in cold FACS staining medium (HBSS/2 mM EDTA/0.1% Na-azide+4% horse serum) to a concentration of 8×106 cells/mL and kept on ice or 4° C. until test solutions were made. The insulin-Fc protein was diluted in FACS buffer in 1:3 serial dilutions as 2× concentrations in 1.2 mL tubes (approx. 60 μL volume of each dilution), and the solutions were kept cold on ice until ready for pipetting.

Biotinylated-RHI was diluted in FACS staining medium to a concentration of 1.25 μg/mL. 40 μL of the serially diluted test compound and 8 μL of 1.25 μg/mL Biotin-RHI were added into each well of a V bottom microtiter plate, mixed by slow vortexing, and placed on ice. 40 μL of an IM-9 cell suspension (8×106 cells/mL) was then added to each well by multichannel pipette, mixed again gently and incubated on ice for 30 min to allow competitive binding on the insulin receptor on IM-9 cells. Cells were then washed twice with 275 μL of ice-cold FACS wash buffer (HBSS/2 mM EDTA/0.1% Na-azide+0.5% horse serum) by centrifuging the V-bottom plate at 3000 rpm for 3 min and aspirating the supernatant. Cells were then resuspended in 40 μL of FACS staining medium containing 1:100 diluted Streptavidin-PE (Life Technologies) for 20 min on ice. Cells were then washed once with 275 μL of ice-cold FACS buffer and finally fixed with 3% paraformaldehyde for 10 min at room temp. Cells were then washed once with 275 μL of ice-cold FACS buffer and resuspended in 250 μl of FACS buffer for analysis.

The V-bottom plates containing cells were then analyzed on a Guava 8-HT flow cytometer (Millipore). Biotinylated-RHI binding to insulin receptor was quantitated by the median fluorescence intensity (MFI) of the cells on the FACS FL-2 channel for each concentration of the test compound. Control wells were labeled only with biotinylated-RHI and were used to calculate the percent (%) inhibition resulting from each test compound concentration. The % inhibition by test compounds of biotinylated-RHI binding on IM-9 cells was plotted against log concentrations of the test compound, and the resulting IC50 values were calculated using GraphPad Prism (GraphPad Software, La Jolla, CA) for the test compounds. Lower IC50 values of the test compound therefore indicate greater levels of biotinylated-RHI inhibition at lower concentrations indicating stronger binding of the insulin-Fc fusion protein to the insulin receptor. A control compound, such as unlabeled recombinant human insulin (RHI) was also used as an internal standard to generate an RHI IC50 against which a given compound IC50 could be ratioed (IC50(compound)/IC50(RHI)). Lower IC50 ratios have more similar binding to RHI (stronger binding to insulin receptor), while higher IC50 ratios have weaker binding to the insulin receptor relative to RHI.

Example 12: In Vitro Fc(Gamma) Receptor I Binding Affinity Assay

The binding of insulin-Fc fusion proteins to the Fc(gamma) receptor I at pH 7.4 was conducted using an ELISA assay as follows. Since canine Fc(gamma) receptor I was not commercially available, human Fc(gamma) receptor I (i.e., rhFc(gamma) receptor I) was used as a surrogate mammalian receptor. Insulin-Fc compounds were diluted to 10 μg/mL in sodium bicarbonate buffer at pH 9.6 and coated on Maxisorp (Nunc) microtiter plates overnight at 4° C., after which the microplate strips were washed 5 times with PBST (PBS/0.05% Tween-20) buffer and blocked with Superblock blocking reagent (ThermoFisher). Serial dilutions of biotinylated rhFc(gamma) receptor I (recombinant human Fc(gamma)R-I; R&D Systems) were prepared in PBST/10% Superblock buffer from 6000 ng/mL to 8.2 ng/mL and loaded at 100 μL/well onto the microplate strips coated with insulin-Fc fusion protein. The microtiter plate was incubated for 1 hour at room temperature after which the microplate strips were washed 5 times with PBST and then loaded with 100 μL/well of streptavidin-HRP diluted 1:10000 in PBST/10% Superblock buffer. After incubating for 45 min, the microplate strips were washed again 5 times with PBST. TMB was added to reveal the bound Fc(gamma) receptor I proteins and stopped with ELISA stop reagent (Boston Bioproducts). The plate was read in an ELISA plate reader at 450 nm, and the OD values (proportional to the binding of rhFc(gamma) receptor I to insulin-Fc protein) were plotted against log concentrations of rhFc(gamma) receptor I added to each well to generate binding curves using GraphPad Prism software.

Example 13: Generalized Procedure for Determination of In Vivo Pharmacodynamics (PD) After Single Administration of Insulin Fc-Fusion Proteins in Dogs Insulin-Fc fusion proteins were assessed for their effects on fasting blood glucose levels as follows. N=1, 2, 3 or more healthy, antibody-naïve, dogs weighing approximately 10-15 kg were used, one for each insulin-Fc fusion protein. Dogs were also observed twice daily for signs of anaphylaxis, lethargy, distress, pain, etc., and, optionally for some compounds, treatment was continued for an additional three weekly subcutaneous injections or more to observe if the glucose lowering capability of the compounds lessened over time, a key sign of potential induction of neutralizing anti-drug antibodies. On Day 0, the dogs received a single injection either via intravenous or subcutaneous administration of a pharmaceutical composition containing an insulin Fc-fusion protein homodimer at a concentration between 1 and 10 mg/mL in a solution of between 10-50 mM sodium hydrogen phosphate, 50-150 mM sodium chloride, 0.005-

0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On Day 0, blood was collected from a suitable vein immediately prior to injection and at 15, 30, 45, 60, 120, 240, 360, and 480 min and at 1, 2, 3, 4, 5, 6 and 7 days post injection.

For each time point, a minimum of 1 mL of whole blood was collected. A glucose level reading was immediately determined using a glucose meter (ACCU-CHEK® Aviva Plus), which required approximately one drop of blood. Average % fasting blood glucose levels (% FBGL) from Day 0 to Day 7 were plotted to assess the bioactivity of a given insulin-Fc fusion protein.

Example 14: Generalized Procedure for Determination of In Vivo Pharmacodynamics (PD) After Single Administration of Insulin Fc-Fusion Proteins in Dogs Insulin-Fc fusion proteins are assessed for their effects on fasting blood glucose levels as follows. N=1, 2, 3 or more healthy, antibody-naïve, dogs weighing approximately 10-15 kg are used, one for each insulin-Fc fusion protein. Dogs are also observed twice daily for signs of anaphylaxis, lethargy, distress, pain, etc., and, optionally for some compounds, treatment is continued for an additional three weekly subcutaneous injections or more to observe if the glucose lowering capability of the compounds lessened over time, a key sign of potential induction of neutralizing anti-drug antibodies. On Day 0, the dogs receive a single injection either via intravenous or subcutaneous administration of a pharmaceutical composition containing an insulin Fc-fusion protein homodimer at a concentration between 1 and 10 mg/mL in a solution of between 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On Day 0, blood is collected from a suitable vein immediately prior to injection and at 15, 30, 45, 60, 120, 240, 360, and 480 min and at 1, 2, 3, 4, 5, 6 and 7 days post injection.

For each time point, a minimum of 1 mL of whole blood is collected. A glucose level reading is immediately determined using a glucose meter (ACCU-CHEK® Aviva Plus), which requires approximately one drop of blood. Average % fasting blood glucose levels (% FBGL) from Day 0 to Day 7 are plotted to assess the bioactivity of a given insulin-Fc fusion protein.

Example 15: Generalized Procedure for Determination of In Vivo Pharmacodynamics (PD) After Repeated Administration of Insulin-Fc Fusion Proteins in Canines Insulin-Fc fusion proteins were assessed for their effects on blood glucose levels over repeated injections as follows. Healthy, antibody-naïve, dogs weighing approximately between 5 and 20 kg were used, and each animal was administered doses of an insulin-Fc fusion protein. Animals were observed twice daily for signs of anaphylaxis, lethargy, distress, pain, and other negative side effects, and optionally for some compounds, treatment was continued for up to an additional two to five subcutaneous injections to observe if the glucose lowering capability of the compounds decreased over time, indicating the possible presence of neutralizing anti-drug antibodies in vivo. On Day 0, the animals received a single subcutaneous injection of a pharmaceutical composition containing an insulin Fc-fusion protein in a solution of 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On Day 0, blood was collected from a suitable vein immediately prior to injection and at 15, 30, 45, 60, 120, 240, 360, and 480 min and at 1, 2, 3, 4, 5, 6 and 7 days post injection.

Subsequent subcutaneous injections were given no more frequently than once-weekly, and in some cases the injections were given at different intervals based on the pharmacodynamics of a given insulin-Fc fusion protein formulation. Subsequent injections for each insulin-Fc fusion protein were adjusted to higher or lower doses, depending on the demonstrated pharmacodynamics of the insulin-Fc fusion protein. For instance, if the dose of a first injection on Day 0 was found to be ineffective at lowering blood glucose, the subsequent dose levels of injected insulin-Fc fusion protein were adjusted upward. In a similar manner, if the dose of a first injection on Day 0 was found to lower glucose in too strong a manner, then subsequent dose levels of injected insulin-Fc fusion protein were adjusted downward. It was also found that interim doses or final doses could be adjusted in a similar manner as needed. For each dose, blood was collected from a suitable vein just immediately prior to injection and at 15, 30, 45, 60, 120, 240, 360, and 480 min and at 1, 2, 3, 4, 5, 6, 7 days (and optionally 14 days) post injection. For each time point, a minimum of 1 mL of whole blood was collected. A glucose level reading was immediately determined using a glucose meter (ACCU-CHEK® Aviva Plus), which required approximately one drop of blood. Average % fasting blood glucose levels (% FBGL) from throughout the study were plotted against time which allows the bioactivity of a fusion protein to be determined.

To determine the bioactivity of each dose, an area-over-the-curve (AOC) analysis was conducted as follows. After constructing the % FBGL versus time data, the data was then entered into data analysis software (GraphPad Prism, GraphPad Software, San Diego CA). The software was used to first conduct an area-under-the curve analysis (AUC) to integrate the area under the % FBGL vs. time curve for each dose. To convert the AUC data into the desired AOC data, the following equation was used: AOC=TPA−AUC; where TPA is the total possible area obtained by multiplying each dose lifetime (e.g., 7 days, 14 days, etc.) by 100% (where 100% represents the y=100% of the % FBGL vs. time curve). For example, given a dose lifetime of 7 days and a calculated AUC of 500% FBGL days, gives the following for AOC: AOC=(100% FBGL×7 days)−(500% FBGL·days)=200% FBGL days. The analysis can be performed for each injected dose in a series of injected doses to obtain the AOC values for injection 1, injection 2, injection 3, etc.

As the doses of insulin-Fc fusion protein may vary as previously discussed, it is often more convenient to normalize all calculated AOC values for a given insulin-Fc fusion protein to a particular dose of that insulin-Fc fusion protein. Doing so allows for convenient comparison of the glucose-lowering potency of an insulin-Fc fusion protein across multiple injections, even if the dose levels change across the injections of a given study. Normalized AOC (NAOC) for a given dose is calculated as follows: NAOC=AOC/D with units of % FBGL·days·kg/mg; where D is the actual dose injected into the animal in mg/kg. NAOC values may be calculated for each injection in a series of injections for a given animal and may be averaged across a group of animals receiving the same insulin-Fc fusion protein formulation.

The NAOC ratio (NAOCR) may also be calculated for each injection in a series of injections for a given animal by taking the NAOC values for each injection (e.g., injections 1, 2, 3 . . . N) and dividing each NAOC for a given injection by the NAOC from injection 1 as follows: NAOCR=(NAOC (Nth injection)/NAOC(injection 1)). By evaluating the NAOCR of a given insulin-Fc homodimer fusion protein formulation for the Nth injection in a series of injections, it is possible to determine whether the in vivo glucose lowering activity of a given insulin-Fc fusion protein has substantially retained its bioactivity over a series of N doses (e.g., NAOCR for the Nth dose of greater than 0.5) or whether the in vivo glucose lowering activity of a given insulin-Fc fusion protein has lost a substantial portion of its potency (e.g., NAOCR of the Nth dose is less than 0.5) over a course of N doses, indicating the potential formation of neutralizing anti-drug antibodies in vivo. In preferred embodiments, the ratio of NAOC following the third subcutaneous injection to the NAOC following the first subcutaneous injection is greater than 0.5 (i.e., the NAOCR of the third subcutaneous injection is greater than 0.5).

Example 16: Generalized Procedure for Determination of In Vivo Pharmacodynamics (PD) After Repeated Administration of Insulin-Fc Fusion Proteins in Canines Insulin-Fc fusion proteins are assessed for their effects on blood glucose levels over repeated injections as follows. Healthy, antibody-naïve, dogs weighing approximately between 5 and 20 kg are used, and each dog is administered doses of an insulin-Fc fusion protein. Dogs are observed twice daily for signs of anaphylaxis, lethargy, distress, pain, and other negative side effects, and optionally for some compounds, treatment is continued for up to an additional two to five subcutaneous injections to observe if the glucose lowering capability of the compounds decreases over time, indicating the possible presence of neutralizing anti-drug antibodies in vivo. On Day 0, the animals receive a single subcutaneous injection of a pharmaceutical composition containing an insulin Fc-fusion protein in a solution of 10-50 mM sodium hydrogen phosphate, 50-150 mM sodium chloride, 0.005-0.05% v/v Tween-80, and optionally a bacteriostat (e.g. phenol, m-cresol, or methylparaben) at a concentration of between 0.02-1.00 mg/mL, at a solution pH of between 7.0-8.0, at a dose of 0.08-0.80 mg insulin-Fc fusion protein/kg (or approximately equivalent to 1.2-12.3 nmol/kg or approximately equivalent to 0.4-4.0 U/kg insulin equivalent on molar basis). On Day 0, blood is collected from a suitable vein immediately prior to injection and at 15, 30, 45, 60, 120, 240, 360, and 480 min and at 1, 2, 3, 4, 5, 6 and 7 days post injection.

Subsequent subcutaneous injections are given no more frequently than once-weekly, and in some cases the injections are given at different intervals based on the pharmacodynamics of a given insulin-Fc fusion protein formulation. Subsequent injections for each insulin-Fc fusion protein are adjusted to higher or lower doses, depending on the demonstrated pharmacodynamics of the insulin-Fc fusion protein. For instance, if the dose of a first injection on Day 0 is found to be ineffective at lowering blood glucose, the subsequent dose levels of injected insulin-Fc fusion protein are adjusted upward. In a similar manner, if the dose of a first injection on Day 0 was found to lower glucose in too strong a manner, then subsequent dose levels of injected insulin-Fc fusion protein are adjusted downward. Interim doses or final doses can be adjusted in a similar manner as needed. For each dose, blood is collected from a suitable vein just immediately prior to injection and at 15, 30, 45, 60, 120, 240, 360, and 480 min and at 1, 2, 3, 4, 5, 6, 7 days (and optionally 14 days) post injection. For each time point, a minimum of 1 mL of whole blood is collected. A glucose level reading is immediately determined using a glucose meter (ACCU-CHEK® Aviva Plus), which requires approximately one drop of blood. Average % fasting blood glucose levels (% FBGL) from throughout the study are plotted against time which allows the bioactivity of a fusion protein to be determined.

To determine the bioactivity of each dose, an area-over-the-curve (AOC) analysis is conducted as follows. After constructing the % FBGL versus time data, the data is then entered into data analysis software (GraphPad Prism, GraphPad Software, San Diego CA). The software is used to first conduct an area-under-the curve analysis (AUC) to integrate the area under the % FBGL vs. time curve for each dose. To convert the AUC data into the desired AOC data, the following equation is used: AOC=TPA−AUC; where TPA is the total possible area obtained by multiplying each dose lifetime (e.g., 7 days, 14 days, etc.) by 100% (where 100% represents the y=100% of the % FBGL vs. time curve). For example, given a dose lifetime of 7 days and a calculated AUC of 500% FBGL days, gives the following for AOC: AOC=(100% FBGL×7 days)−(500% FBGL days)=200% FBGL days. The analysis can be performed for each injected dose in a series of injected doses to obtain the AOC values for injection 1, injection 2, injection 3, etc.

As the doses of insulin-Fc fusion protein may vary as previously discussed, it is often more convenient to normalize all calculated AOC values for a given insulin-Fc fusion protein to a particular dose of that insulin-Fc fusion protein. Doing so allows for convenient comparison of the glucose-lowering potency of an insulin-Fc fusion protein across multiple injections, even if the dose levels change across the injections of a given study. Normalized AOC (NAOC) for a given dose is calculated as follows: NAOC=AOC/D with units of % FBGL·days·kg/mg; where D is the actual dose injected into the animal in mg/kg. NAOC values may be calculated for each injection in a series of injections for a given animal and may be averaged across a group of animals receiving the same insulin-Fc fusion protein formulation.

The NAOC ratio (NAOCR) may also be calculated for each injection in a series of injections for a given animal by taking the NAOC values for each injection (e.g., injections 1, 2, 3 . . . N) and dividing each NAOC for a given injection by the NAOC from injection 1 as follows: NAOCR=(NAOC (Nth injection)/NAOC(injection 1)). By evaluating the NAOCR of a given insulin-Fc homodimer fusion protein formulation for the Nth injection in a series of injections, it is possible to determine whether the in vivo glucose lowering activity of a given insulin-Fc fusion protein has substantially retained its bioactivity over a series of N doses (e.g., NAOCR for the Nth dose of greater than 0.5) or whether the in vivo glucose lowering activity of a given insulin-Fc fusion protein has lost a substantial portion of its potency (e.g., NAOCR of the Nth dose is less than 0.5) over a course of N doses, indicating the potential formation of neutralizing anti-drug antibodies in vivo. In preferred embodiments, the ratio of NAOC following the third subcutaneous injection to the NAOC following the first subcutaneous injection is greater than 0.5 (i.e., the NAOCR of the third subcutaneous injection is greater than 0.5).

Example 17: Assay Protocol for Measuring Anti-Drug Antibodies in Canine Serum

Maxisorp ELISA Plates (Nunc) are coated with the insulin-Fc fusion protein of interest diluted in coating buffer (pH=9.6 Carbonate-Biocarbonate buffer) at 10 μg/mL overnight at 4° C. for measuring ADAs against the test compound. For measuring ADAs against the insulin portion of the insulin-Fc fusion protein containing an Fc fragment of canine IgG origin, plates are coated with purified insulin at 30 μg/mL in coating buffer. Plates are then washed 5× with PBST (PBS+0.05% Tween 20) and blocked for at least 1 hour (or overnight) with SuperBlock blocking solution (ThermoFisher, Waltham MA). For calculating the ADAs in canine IgG units, strips are directly coated with 1:2 serial dilutions of canine IgG (Jackson Immunoresearch Laboratories, West Grove PA) in pH=9.6 Carb-Biocarb coating buffer at concentrations between 300-4.69 ng/ml overnight at 4° C. and used to create a 7-point pseudo-standard curve. The standards strip plates are also washed and blocked with SuperBlock blocking solution for at least 1 hour (or overnight).

Test serum samples are diluted to greater than or equal to 1:100 (typically tested as 1:200) in PBST/SB/20% HS sample dilution buffer (PBS+0.1% Tween 20+10% SuperBlock+20% horse serum) and added to the insulin-Fc fusion protein coated (or RHI coated) strips at 100 μL/well in duplicate. Duplicate strips of canine IgG coated standard strips are also added to each plate and filled with PBST/SB (PBS+0.1% Tween 20+10% SuperBlock) buffer at 100 μL/well. Plates are incubated for 1 hour at RT and then washed 5× with PBST. For detection of ADAs, HRP-conjugated Goat anti-feline IgG F(ab')2 (anti-feline IgG F(ab')2 reagent is cross-reacted to canine antibodies; Jackson Immunoresearch Laboratories, West Grove PA), which is diluted in PBST/SB to 1:10000 and added at 100 μL/well to both sample and standard wells and incubated for 45 minutes at RT in dark. Plates are washed 5× with PBST and then one time with deionized water and then developed by adding 100 μL/well TMB substrate (Invitrogen, ThermoFisher Scientific, Waltham MA) for 15-20 minutes at room temperature in the dark. Color development is then stopped by addition of 100 μL/well of ELISA Stop Solution (Boston Bioproducts) and the absorbance is read at 450 nm using a SpectraMax plate reader within 30 minutes. The anti-drug antibody concentration is determined by interpolating the OD values in the 4-PL pseudo-standard curve using SoftMax Pro Software (Molecular Devices, San Jose CA).

To demonstrate the specificity of the detected ADAs, an "inhibition" assay is carried out. In the drug inhibition ADA assay, serum samples are diluted 1:100 in PBST/SB/20% HS buffer and mixed with an equal volume of 300 μg/mL of the relevant therapeutic compound (final sample dilution at 1:200 and final inhibitory compound at 150 μg/mL) and incubated for 30-40 minutes at room temperature to allow anti-drug antibodies to bind the free inhibitor (i.e., the therapeutic compound). After pre-incubation, the samples are added to insulin-Fc fusion protein coated (or RHI coated) strips at 100 μL/well in duplicate. Samples diluted 1:200 in PBST/SB/20% HS buffer without the inhibitory compound are also tested in the sample plates along with duplicate strips of canine IgG coated standards. Remaining steps of the assay procedure are carried out as described above. The ADAs measured in the drug-inhibited wells are matched with the non-inhibited ADA concentrations to assess the specificity of the ADAs. If significant inhibition of ADA signals is observed in the drug-inhibited wells, this means the ADAs are specific to the therapeutic compound.

Example 18: Assay Procedure for Immunogenic Epitope Identification

Maxisorp ELISA microplates (Nunc) are coated with a library of insulin-Fc fusion protein homodimer compounds with known amino acid sequences, and the coated plates are blocked in a similar manner as described in the anti-drug antibody ELISA assay Example 17, except that each compound in the library is coated on a separate individual strip of ELISA microplate wells. The compounds in the library comprise a range of insulin-Fc fusion proteins with different insulin polypeptide amino acid compositions, including various B-chain, C-chain, and A-chain amino acid mutations, different linker compositions, and different Fc fragment compositions, including some of human origin. Separately, some plate strip wells are directly coated with 1:2 serial dilutions of canine IgG (Jackson Immunoresearch Laboratories, West Grove PA) for calculating the anti-drug antibodies (ADA) in canine IgG units, respectively, as described in Example 17.

Serum obtained from individual dogs receiving repeated doses of an insulin-Fc fusion protein is first screened on the anti-drug antibody ELISA assay (Example 17). Serum samples demonstrating moderate or high positivity (e.g., moderate, or high titers of antibodies) on the assay of Example 17 are serially diluted (1:200 to 1:8000) in PBST/SB/20% HS sample dilution buffer (PBS+0.1% Tween 20+10% SuperBlock+20% horse serum) and added to the plates coated with the library of insulin-Fc fusion protein compounds for 1 hour at RT. Following incubation, the plates are washed 5 times with PBST. For detection of canine antibodies capable of cross-reacting to the coated compound library, HRP conjugated goat anti-feline IgG F(ab')2 (Jackson Immunoresearch Laboratories, West Grove PA), which is cross-reactive to canine IgGs, is diluted in PBST/SB to 1:10000 and added at 100 μL/well to both sample and standard wells and incubated for 45 min at RT in the dark. Plates are washed 5 times with PBST, once with deionized water, and developed by the adding 100 μL/well TMB substrate (Invitrogen, ThermoFisher Scientific, Waltham MA) for 15-20 min at RT in the dark. Color development is then stopped by addition of 100 μL/well of ELISA Stop Solution (Boston Bioproducts, Ashland MA) and absorbance is read at 450 nm using a SpectraMax plate reader within 30 min. Anti-compound cross-reactive antibody concentrations present in the serum samples are determined by interpolating the OD values in the 4-PL pseudo-standard curve against the directly coated canine IgG antibody controls using SoftMax Pro Software (Molecular Devices, San Jose CA).

By correlating the resulting antibody concentrations from the assay with the known amino acid compositions of the coated insulin-Fc fusion protein library, one can determine whether particular amino acid mutations or epitopes are responsible for causing none, some, most, or all of the total antibody signal on the assay, indicating no binding, weak binding, or strong binding to various insulin-Fc fusion protein homodimers. The mutations or epitopes responsible for moderate or strong binding are herein referred to as immunogenic "hot spots".

Example 19: Design Process for Obtaining Insulin-Fc Fusion Proteins with High Homodimer Titers and Acceptable Levels of Acute and Repeated Dose Bioactivity in the Target Species The process for meeting the design goals described in the Detailed Description of the Invention comprised the following steps. First, the insulin polypeptide of SEQ ID NO: 4 or SEQ ID NO: 5 was combined with a species-specific Fc fragment of a particular IgG isotype and a linker such that the resulting insulin-Fc fusion protein was most likely to yield a long-acting bioactivity product with minimal immunogenicity (e.g., a species-specific IgG isotype was chosen with minimal Fc(gamma)receptor I binding). The DNA sequence coding for the desired fusion protein was prepared, cloned into a vector (LakePharma, San Carlos, CA), and the vector was then used to transiently transfect HEK cells according to the procedure described in Example 1. The insulin-Fc fusion protein was then purified according to Examples 3 and the overall protein yield and % homodimer measured according to Example 9. Only candidates with a homodimer titer of greater than 40 mg/L were considered acceptable, because titers less than this level are not likely to result in commercial production titers that meet the stringently low manufacturing cost requirements for veterinary products. Selected insulin-Fc fusion proteins were then screened for indicators of bioactivity through in vitro insulin receptor binding studies as described in Example 11. Based on experience, only compounds that exhibited IR activity IC50 values less than 5000 nM were deemed likely to exhibit bioactivity in the target species. Although the in vitro IR IC50 value is a useful qualitative screening tool, it utilizes human IM-9 cells which express the human insulin receptor and therefore it may not capture some of the small differences in affinity between the canine IR and the human IR. Furthermore, factors other than insulin receptor binding may influence a compound's bioactivity in vivo (e.g., affinity for canine FcRn to allow for extended pharmacokinetic elimination half-lives in vivo). Therefore, selected insulin-Fc fusion proteins that were acceptable from a manufacturing and IR activity IC50 value standpoint were further screened for bioactivity in the animal of interest (e.g., dog or cat) to screen out any materials with less than the desired potency and/or duration of bioactivity (e.g., NAOC of less than 150% FBGL·days·kg/mg). Again, based on experience, at NAOC values of greater than 150% FBGL·days·kg/mg, the dose requirements in the target species will be sufficiently low to reach an acceptable treatment cost. Lastly, an additional evaluation criterion was added which is mentioned rarely if ever in the art. As discussed in more detail in the Examples below, many insulin-Fc fusion protein embodiments that exhibit acceptable NAOC levels in the target species after the first dose, unexpectedly fail to maintain that level of bioactivity after repeated doses. Furthermore, in most cases the reduction in repeated dose bioactivity in the target species is correlated with the development of neutralizing anti-drug antibodies. This propensity to generate anti-drug antibodies and the failure to maintain activity render such insulin-Fc fusion proteins impractical for use in treating a chronic disease such as canine diabetes. Therefore, only the insulin-Fc fusions proteins exhibiting acceptable levels of repeated dose bioactivity (e.g., NAOCR values greater than 0.50 for the third dose relative to the first dose) with minimal levels of anti-drug antibodies were deemed acceptable for use in the present invention.

RESULTS-INSULIN-FC FUSION PROTEINS COMPRISING A CANINE Fc FRAGMENT

Example 20: Canine Insulin-Fc Fusion Protein Configurations Comprising the Canine Fc IgGA, IgGC and IgGD Isotypes An attempt was made to produce insulin-Fc fusion proteins comprising the insulin polypeptide sequences of SEQ ID NO: 4, SEQ ID NO: 5, SEQ ID NO: 7, and SEQ ID NO: 6, and the Fc fragment of the canine IgGA isotype (SEQ ID NO: 11), the canine IgGC isotype (SEQ ID NO: 13) or the canine IgGD isotype (SEQ ID NO: 14) using the peptide linker of SEQ ID NO: 10 or SEQ ID NO: 9. The full amino acid sequences for the resulting insulin-Fc fusion protein configurations are as follows:

```
                                                (SEQ ID NO: 22)
FVNQHLCGSDLVEALALVCGERGFFYTDPTGGGPRRGIVEQCCHSICSLY

QLENYCNGGGGAGGGGRCTDTPPCPVPEPLGGPSVLIFPPKPKDILRITR

TPEVTCVVLDLGREDPEVQISWFVDGKEVHTAKTQSREQQFNGTYRVVSV

LPIEHQDWLTGKEFKCRVNHIDLPSPIERTISKARGRAHKPSVYVLPPSP

KELSSSDTVSITCLIKDFYPPDIDVEWQSNGQQEPERKHRMTPPQLDEDG

SYFLYSKLSVDKSRWQQGDPFTCAVMHETLQNHYTDLSLSHSPG (SEQ ID NO: 23)
FVNQHLCGSDLVEALYLVCGERGFFYTDPTGGGPRRGIVEQCCHSICSLY

QLENYCNGGGGSGGGGRCTDTPPCPVPEPLGGPSVLIFPPKPKDILRITR

TPEVTCVVLDLGREDPEVQISWFVDGKEVHTAKTQSREQQFNGTYRVVSV

LPIEHQDWLTGKEFKCRVNHIDLPSPIERTISKARGRAHKPSVYVLPPSP

KELSSSDTVSITCLIKDFYPPDIDVEWQSNGQQEPERKHRMTPPQLDEDG

SYFLYSKLSVDKSRWQQGDPFTCAVMHETLQNHYTDLSLSHSPG (SEQ ID NO: 24)
FVNQHLCGSHLVEALYLVCGERGFFYTPKAGGGPRRGIVEQCCTSICSLY

QLENYCNGGGGSGGGGRCTDTPPCPVPEPLGGPSVLIFPPKPKDILRITR

TPEVTCVVLDLGREDPEVQISWFVDGKEVHTAKTQSREQQFNGTYRVVSV

LPIEHQDWLTGKEFKCRVNHIDLPSPIERTISKARGRAHKPSVYVLPPSP

KELSSSDTVSITCLIKDFYPPDIDVEWQSNGQQEPERKHRMTPPQLDEDG

SYFLYSKLSVDKSRWQQGDPFTCAVMHETLQNHYTDLSLSHSPG (SEQ ID NO: 25)
FVNQHLCGSHLVEALYLVCGERGFFYTPKAAAAAAAKGIVEQCCTSICSL

YQLENYCNGGGGSGGGGRCTDTPPCPVPEPLGGPSVLIFPPKPKDILRIT

RTPEVTCVVLDLGREDPEVQISWFVDGKEVHTAKTQSREQQFNGTYRVVS

VLPIEHQDWLTGKEFKCRVNHIDLPSPIERTISKARGRAHKPSVYVLPPS

PKELSSSDTVSITCLIKDFYPPDIDVEWQSNGQQEPERKHRMTPPQLDED

GSYFLYSKLSVDKSRWQQGDPFTCAVMHETLQNHYTDLSLSHSPG
```

FIG. 3 illustrates a side-by-side sequence comparison of SEQ ID NO: 22, SEQ ID NO: 23, SEQ ID NO: 24 and SEQ ID NO: 25. "*" represents complete homology across all sequences at a given sequence position, while ":", "." or spaces refer to conservative, moderate, or very different amino acid mutations across the sequences at a given sequence position, respectively.

The insulin-Fc fusion protein configuration of SEQ ID NO: 27, comprising the insulin polypeptide of SEQ ID NO: 5, the peptide linker of SEQ ID NO: 9 and the canine IgGC Fc fragment of SEQ ID NO: 13 yielded no material at all. The insulin-Fc fusion protein configuration of SEQ ID NO: 28, comprising the insulin polypeptide of SEQ ID NO: 5, the peptide linker of SEQ ID NO: 9 and the canine IgGD Fc fragment of SEQ ID NO: 14 yielded a good protein yield of 134 mg/L, however the material was highly aggregated with a % homodimer of 12.3% and a homodimer titer of 16.5 mg/L, which is significantly less than the required homodimer titer of 40 mg/L.

```
                                            (SEQ ID NO: 27)
FVNQHLCGSDLVEALALVCGERGFFYTDPTGGGPRRGIVEQCCHSICSLY

QLENYCNGGGGAGGGGCNNCPCPGCGLLGGPSVFIFPPKPKDILVTARTP

TVTCVVVDLDPENPEVQISWFVDSKQVQTANTQPREEQSNGTYRVVSVLP

IGHQDWLSGKQFKCKVNNKALPSPIEEIISKTPGQAHQPNVYVLPPSRDE

MSKNTVTLTCLVKDFFPPEIDVEWQSNGQQEPESKYRMTPPQLDEDGSYF

LYSKLSVDKSRWQRGDTFICAVMHEALHNHYTQISLSHSPG (SEQ ID NO: 28)
FVNQHLCGSDLVEALALVCGERGFFYTDPTGGGPRRGIVEQCCHSICSLY

QLENYCNGGGGAGGGGCISPCPVPESLGGPSVFIFPPKPKDILRITRTPE

ITCVVLDLGREDPEVQISWFVDGKEVHTAKTQPREQQFNSTYRVVSVLPI

EHQDWLTGKEFKCRVNHIGLPSPIERTISKARGQAHQPSVYVLPPSPKEL

SSSDTVTLTCLIKDFFPPEIDVEWQSNGQPEPESKYHTTAPQLDEDGSYF

LYSKLSVDKSRWQQGDTFTCAVMHEALQNHYTDLSLSHSPG
```

The insulin-Fc fusion protein configurations of SEQ ID NO: 22, SEQ ID NO: 23, SEQ ID NO: 24, SEQ ID NO: 25, SEQ ID NO: 27 and SEQ ID NO: 28 were synthesized in HEK cells according to Example 1 and purified according to Example 3. The structure of the insulin-Fc fusion protein was confirmed according to Example 5 by non-reducing and reducing CE-SDS, and the sequence was further identified by LC-MS with glycan removal according to Example 7. The % homodimer was measured by size-exclusion chromatography according to Example 9. The results are given in Table 1. In summary, despite mutating the insulin polypeptide and/or the linker, there was no embodiment based on the canine IgGA Fc fragment (SEQ ID NO: 11) with a low enough degree of aggregation and a high enough titer of the desired homodimer.

TABLE 1

Homodimer Titers for Insulin-Fc Fusion Protein Configurations Utilizing Canine IgG Fc Fragments

| SEQ ID NO: | Canine IgG | Protein Yield (mg/L) | % Homodimer | Homodimer Titer (mg/L) |
|---|---|---|---|---|
| SEQ ID NO: 22 | IgGA | 22 | 24% | 5.28 |
| SEQ ID NO: 23 | IgGA | 21 | 19% | 3.99 |
| SEQ ID NO: 24 | IgGA | 11 | Not tested | ≤11 |
| SEQ ID NO: 25 | IgGA | 18 | Not tested | ≤18 |
| SEQ ID NO: 27 | IgGC | 0 | Not tested | 0 |
| SEQ ID NO: 28 | IgGD | 134 | 12% | 16.5 |

Example 21: Canine Insulin-Fc Fusion Protein Configurations Comprising the Canine Fc IgGB Isotype On the other hand, replacing the canine IgGA Fc fragment (SEQ ID NO: 11) with the canine IgGB Fc fragment (SEQ ID NO: 12) yielded a much less aggregated compound with a comparatively high titer of the desired homodimer. The insulin-Fc fusion protein configuration of SEQ ID NO: 26, comprising the insulin polypeptide of SEQ ID NO: 5, the linker of SEQ ID NO: 9 and the canine IgGB Fc fragment of SEQ ID NO: 12 had a protein yield of 80 mg/L and a % homodimer of 93% resulting in a homodimer titer of 74.7 mg/L, which surpassed the required homodimer titer of 40 mg/L.

```
                                            (SEQ ID NO: 26)
FVNQHLCGSDLVEALALVCGERGFFYTDPTGGGPRRGIVEQCCHSICSLY

QLENYCNGGGGAGGGGDCPKCPAPEMLGGPSVFIFPPKPKDTLLIARTPE

VTCVVVDLDPEDPEVQISWFVDGKQMQTAKTQPREEQFNGTYRVVSVLPI

GHQDWLKGKQFTCKVNNKALPSPIERTISKARGQAHQPSVYVLPPSREEL

SKNTVSLTCLIKDFFPPDIDVEWQSNGQQEPESKYRTTPPQLDEDGSYFL

YSKLSVDKSRWQRGDTFICAVMHEALHNHYTQESLSHSPG
```

Example 22: In Vitro IM-9 Insulin Receptor Binding of an Exemplary Insulin-Fc Fusion Protein at 4° C.

In vitro insulin receptor binding for the insulin-Fc fusion protein configurations of SEQ ID NO: 22 (IgGA), SEQ ID NO: 26 (IgGB), SEQ ID NO: 27 (IgGC) and SEQ ID NO: 28 (IgGD) were tested according to the procedure of Example 11. As shown in Table 2, the insulin-Fc fusion protein of SEQ ID NO: 22 demonstrated in IR binding IC50 of 2733 and the insulin-Fc fusion protein of SEQ ID NO: 28 demonstrated an IR binding IC50 of greater than 5000 nM, indicating that neither insulin-Fc fusion protein configuration was highly unlikely to show bioactivity in vivo. The insulin-Fc fusion protein of SEQ ID NO: 27 had no yield and so the IR binding IC50 was not measure. However, the insulin-Fc fusion protein of SEQ ID NO: 26 demonstrated an IC50 of 28 nM indicating that this sequence was likely to be bioactive in vivo.

TABLE 2

Homodimer Titers for Sequences Utilizing Native Canine IgGA, IgGB, IgGC, and IgGD Fc Fragments

| SEQ ID NO: | IgG Fragment | Protein Yield (mg/L) | % Homo-dimer | Homo-dimer Titer (mg/L) | IR Binding, IC50 (nM) |
|---|---|---|---|---|---|
| SEQ ID NO: 22 | IgGA | 22 | 24% | 5.28 | 2,733 |
| SEQ ID NO: 26 | IgGB | 80 | 93% | 74.4 | 28 |
| SEQ ID NO: 27 | IgGC | 0 | Not tested | 0 | DNM* |
| SEQ ID NO: 28 | IgGD | 134 | 12% | 16.5 | >5000 |

*DNM = Did Not Measure

Figure 5:
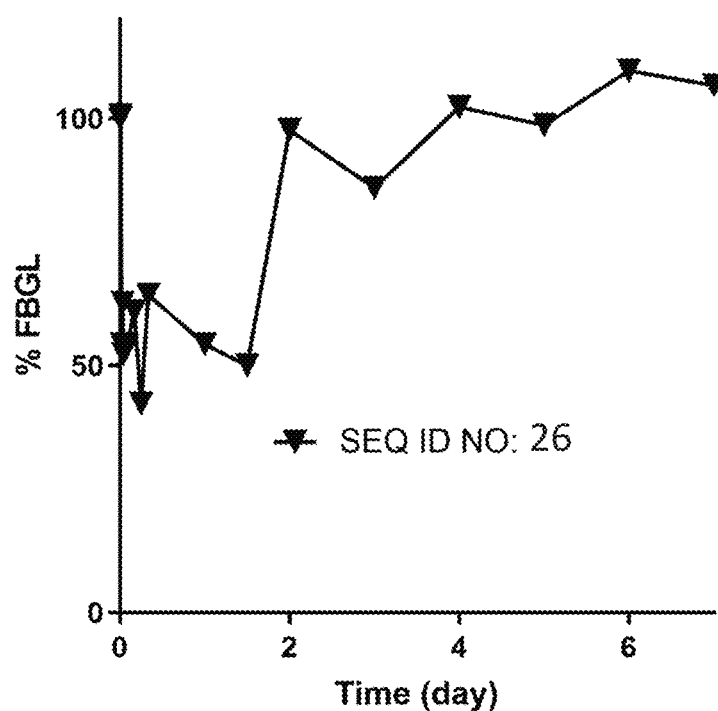
FIG. 5 shows average % fasting blood glucose levels from Day 0 to Day 7 for N=3 dogs dosed intravenously on Day 0 at 0.2 mg/kg with the homodimer of SEQ ID NO: 26.
Figure 6:
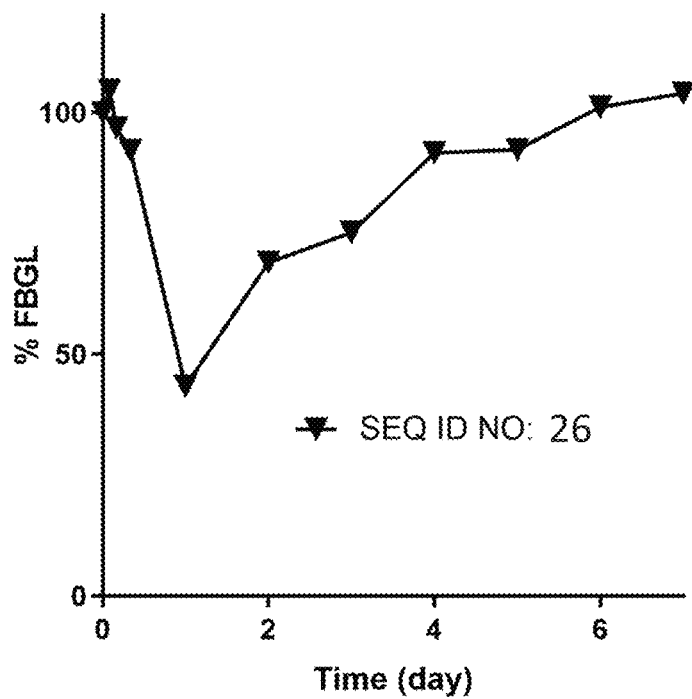
FIG. 6 shows average % fasting blood glucose levels from Day 0 to Day 7 for N=6 dogs dosed subcutaneously on Day 0 at 0.33 mg/kg with the homodimer of SEQ ID NO: 26.

Example 23: In Vivo Efficacy of an Insulin-Fc Fusion Protein Comprising the Insulin Polypeptide of SEQ ID NO: 5 with a Canine IgGB Isotype Fc Fragment Given the promising homodimer titer and insulin receptor activity results in Examples 21 and 22, the insulin-Fc fusion protein of SEQ ID NO: 26 was tested for in vivo bioactivity according to Example 13 following an intravenous injection in each of N=3 healthy, antibody-naïve, beagle dogs weighing approximately 10 kg. In a separate experiment, the compound was administered subcutaneously to N=3 naïve beagle dogs. FIG. 5 shows the % FBGL versus time for a single intravenous administration of the insulin-Fc fusion protein of SEQ ID NO: 26, and FIG. 6 shows the % FBGL vs. time for a single subcutaneous administration of the insulin-Fc fusion protein of SEQ ID NO: 26, both of which demonstrate that the insulin-Fc fusion protein of SEQ ID NO: 26 is significantly bioactive in dogs.

Figure 2:
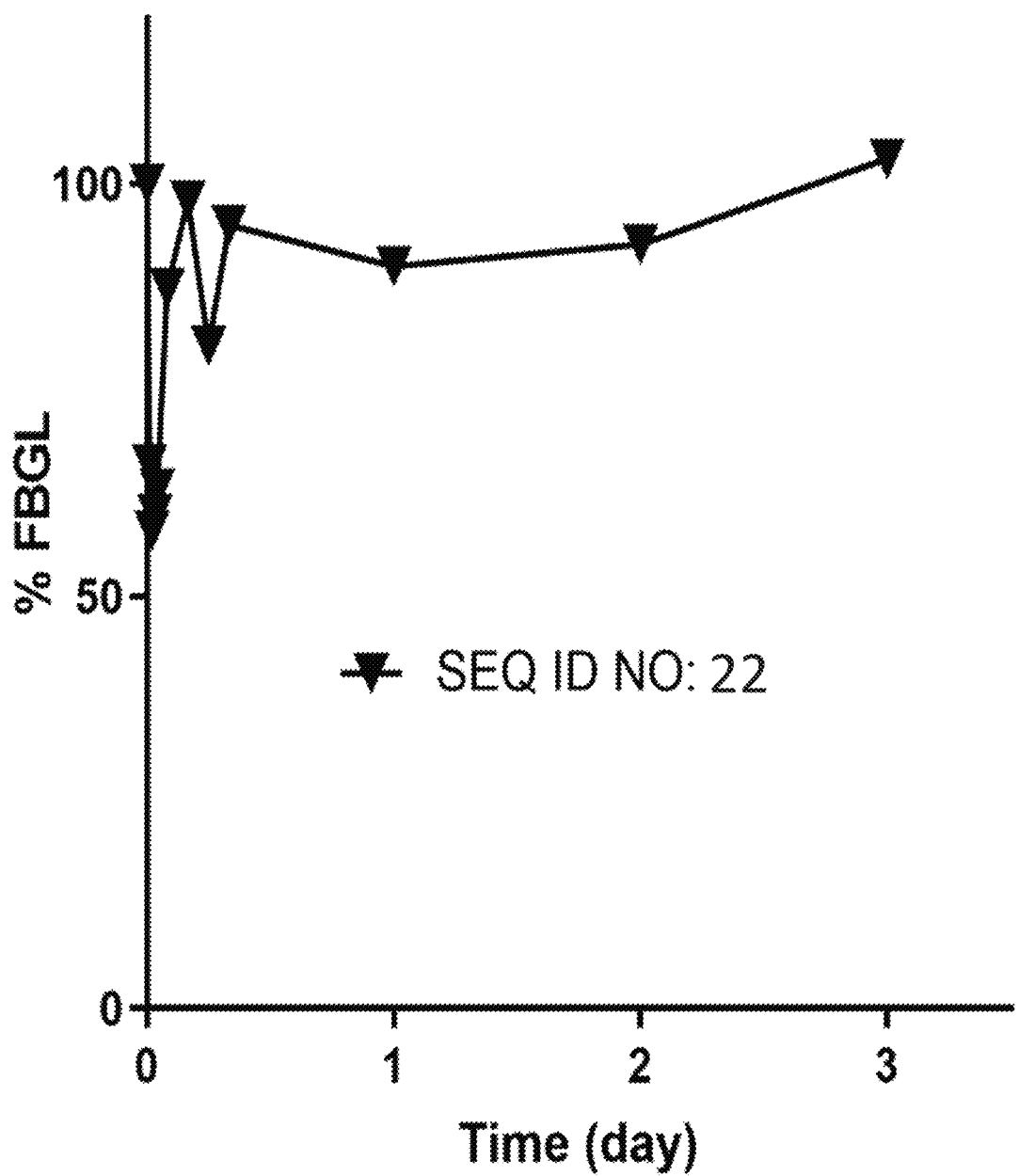
FIG. 2 shows average % fasting blood glucose levels from Day 0 to Day 3 for N=3 dogs dosed intravenously on Day 0 at 0.2 mg/kg with the homodimer of SEQ ID NO: 22.
Figure 8:
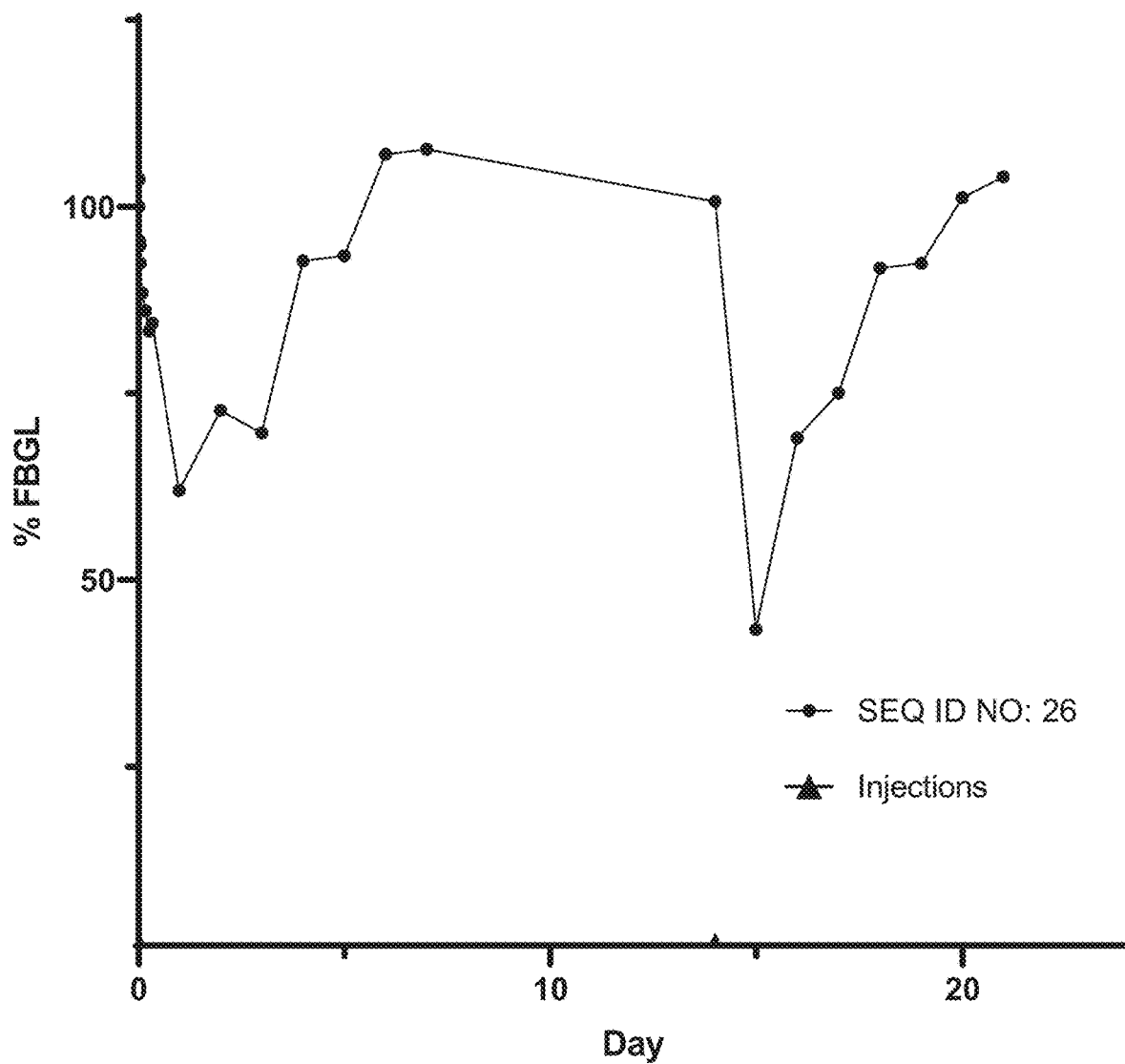
FIG. 8 shows % fasting blood glucose levels from Day 0 to Day 21 for N=1 dog dosed subcutaneously on Day 0 and Day 14 with the homodimer of SEQ ID NO: 26.
Figure 9:
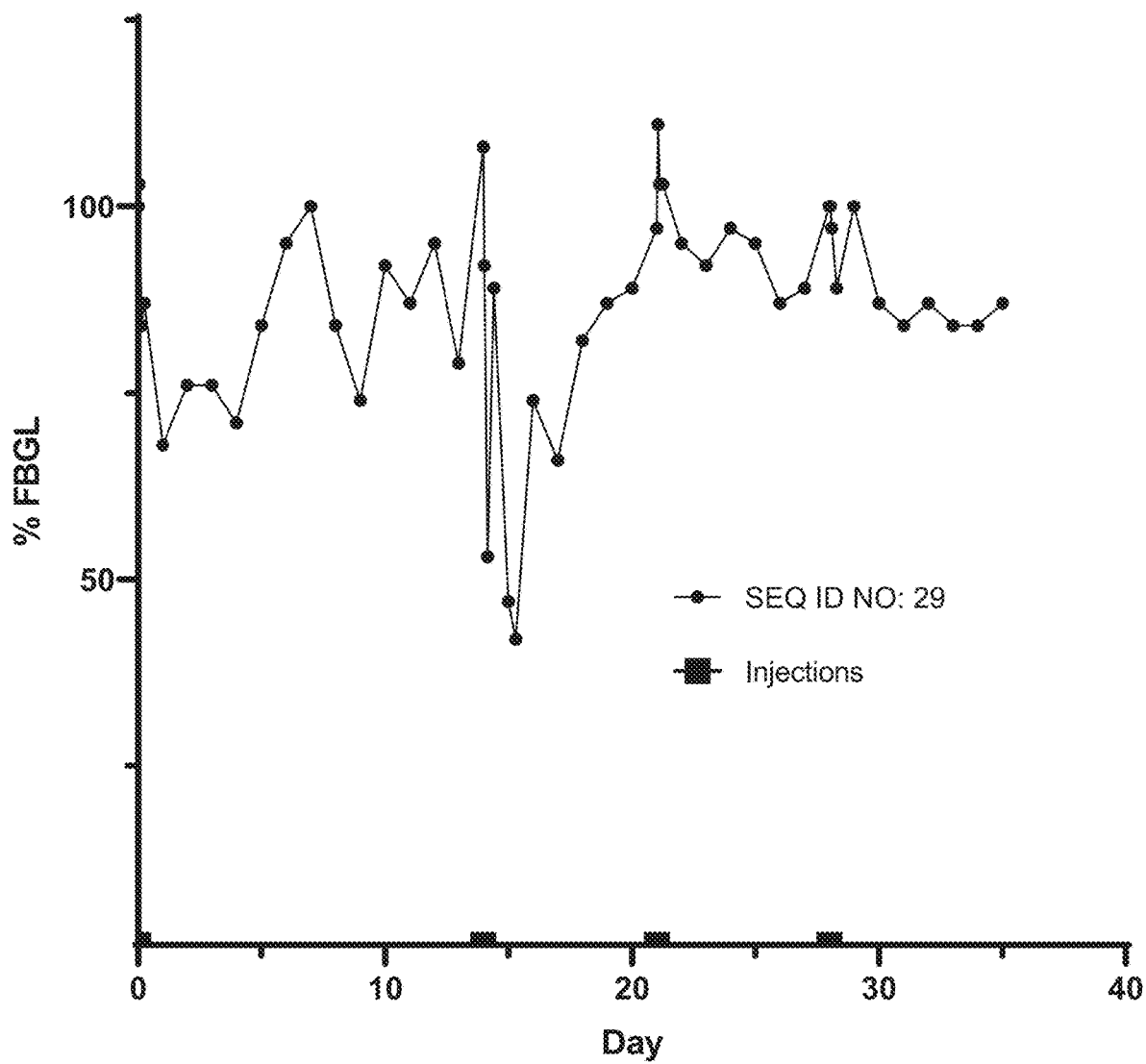
FIG. 9 shows % fasting blood glucose levels from Day 0 to Day 35 for N=1 dog dosed subcutaneously on Day 0, Day 14, Day 21 and Day 28 with the homodimer of SEQ ID NO: 29.

The NAOC was calculated according to the procedure of Example 15 to determine the relative bioactivity and duration of action of the insulin-Fc fusion protein. The NAOC of the insulin-Fc fusion protein of SEQ ID NO: 26 injected intravenously was 399% FBGL·days·kg/mg which was 3.8 times the NAOC of the insulin-Fc fusion protein of SEQ ID NO: 22 injected intravenously, illustrating significantly increased bioactivity for the insulin-Fc fusion protein comprising the canine IgGB Fc fragment versus the insulin-Fc fusion protein comprising the canine IgGA Fc fragment. The in vivo bioactivity of SEQ ID NO: 22 is illustrated in FIG. 2. The NAOC of the insulin-Fc fusion protein of SEQ ID NO: 26 injected subcutaneously was 366% FBGL days kg/mg, demonstrating a level of bioactivity via subcutaneous administration that is like that obtained via intravenous administration. The in vivo bioactivity of SEQ ID NO: 26 across two doses is illustrated in FIG. 8.

Example 24: In Vivo Immunogenicity Screening After Repeated Subcutaneous Doses of the Insulin-Fc Fusion Protein Comprising the Insulin Polypeptide of SEQ ID NO: 26 With a Canine IgGB Isotype Fc Fragment Next, the repeated dose subcutaneous bioactivity of the insulin-Fc fusion protein of SEQ ID NO: 26 was tested in dogs as per the method described in Example 15. N=3 animals were dosed subcutaneously at Day 0, at Day 35, and at Day 42, and the % FBGL was measured for the 7-day window after each dose according to Example 15. The NAOC and NAOCR were calculated according to the procedure of Example 15 for each repeated subcutaneous injection. As illustrated in Table 3, repeated subcutaneous dosing in dogs unexpectedly revealed a significant decay in bioactivity by the third dose as measured by a significant decrease in the NAOCR (i.e., the NAOC for the third injection was only 0.40, or 40%, of the NAOC for the first injection).

TABLE 3

NAOC per Dose and NAOCR for Repeated Doses of SEQ ID NO: 26

| Injection Number of SEQ ID NO: 26 | NAOC (% FBGL · days · kg/mg) | NAOCR (ratioed to Week 1) |
|---|---|---|
| 1 | 330 | 1.0 |
| 2 | 339 | 1.1 |
| 3 | 115 | 0.4 |

Figure 7:
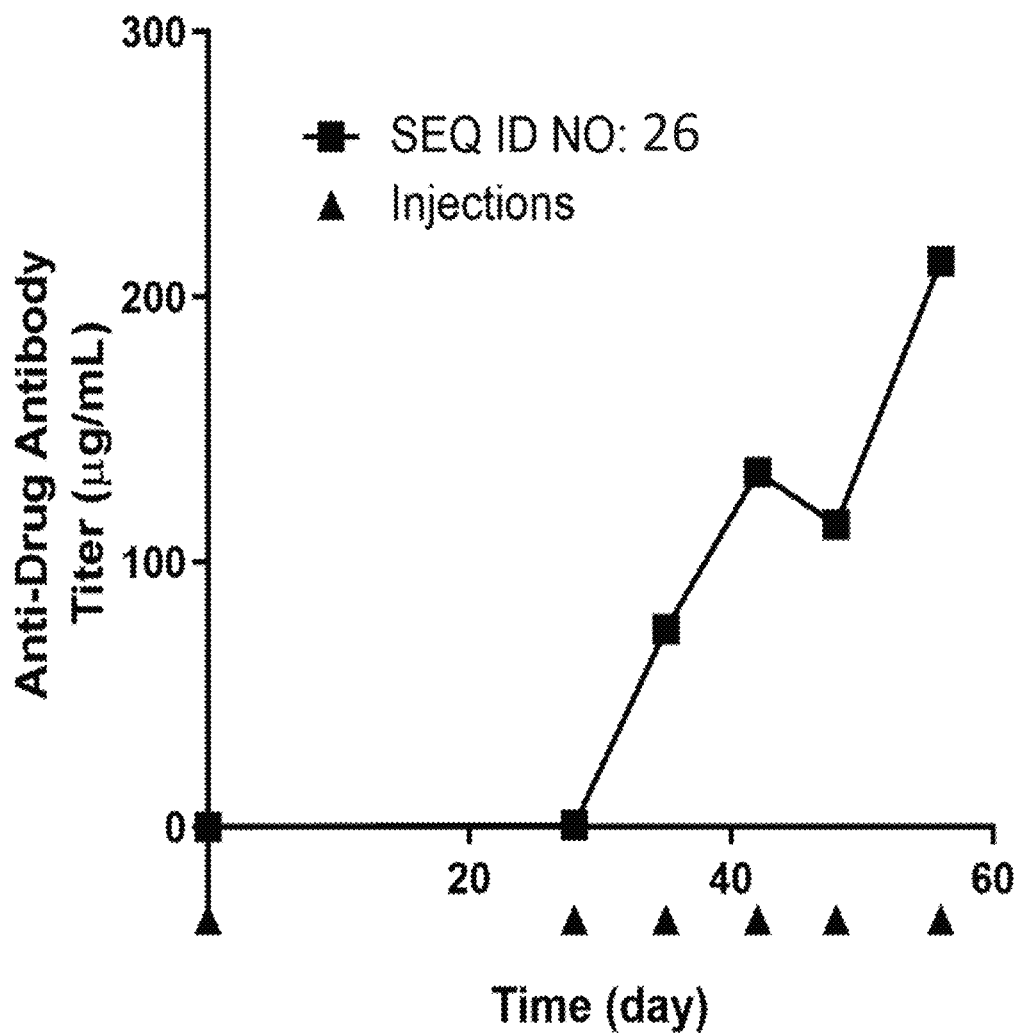
FIG. 7 shows the average anti-drug antibody titer (µg/mL) for N=3 dogs dosed subcutaneously on Day 0 (0.30 mg/kg), Day 28 (0.33 mg/kg), Day 35 (0.33 mg/kg), Day 42 (0.50 mg/kg), Day 49 (1.00 mg/kg) and Day 56 (1.00 mg/kg) with the homodimer of SEQ ID NO: 26.

Without being bound to any particular explanation, it was postulated that the cause of the significant reduction in bioactivity of the insulin-Fc fusion protein of SEQ ID NO: 26 after the third repeated subcutaneous dose in dogs was due to the development of anti-drug antibodies that neutralized its biological activity. Anti-drug antibodies may be directed against the insulin polypeptide, linker, or Fc-fragment portions of an insulin-Fc fusion protein. The immunogenic response manifests as interactions between antigen presenting cells, T-helper cells, B-cells, and their associated cytokines, which may lead to the production of endogenous antibodies against the drug (e.g., anti-drug antibodies). Binding antibodies are all isotypes capable of binding the insulin-Fc fusion protein, and these may be detected in an immunoassay as described in Example 17. Neutralizing antibodies that inhibit functional activity of the insulin-Fc fusion protein are generally directed against an epitope that is required for bioactivity. To assess whether this was the case, serum that was collected prior to the administration of each dose and at the end of the experiment described in Examples 11 was tested to quantify the levels of anti-drug antibodies according to Example 17. As shown in FIG. 7, levels of anti-drug antibodies did indeed increase with multiple subcutaneous administrations of the compound, indicating that the generation of neutralizing anti-drug antibodies were the likely cause for the reduction in the NAOCR after the third injection of the insulin Fc-fusion protein of SEQ ID NO: 26.

Example 25: Non-Glycosylated Insulin-Fc Fusion Protein Comprising the Insulin Polypeptide of SEQ ID NO: 5 With Canine IgGB Isotype Fc Fragments to Reduce the Potential Risk of Immunogenicity As shown in Example 21, Example 22 and Example 23, the insulin-Fc fusion protein of SEQ ID NO: 26 showed acceptable % homodimer content, homodimer titer, and bioactivity in dogs; however, its use for a chronic disease such as diabetes is compromised by the reduction in bioactivity and generation of anti-drug antibodies (Example 24) with repeated subcutaneous dosing. Without being bound to any particular theory, one possible cause of the generation of anti-drug antibodies and the reduction in bioactivity is the increased interaction of the canine IgGB Fc fragment with various receptors of the canine immune system (e.g., Fc(gamma) receptors, e.g., Fc(gamma)RI). Nevertheless, the canine IgGB isotype was the only one of the four canine IgG isotypes that, when used for the Fc fragment, resulted in an insulin-Fc fusion protein meeting the manufacturability and single-dose bioactivity design goals (Example 19). As described in the Detailed Description of the Invention, one method for reducing the Fc(gamma) interaction involves mutating the Fc fragment cNg site to prevent glycosylation during synthesis in the host cell.

Therefore, cNg site mutations were made to the Fc fragment region of SEQ ID NO: 26 to reduce the binding affinity of the Fc fragment for Fc(gamma) receptors in vivo, as measured by binding in an in vitro human Fc(gamma)RI assay described in Example 12. Verification of the lack of glycan were performed using the LC-MS method of Example 7, but with omission of the PNGase F treatment step. The position of the cNg site in the insulin-Fc fusion protein of SEQ ID NO: 26 is cNg-NB139. Mutations to SEQ ID NO: 26 included SEQ ID NO: 29 comprising a mutation of cNg-NB139-S, SEQ ID NO: 30 comprising a mutation of cNg-NB139-Q together with reverting to the native B10H and ABT, and SEQ ID NO: 31 comprising removal of the aspartic acid at the N-terminus of the Fc fragment (des hinge D) a mutation of cNg-NB138-K (due to the des hinge D mutation, the cNg site for SEQ ID NO: 31 is NB138 instead of NB139). The full amino acid sequences of the cNg-mutated insulin-Fc fusion proteins are listed below (with the cNg position in bold).

(SEQ ID NO: 29)

FVNQHLCGSDLVEALALVCGERGFFYTDPTGGGPRRGIVEQCCHSICSLY

QLENYCNGGGGAGGGGDCPKCPAPEMLGGPSVFIFPPKPKDTLLIARTPE

VTCVVVDLDPEDPEVQISWFVDGKQMQTAKTQPREEQFSGTYRVVSVLPI

GHQDWLKGKQFTCKVNNKALPSPIERTISKARGQAHQPSVYVLPPSREEL

SKNTVSLTCLIKDFFPPDIDVEWQSNGQQEPESKYRTTPPQLDEDGSYFL

YSKLSVDKSRWQRGDTFICAVMHEALHNHYTQESLSHSPG (SEQ ID NO: 30)

FVNQHLCGSHLVEALALVCGERGFFYTDPTGGGPRRGIVEQCCTSICSLY

QLENYCNGGGGAGGGGDCPKCPAPEMLGGPSVFIFPPKPKDTLLIARTPE

VTCVVVDLDPEDPEVQISWFVDGKQMQTAKTQPREEQFQGTYRVVSVLPI

GHQDWLKGKQFTCKVNNKALPSPIERTISKARGQAHQPSVYVLPPSREEL

SKNTVSLTCLIKDFFPPDIDVEWQSNGQQEPESKYRTTPPQLDEDGSYFL

YSKLSVDKSRWQRGDTFICAVMHEALHNHYTQESLSHSPG (SEQ ID NO: 31)

FVNQHLCGSDLVEALALVCGERGFFYTDPTGGGPRRGIVEQCCHSICSLY

QLENYCNGGGGAGGGGCPKCPAPEMLGGPSVFIFPPKPKDTLLIARTPEV

TCVVVDLDPEDPEVQISWFVDGKQMQTAKTQPREEQFKGTYRVVSVLPIG

HQDWLKGKQFTCKVNNKALPSPIERTISKARGQAHQPSVYVLPPSREELS

KNTVSLTCLIKDFFPPDIDVEWQSNGQQEPESKYRTTPPQLDEDGSYFLY

SKLSVDKSRWQRGDTFICAVMHEALHNHYTQESLSHSPG

The insulin-Fc fusion proteins were manufactured in HEK293 cells according to Example 1 and purified using a Protein A column according to Example 3. The structures of the insulin-Fc fusion proteins were confirmed according to Example 5 by non-reducing and reducing CE-SDS, and the sequences were further identified by LC-MS with glycan removal according to Example 7. The % homodimer was measured by size-exclusion chromatography according to Example 9. As shown in Table 4, the homodimer titers of the insulin-Fc fusion proteins of SEQ ID NO: 29, SEQ ID NO: 30 and SEQ ID NO: 31 met the design goal for homodimer titer.

Example 26: Screening of Canine Serum Containing Anti Drug Antibodies and Identification of Potential Immunogenic Epitopes at the B10D and ABH Positions of the Insulin Polypeptide It was hypothesized, therefore, that the insulin polypeptide of SEQ ID NO: 5 may unexpectedly contain specific epitopes (i.e., immunogenic "hot spots") against which the dog's immune system is directed. Therefore, the binding specificity of the antibodies present in the serum samples described in Example 17 were evaluated according to the general procedure of Example 18. The analysis of the antibody-containing serum samples from the repeated dosing of the insulin-Fc fusion protein of SEQ ID NO: 26 (Example 24) against the coated insulin-Fc fusion protein library demonstrated that there were unexpectedly two primary "hot spots" present within the insulin polypeptide sequence of SEQ ID NO: 5: the aspartic acid mutation at the 10th position from the N-terminus of the B-chain (i.e., B10), and, separately, the histidine mutation at the 8th position from the N-terminal end of the A-chain (i.e., A8). The results suggest that insulin-Fc fusion proteins comprising insulin polypeptide amino acid compositions containing these two particular amino acid mutations are likely to be immunogenic in dogs and therefore likely to give rise to anti-drug antibodies that neutralize the bioactivity after repeated injections. The insulin-Fc fusion protein configurations of SEQ ID NO: 29 and SEQ ID NO: 31 however met the design requirements for IR binding IC50, while the insulin-Fc fusion protein configuration of SEQ ID NO: 30 (where the B10D and A8H mutations were restored to the native B10H and A8T) demonstrated an IR binding IC50 or >5000 nM, indicating that this insulin-Fc fusion protein configuration was highly unlikely to be bioactive in vivo. This indicated that the B10H and A8T mutations in these insulin-Fc fusion protein configurations appeared to be necessary to achieve in vivo bioactivity.

TABLE 4

Homodimer Titers and IR Binding for Insulin-Fc Fusion Protein Configurations Utilizing Canine IgGB Fc with cNg Mutations

| SEQ ID NO: | cNg MUTATION | Protein Yield (mg/L) | % Homodimer | Homodimer Titer (mg/L) | IR Binding, IC50 (nM) |
|---|---|---|---|---|---|
| SEQ ID NO: 29 | S | 76.7 | 98.3% | 75.4 | 145 |
| SEQ ID NO: 30 | Q | 21.4 | 98.7% | 21.1 | >5000 |
| SEQ ID NO: 31 | K | 45.4 | 98.1% | 44.5 | 147 |

Example 27: Evaluation of In Vivo Bioactivity and Immunogenicity of Non-Glycosylated Insulin-Fc Fusion Protein Configurations of with cNg Mutations of the Canine IgGB Isotype Fc Fragment To determine if the insulin-Fc fusion protein of SEQ ID NO: 29, containing the cNg-S mutation, improved the repeated dose bioactivity performance in dogs, the compound was administered subcutaneously to N=1 dog on Day 0, Day 14, Day 21 and on Day 28 according to the procedure of Example 15. The % FBGL across these doses for SEQ ID NO: 29 is illustrated in FIG. 9. When the dog's % FBGL dropped too low, the dog was given food to raise the blood glucose to a safe level. The NAOC for the first injection measured over the first 7 days following the injection was 403% FBGL·days·kg/mg, showing that the insulin-Fc fusion protein of SEQ ID NO: 29 was satisfactorily bioactive in vivo. The NAOC and NAOCR were also measured for each subsequent dose according to the general procedure of Example 15, calculated from the time the dose was administered until just before the next dose was administered. The NAOC and the NAOCR shown in Table 5 illustrate that the insulin-Fc fusion protein of SEQ ID NO: 29 exhibited an NAOCR that decreased significantly on doses 2 and 3 of a three dose regimen. Therefore, the insulin-Fc fusion protein of SEQ ID NO: 29, containing the cNg-S mutation, was unable to demonstrate repeated dose bioactivity in dogs.

TABLE 5

NAOC per Dose for Repeated Doses of SEQ ID NO: 29

| Injection Number of SEQ ID NO: 29 | NAOC (% FBGL · days · kg/mg) | NAOCR |
|---|---|---|
| 1 | 403 | 1.0 |
| 2 | 508 | 0.3 |
| 3 | 128 | 0.32 |

Figure 10:
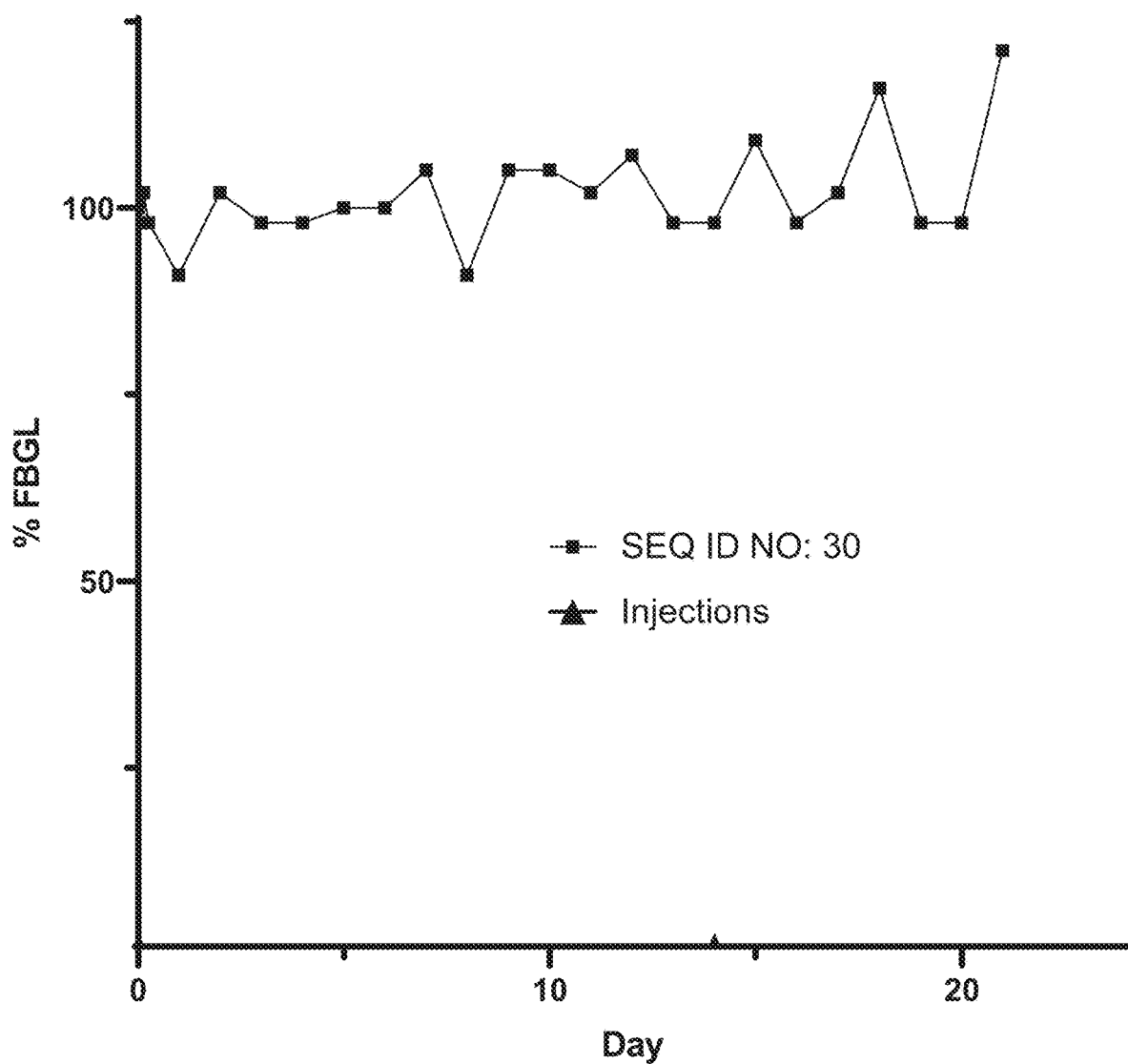
FIG. 10 shows % fasting blood glucose levels from Day 0 to Day 21 for N=1 dog dosed subcutaneously on Day 0 and Day 14 with the homodimer of SEQ ID NO: 30.

To determine if the insulin-Fc fusion protein of SEQ ID NO: 30, containing the cNg-Q mutation, improved the repeated dose bioactivity performance in dogs, the compound was administered subcutaneously to N=1 dog on Day 0 and on Day 28 according to the procedure of Example 15. The % FBGL across these doses for SEQ ID NO: 30 is illustrated in FIG. 10. When the dog's % FBGL dropped too low, the dog was given food to raise the blood glucose to a safe level. The NAOC for the first injection measured over the first 7 days following the injection was 24.2% FBGL days kg/mg, showing that the insulin-Fc fusion protein of SEQ ID NO: 30 did not show satisfactory bioactive in vivo. The NAOC and NAOCR were also measured for the subsequent dose according to the general procedure of Example 15, calculated from the time the dose was administered until just before the next dose was administered. The NAOC and the NAOCR shown in Table 6 illustrate that the insulin-Fc fusion protein of SEQ ID NO: 30 exhibited 0 NAOC and NAOCR for the second dose. Therefore, the insulin-Fc fusion protein of SEQ ID NO: 30, containing the cNg-Q mutation, was unable to demonstrate repeated dose bioactivity in dogs.

TABLE 6

NAOC per Dose for Repeated Doses of SEQ ID NO: 30

| Injection Number of SEQ ID NO: 30 | NAOC (% FBGL · days · kg/mg) | NAOCR |
|---|---|---|
| 1 | 403 | 1.0 |
| 2 | 0 | 0.0 |

Figure 11:
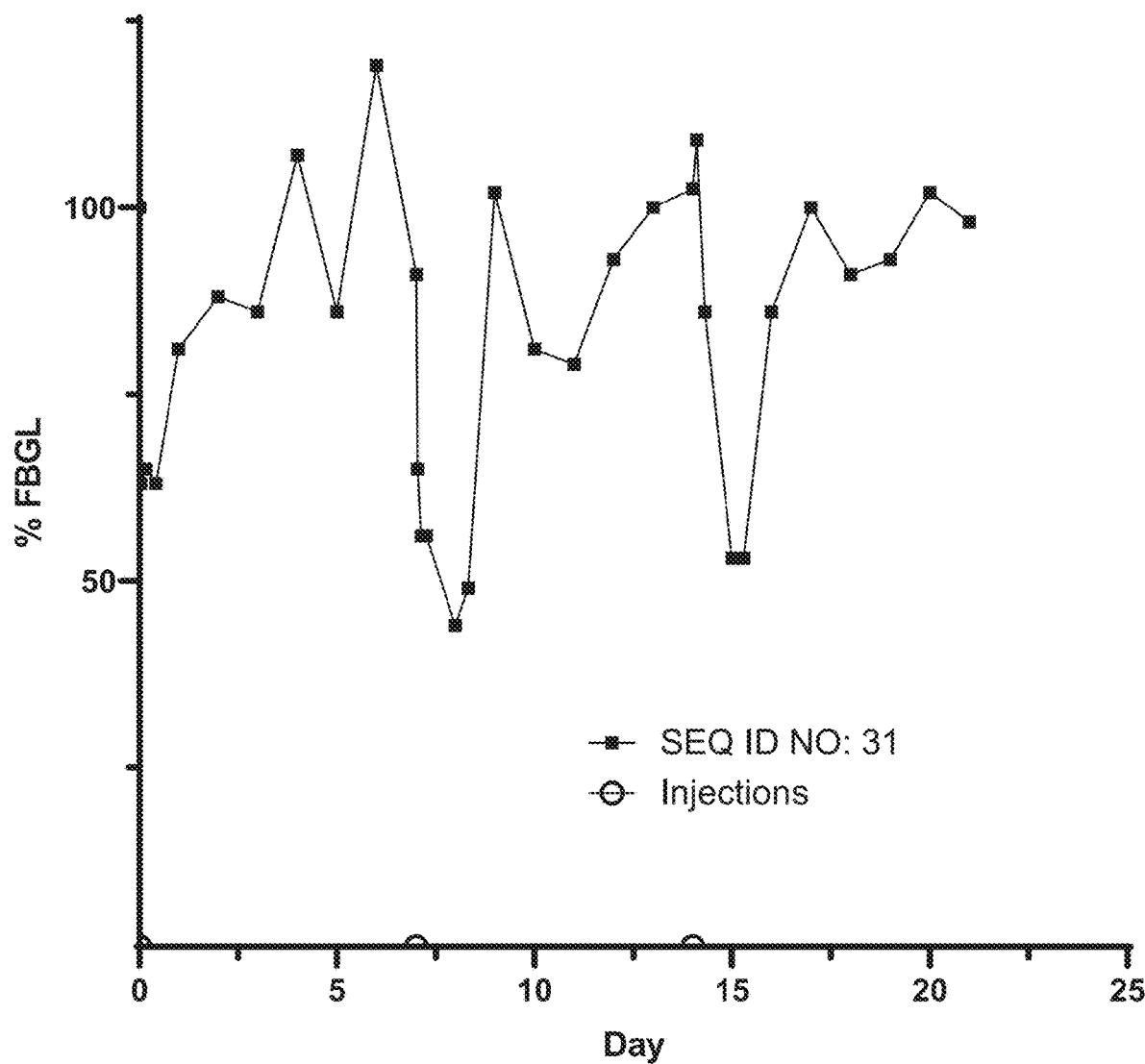
FIG. 11 shows % fasting blood glucose levels from Day 0 to Day 21 for N=1 dog dosed subcutaneously on Day 0, Day 7 and Day 14 with the homodimer of SEQ ID NO: 31.

To determine if the insulin-Fc fusion protein of SEQ ID NO: 31, containing the cNg-K mutation together with the des hinge D omission (the Fc fragment of SEQ ID NO: 16) improved the repeated dose bioactivity performance in dogs, the compound was administered subcutaneously to N=1 dog on Day 0, Day 7, and Day 14 according to the procedure of Example 15. The % FBGL across these doses for SEQ ID NO: 31 is illustrated in FIG. 11. When the dog's % FBGL dropped too low, the dog was given food to raise the blood glucose to a safe level. The NAOC for the first injection was 178% FBGL·days·kg/mg, showing that the insulin-Fc fusion protein of SEQ ID NO: 31 was satisfactorily bioactive in vivo. The NAOC and NAOCR were also measured for each subsequent dose according to the general procedure of Example 15, calculated from the time the dose was administered until just before the next dose was administered. The NAOC and the NAOCR shown in Table 7 illustrate that the insulin-Fc fusion protein configuration of SEQ ID NO: 31 maintains an NAOCR greater than 0.6 throughout the three doses. Therefore, unexpectedly, the insulin-Fc fusion protein of SEQ ID NO: 31, containing the cNg-K mutation with des hinge D, was the only non-glycosylated mutant of the insulin-Fc fusion protein of SEQ ID NO: 26 resulting in significantly improved repeated dose bioactivity in dogs.

TABLE 7

NAOC per Dose for Repeated Doses of SEQ ID NO: 31

| Injection Number of SEQ ID NO: 31 | NAOC (% FBGL · days · kg/mg) | NAOCR |
|---|---|---|
| 1 | 178 | 1.0 |
| 2 | 382 | 2.2 |
| 3 | 238 | 1.3 |

Example 28: In Vivo Pharmacodynamics (PD) After a Single Administration of an Insulin Fc-Fusion Protein in Felines A bioactive insulin-Fc fusion homodimer construct of SEQ ID NO: 32 was synthesized according to Example 1 and was assessed for its effects on fasting blood glucose levels as follows. N=3 healthy, antibody-naïve, cats weighing approximately 5 kg were used. On Day 0, the cats received a single injection of a pharmaceutical composition containing an insulin Fc-fusion protein homodimer of SEQ ID NO: 32 in a solution of 50 mM sodium hydrogen phosphate, 150 mM sodium chloride, and 0.02% v/v Tween-80 at pH 7.5, at a dose of 6 nmol/kg (equivalent to 0.39 mg Fc fusion protein/kg or 1.9 U/kg insulin equivalent on molar basis). On Day 0 immediately prior to injection and at 15, 30, 45, 60, 120, 240, 360, and 480 minutes and at 1, 2, 3, 4, 5, 6, 7, and 8 days post injection blood was collected from a suitable vein.

For each time point, a minimum of 1 mL of whole blood was collected. A glucose level reading was immediately determined using a glucose meter (ACCU-CHEK® Aviva Plus), which requires approximately one drop of blood. Average % fasting blood glucose levels (% FBGL) from Day 0 to Day 8 were plotted in FIG. 12, which allows the bioactivity of a fusion protein to be determined. FIG. 12 demonstrates that the homodimer of the SEQ ID NO: 32 can lower blood glucose for a significant period of time on a single dose.

Example 29: In Vivo Pharmacodynamics (PD) After a Single Administration of an Insulin Fc-Fusion Protein in Felines A bioactive insulin-Fc fusion homodimer construct of SEQ ID NO: 32 was synthesized according to Example 1 and was assessed for its effects on fasting blood glucose levels as follows. N=3 healthy, antibody-naïve, cats weighing approximately 5 kg were used. On Day 0, the cats received a single injection of a pharmaceutical composition containing an insulin Fc-fusion protein homodimer of SEQ ID NO: 32 in a solution of 50 mM sodium hydrogen phosphate, 150 mM sodium chloride, and 0.02% v/v Tween-80 at pH 7.5, at a dose of 6 nmol/kg (equivalent to 0.39 mg Fc fusion protein/kg or 1.9 U/kg insulin equivalent on molar basis). On Day 0 immediately prior to injection and at 15, 30, 45, 60, 120, 240, 360, and 480 minutes and at 1, 2, 3, 4, 5, 6, 7, and 8 days post injection blood was collected from a suitable vein.

For each time point, a minimum of 1 mL of whole blood was collected. A glucose level reading was immediately determined using a glucose meter (ACCU-CHEK® Aviva Plus), which requires approximately one drop of blood. Average % fasting blood glucose levels (% FBGL) from Day 0 to Day 8 were plotted in FIG. 12, which allows the bioactivity of a fusion protein to be determined. FIG. 12 demonstrates that the homodimer of the SEQ ID NO: 32 can lower blood glucose for a significant period of time on a single dose.

Example 29: In Vivo Pharmacodynamics (PD) After a Single Administration of an Insulin Fc-Fusion Protein in Felines A bioactive insulin-Fc fusion homodimer construct is synthesized according to Example 1 and is assessed for its effects on fasting blood glucose levels as follows. Healthy, antibody-naïve, cats weighing approximately 5 kg are used. On Day 0, the cats receive a single injection of a pharmaceutical composition containing an insulin Fc-fusion protein homodimer in a solution of 50 mM sodium hydrogen phosphate, 150 mM sodium chloride, and 0.02% v/v Tween-80 at pH 7.5, at a dose of 6 nmol/kg (equivalent to 0.39 mg Fc fusion protein/kg or 1.9 U/kg insulin equivalent on molar basis). On Day 0 immediately prior to injection and at 15, 30, 45, 60, 120, 240, 360, and 480 minutes and at 1, 2, 3, 4, 5, 6, 7, and 8 days post injection blood was collected from a suitable vein.

For each time point, a minimum of 1 mL of whole blood is collected. A glucose level reading is immediately determined using a glucose meter (ACCU-CHEK® Aviva Plus), which requires approximately one drop of blood. Average % fasting blood glucose levels (% FBGL) from Day 0 to Day 8 are plotted, which allows the bioactivity of a fusion protein to be determined. It is expected that the homodimers of SEQ ID NO: 34 and SEQ ID NO: 36 will lower blood glucose for a significant period of time on a single dose.

Example 30: In Vivo Immunogenicity Screening After Repeated Subcutaneous Doses of the Feline Insulin-Fc Fusion Proteins of SEQ ID NO: 32, SEQ ID NO: 34, and SEQ ID NO: 36

The feline insulin-Fc fusion protein configurations of SEQ ID NO: 32, SEQ ID NO: 34 and SEQ ID NO: 36 are evaluated for in vivo immunogenicity after repeated subcutaneous doses.

The insulin-Fc fusion protein configurations are manufactured in HEK293 cells according to Example 2 and purified using a Protein A column according to Example 4. The structures are confirmed according to Example 6 by non-reducing and reducing CE-SDS, and the sequences are further identified by LC-MS with glycan removal according to Example 8. The % homodimers are measured by size-exclusion chromatography according to Example 10. The in vivo bioactivity after a single dose of the insulin-Fc fusion protein configuration being tested is measured according to Example 14 and the in vivo bioactivity is measured after repeated doses according to Example 16.

It is expected that the feline insulin-Fc fusion protein configuration of SEQ ID NO: 32 (comprising the Fc fragment of SEQ ID NO: 19) and the feline insulin-Fc fusion protein configuration of SEQ ID NO: 34 (comprising the Fc fragment of SEQ ID NO: 20) will exhibit decreasing bioactivity in vivo after repeated doses. That is, the NAOC and the NAOCR do not maintain an NAOCR greater than 0.6 over at least three doses. It is further expected that the feline insulin-Fc fusion protein configuration of SEQ ID NO: 36 (comprising the Fc fragment of SEQ ID NO: 21 with the asparagine to lysine mutation at the cNg location) will exhibit sustained bioactivity in vivo after repeated doses. That is, the NAOC and the NAOCR do maintain an NAOCR greater than 0.6 over at least three doses.

Example 31: Exemplary Insulin Fc Fusion Protein Domains and Sequences

Exemplary insulin-Fc fusion protein domains and sequences used in the above Examples are shown in FIG. 4.

EQUIVALENTS

In the claims articles such as "a," "an," and "the" may mean one or more than one unless indicated to the contrary or otherwise evident from the context. Claims or descriptions that include "or" between one or more members of a group are considered satisfied if one, more than one, or all the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. In general, where the disclosure, or aspects of the disclosure, is/are referred to as comprising elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprise(s)," "comprising," "contain(s)," and "containing" are intended to be open and the use thereof permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub—range within the stated ranges in different embodiments of the disclosure, to the tenth of the unit of the lower limit of the range, unless the context clearly dictates otherwise.

Additional advantages of the various embodiments of the technology will be apparent to those skilled in the art upon review of the disclosure herein and the working examples. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

We claim:

1. A method for lowering the blood glucose of a target animal, the method comprising administering a physiologically effective amount of a fusion protein or a pharmaceutical composition thereof to the target animal, said fusion protein comprising an insulin polypeptide and an Fc fragment, wherein the insulin polypeptide and the Fc fragment are connected by a peptide linker, wherein the Fc fragment comprises the following sequence:

(SEQ ID NO: 21)
GEGPKCPVPEIPGAPSVFIFPPKPKDTLSISRTPEVTCLVVDLGPDDSNV

QITWFVDNTEMHTAKTRPREEQFKSTYRVVSVLPILHQDWLKGKEFKCKV

NSKSLPSAMERTISKAKGQPHEPQVYVLPPTQEELSENKVSVTCLIKGFH

PPDIAVEWEITGQPEPENNYQTTPPQLDSDGTYFLYSRLSVDRSHWQRGN

TYTCSVSHEALHSHHTQKSLTQSPG.

wherein the insulin polypeptide comprises the following sequence:

(SEQ ID NO: 4)
FVNQHLCGSDLVEALYLVCGERGFFYTDPTGGGPRRGIVEQCCHSICSLY

QLENYCN.

and
wherein the target animal is a cat.

2. The method of claim 1, in which the target animal is diagnosed with diabetes.

3. The method of claim 1, wherein the fusion protein is administered daily, twice weekly, or once weekly to the target animal.

4. The method of claim 1, wherein the fusion protein is administered subcutaneously.

5. The method of claim 4, the fusion protein is administered once weekly to the cat at a dose between 0.025 and 0.5 mg/kg/week.

6. The method of claim 5, wherein the NAOC after a first subcutaneous injection in the target animal is greater than 150% FBGL·days·kg/mg.

7. The method of claim 5, wherein the ratio of the NAOC after the third weekly subcutaneous injection of the fusion protein in the target animal to the NAOC after the first subcutaneous injection of the fusion protein in the target animal is greater than 0.50.

8. The method of claim 1, wherein the serum half-life of the fusion protein in the blood or serum of the target animal upon administration is longer than about 3 days.

9. The method of claim 1, wherein the time during which there is a statistically significant decrease in blood glucose level in the target animal relative to a pre-dose level is longer than one of 2 hours, 6 hours, 9 hours, 12 hours, 18 hours, 1 day, 1.5 days, 2 days, 2.5 days, 3 days, 4 days, 5 days, 6 days, or 7 days.

10. The method of claim 1, wherein said fusion protein comprises the following sequence:

```
                                             (SEQ ID NO: 36)
FVNQHLCGSDLVEALYLVCGERGFFYTDPTGGGPRRGIVEQCCHSICSLY

QLENYCNGGGGSGGGGGEGPKCPVPEIPGAPSVFIFPPKPKDTLSISRTP

EVTCLVVDLGPDDSNVQITWFVDNTEMHTAKTRPREEQFKSTYRVVSVLP

ILHQDWLKGKEFKCKVNSKSLPSAMERTISKAKGQPHEPQVYVLPPTQEE

LSENKVSVTCLIKGFHPPDIAVEWEITGQPEPENNYQTTPPQLDSDGTYF

LYSRLSVDRSHWQRGNTYTCSVSHEALHSHHTQKSLTQSPG.
```

* * * * *